US012370235B2

(12) United States Patent
Kathyana et al.

(10) Patent No.: US 12,370,235 B2
(45) Date of Patent: Jul. 29, 2025

(54) SYNTHETIC, NON-NATURAL ANTIMICROBIAL PEPTIDES INSPIRED BY *STAPHYLOCOCCUS AURICULARIS* DELTA TOXIN

(71) Applicant: University of Saskatchewan, Saskatoon (CA)

(72) Inventors: Deeyagahage Hiruni Kathyana, Saskatoon (CA); Antonio Ruzzini, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 17/685,943

(22) Filed: Mar. 3, 2022

(65) Prior Publication Data

US 2022/0280595 A1 Sep. 8, 2022

Related U.S. Application Data

(60) Provisional application No. 63/156,852, filed on Mar. 4, 2021.

(51) Int. Cl.
*A61K 38/10* (2006.01)
*A61P 31/04* (2006.01)

(52) U.S. Cl.
CPC .............. *A61K 38/10* (2013.01); *A61P 31/04* (2018.01)

(58) Field of Classification Search
None
See application file for complete search history.

(56) References Cited

U.S. PATENT DOCUMENTS

| 8,211,445 B2 | 7/2012 | Otto et al. |
| 10,174,085 B2 | 1/2019 | Aman et al. |
| 2010/0166708 A1 | 7/2010 | Gallo et al. |

FOREIGN PATENT DOCUMENTS

| WO | 2013010176 A2 | 1/2013 |
| WO | 2018037408 A2 | 3/2018 |
| WO | 2020089912 A1 | 5/2020 |

OTHER PUBLICATIONS

Betts et al, Amino Acid Properties and Consequences of Substitutions, Bioinformatics for Geneticists, (2003), pp. 289-316 (Year: 2003).*
Hammen et al, The Role of Positive Charges and Structural Segments in the Presequence of Rat Liver Aldehyde Dehydrogenase in Import into Mitochondria, The Journal of Biological Chemistry vol. 271, No. 35, Issue of Aug. 30, pp. 21041-21048, 1996 (Year: 1996).*
Wermuth, C. G. (Chairman), et al. Glossary of Terms Used in Medicinal Chemistry (IUPAC Recommendations 1998), Pure & App. Chem., vol. 70, No. 5, pp. 1129-1143, 1998 (Year: 1998).*
Cherry et al. Peptides with the same composition, hydrophobicity, and hydrophobic moment bind to phospholipid bilayers with different affinities. The Journal of Physical Chemistry B, vol. 118(43), published Oct. 20, 2014, pp. 12462-12470.
Somayaji et al. Human infections due to *Staphylococcus pseudintermedius*, an emerging zoonosis of canine origin: report of 24 cases. Diagnostic Microbiology and Infectious Disease, vol. 85(4), published May 12, 2016, pp. 471-476.
Deeyagahage and Ruzzini. Cell-Penetrating Antimicrobial Peptides Derived from an Atypical Staphylococcal δ-Toxin. Microbiology Spectrum, vol. 9(3), published Dec. 22, 2021, pp. 1-13.
Deeyagahage. Presentation slides from a departmental seminar at the University of Saskatchewan. Presented on Mar. 6, 2020, 26 pages.
Kosikowska and Lesner. Antimicrobial peptides (AMPs) as drug candidates: a patent review (2003-2015). Expert Opinion on Therapeutic Patents, vol. 26(6), published online Apr. 22, 2016, pp. 689-702.
Kang et al. The therapeutic applications of antimicrobial peptides (AMPs): a patent review. Journal of Microbiology, vol. 55(1), published Dec. 30, 2016, pp. 1-12.
Tacconelli et al. Discovery, research, and development of new antibiotics: the WHO priority list of antibiotic-resistant bacteria and tuberculosis. Lancet Infectious Disease, vol. 18(3), published Dec. 21, 2017, pp. 1-10.
UK Government and Wellcome Trust, O.N.J. Tackling drug-resistant infections globally: final report and recommendations. The review on antimicrobial resistance, published May 2016, 84 pages.
Klein et al. The changing epidemiology of methicillin-resistant *Staphylococcus aureus* in the United States: a national observational study. American Journal of Epidemiology, vol. 177(7), published Feb. 28, 2013, pp. 666-674.
Lee et al. Methicillin-resistant *Staphylococcus aureus*. Nature Reviews Disease Primers, vol. 4, Article 18033, published May 31, 2018, pp. 1-23.
Klein et al. National Costs Associated With Methicillin-Susceptible and Methicillin-Resistant *Staphylococcus aureus* Hospitalizations in the United States, 2010-2014. Clinic Infectious Diseases, vol. 68(1), published May 12, 2018, pp. 22-28.
Zhen et al. The Clinical and Economic Impact of Antibiotic Resistance in China: A Systematic Review and Meta-Analysis. Antibiotics (Basel), vol. 8(3), published Aug. 10, 2019, 27 pages.
Canadian Antimicrobial Resistance Surveillance System, Public Health Agency of Canada, published Sep. 2016, 118 pages.
Goetghebeur et al. Methicillin-resistant *Staphylococcus aureus*: A public health issue with economic consequences. Canadian Journal of Infectious Diseases and Medical Microbiology, vol. 18(1), published Jan. 2007, pp. 27-34.

(Continued)

*Primary Examiner* — Thomas S Heard
(74) *Attorney, Agent, or Firm* — Smart & Biggar LP

(57) ABSTRACT

Described herein are Staphylococcal toxins inspired peptides (STIPs) with antimicrobial activity, compositions and kits comprising the peptides, and use of the peptides to treat microbial infections. Also described are methods of inhibiting or preventing the growth of a microorganism, and methods of treating microbial infections such as bacterial infections including MRSA, and fungal infections including *C. albicans*.

8 Claims, 10 Drawing Sheets

Specification includes a Sequence Listing.

(56) References Cited

OTHER PUBLICATIONS

Bauman et al. Identifying management and disease priorities of Canadian dairy industry stakeholders. Journal of Dairy Science, vol. 99(12), published Oct. 5, 2016, pp. 10194-10203.
Canada's Dairy Industry at a Glance. Government of Canada, published 2017, 6 pages.
Canada's Dairy Industry at a Glance. Government of Canada, published 2016, 6 pages.
Jacques et al. Dairy Research Cluster Sustainable Development—Summary 2014; The Canadian Bovine Mastitis and Milk Quality Research Network, published 2014, 1 page.
Rollin et al. The cost of clinical mastitis in the first 30 days of lactation: An economic modeling tool. Preventive Veterinary Medicine, vol. 122(3), published Dec. 1, 2015, pp. 257-264.
Robbins et al. Antifungal Drugs: The Current Armamentarium and Development of New Agents. Microbiology Spectrum, vol. 4(5), published Oct. 21, 2016, pp. 1-20.
Brown et al. Hidden killers: human fungal infections. Science Translational Medicine, vol. 4, article 165, published Dec. 19, 2012, pp. 1-9.
Wilson et al. The direct cost and incidence of systemic fungal infections. Value in Health, vol. 5(1), published Jan. 2012, pp. 26-34.
Wang et al. Design of Antimicrobial Peptides: Progress Made with Human Cathelicidin LL-37. Advances Experimental Medicine and Biology, vol. 1117, published first online Apr. 13, 2019, 40 pages.
De Breij et al. The antimicrobial peptide SAAP-148 combats drug-resistant bacteria and biofilms. Science Translation Medicine, vol. 10, article 423, published Jan. 10, 2018, pp. 1-14.
Haisma et al. Antimicrobial Peptide P60.4Ac-Containing Creams and Gel for Eradication of Methicillin-Resistant *Staphylococcus aureus* from Cultured Skin and Airway Epithelial Surfaces. Antimicrobial Agents and Chemotherapy, vol. 60(7), posted online Apr. 25, 2016, pp. 4063-4072.
Nibbering et al. Eradication of meticillin-resistant *Staphylococcus aureus* from human skin by the novel LL-37-derived peptide P10 in four pharmaceutical ointments. International Journal of Antimicrobial Agents, vol. 54(5), published Jul. 26, 2019, pp. 610-618.
Haisma et al. LL-37-derived peptides eradicate multidrug-resistant *Staphylococcus aureus* from thermally wounded human skin equivalents. Antimicrobial Agents amd Chemotherapy, vol. 58(8), published Aug. 2014, pp. 4411-4419.
Dijksteel et al. Potential factors contributing to the poor antimicrobial efficacy of SAAP-148 in a rat wound infection model. Annals of Clinic Microbiology and Antimicrobials, vol. 18(1), article 38, published Dec. 3, 2019, pp. 1-12.
Cogen et al. Selective antimicrobial action is provided by phenol-soluble modulins derived from *Staphylococcus epidermidis*, a normal resident of the skin. Journal of Investigative Dermatology, vol. 130(1), published Jan. 2010, pp. 192-200.
Peschel and Otto. Phenol-soluble modulins and staphylococcal infection. Nature Review Microbiology, vol. 11(10), published Oct. 2013, pp. 667-673.
Cogen et al. *Staphylococcus epidermidis* antimicrobial delta-toxin (phenol-soluble modulin-gamma) cooperates with host antimicrobial peptides to kill group A Streptococcus. PLoS One, vol. 5(1), article e8557, published Jan. 5, 2010, pp. 1-7.
Al-Mahrous et al. Purification and characterization of a novel delta-lysin variant that inhibits *Staphylococcus aureus* and has limited hemolytic activity. Peptides, vol. 31(9), published Jun. 16, 2010, pp. 1661-1668.
Tappin et al. High-resolution 1H NMR study of the solution structure of delta-hemolysin. Biochemistry, vol. 27(5), published Mar. 8, 1988, pp. 1643-1647.
Towle et al. Solution Structures of Phenol-Soluble Modulins alpha1, alpha3, and beta2, Virulence Factors from *Staphylococcus aureus*. Biochemistry, vol. 55(34), published Aug. 15, 2016, pp. 4798-4806.
Kreger et al. Purification and properties of staphylococcal delta hemolysin. Infection and Immunity, vol. 3(3), published Mar. 1971, pp. 449-465.
Wang et al. Identification of novel cytolytic peptides as key virulence determinants for community-associated MRSA. Nature Medicine, vol. 13(12), published Nov. 11, 2007, pp. 1510-1514.
Mehlin et al. An inflammatory polypeptide complex from Staphylococcus epidermidis: isolation and characterization. Journal of Experimental Medicine, vol. 189(6), published Mar. 15, 1999, pp. 907-917.
Hoffmann and Streitfeld. The Antibiotic Activity Associated with Preparations of Delta Hemolysin of *Staphylococcus aureus*. Canadian Journal Microbiology, vol. 11, published Apr. 1965, pp. 203-211.
Joo et al. Antimicrobial activity of community-associated methicillin-resistant *Staphylococcus aureus* is caused by phenol-soluble modulin derivatives. The Journal of Biological Chemistry, vol. 286(11), published online Jan. 28, 2011, pp. 8933-8940.
Verdon et al. Characterization of anti-Legionella activity of warnericin RK and delta-lysin I from *Staphylococcus warneri*. Peptides, vol. 29(6), published Feb. 6, 2008, pp. 978-984.
Marchand et al. Anti-Legionella activity of staphylococcal hemolytic peptides. Peptides, vol. 32(5), published Feb. 1, 2011, pp. 845-851.
Gonzalez et al. Novel phenol-soluble modulin derivatives in community-associated methicillin-resistant *Staphylococcus aureus* identified through imaging mass spectrometry. The Journal of Biological Chemistry, vol. 18 (17), published Feb. 27, 2012, pp. 13889-13898.
Salinas et al. Extreme amyloid polymorphism in *Staphylococcus aureus* virulent PSMalpha peptides. Nature Communications, vol. 9(1), published Aug. 29, 2018, pp. 1-9.
Dhople and Nagaraj. Generation of analogs having potent antimicrobial and hemolytic activities with minimal changes from an inactive 16-residue peptide corresponding to the helical region of *Staphylococcus aureus* delta-toxin. Protein Engineering, vol. 8(3), published Mar. 1995, pp. 315-318.
Dhople and Nagaraj. Conformation and activity of delta-lysin and its analogs. Peptides, vol. 26(2), published Nov. 18, 2004, pp. 217-225.
Bojer et al. Quorum Sensing-Regulated Phenol-Soluble Modulins Limit Persister Cell Populations in *Staphylococcus aureus*. Frontiers in Microbiology, vol. 9, article 255, published Feb. 20, 2018, pp. 1-12.
Baldry et al. Phenol-Soluble Modulins Modulate Persister Cell Formation in *Staphylococcus aureus*. Frontiers in Microbiology, vol. 11, article 573253, published Nov. 9, 2020, pp. 1-7.
Zeng et al. Phenol-Soluble-Modulin-Inspired Amphipathic Peptides Have Bactericidal Activity against Multidrug-Resistant Bacteria. ChemMedChem, vol. 14(16), published Jul. 30, 2019, pp. 1547-1559.
Somerville et al. Synthesis and deformylation of *Staphylococcus aureus* delta-toxin are linked to tricarboxylic acid cycle activity. Journal of Bacteriology, vol. 185(22), published Nov. 2003, pp. 6686-6694.
Jones et al. Relative quantitative comparisons of the extracellular protein profiles of *Staphylococcus aureus* JAMS-1 and its sarA, agr, and sarA agr regulatory mutants using one-dimensional polyacrylamide gel electrophoresis and nanocapillary liquid chromatography coupled with tandem mass spectrometry. Journal of Bacteriology, vol. 190(15), published Aug. 2008, pp. 5265-5278.
Schwartz et al. Functional amyloids composed of phenol soluble modulins stabilize *Staphylococcus aureus* biofilms. PLoS Pathogens, vol. 8(6), article e1002744, published Jun. 7, 2012, pp. 1-11.
Lechner et al. *Staphylococcus aureus* Persisters Tolerant to Bactericidal Antibiotics. Journal of Molecular Microbiology and Biotechnology, vol. 22(4), published Sep. 14, 2013, pp. 235-244.
Tayeb-Fligelman et al. The cytotoxic *Staphylococcus aureus* PSMalpha3 reveals a cross-alpha amyloid-like fibril. Science, vol. 355(6327), published Feb. 24, 2017, 11 pages.
Tayeb-Fligelman et al. *Staphylococcus aureus* PSMalpha3 Cross-alpha Fibril Polymorphism and Determinants of Cytotoxicity. Structure 28, vol. 28(3), published on Jan. 6, 2020, pp. 301-313.

(56) References Cited

OTHER PUBLICATIONS

Yao et al. Use of a Stereochemical Strategy to Probe the Mechanism of Phenol-Soluble Modulin alpha3 Toxicity. Journal of the American Chemical Society, vol. 141(19), published May 2, 2019, pp. 7660-7664.

* cited by examiner

```
STIP1  I I S T I S D L V K W I I D T V N K F T K
STIP2  I I S T I G D L V K W I I D T V N K F T K
STIP3  I V E T V G G L V K W I L D T V K K F A
STIP4  I I S T I V E F V K L I A E T I A K F M K
STIP5  I I S T I G D L V K W I I D T V N K F K K
STIP6  I I G T I N D L I K W I A D T V E K Y K K
STIP7  I I S T I G D L I K W I I D T V K K F K K
```
FIG. 1A
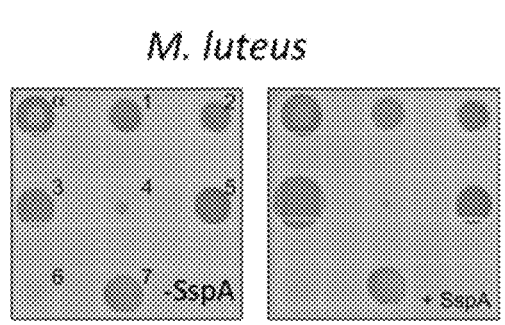
FIG. 1B
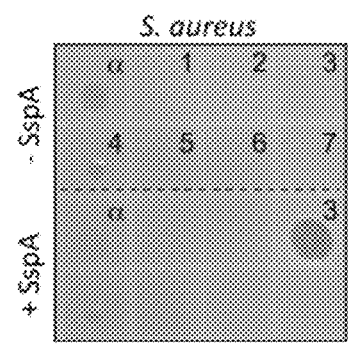
FIG. 1C
```
STIP3   I V E T V G G L V K W I L D T V K K F A
(I)           T V G G L V K W I L D T V K K F A
(II)    I V E T V G G L V K W I L D
(III)         T V G G L V K W I L D
(IV)                              T V K K F A
```
FIG. 1D
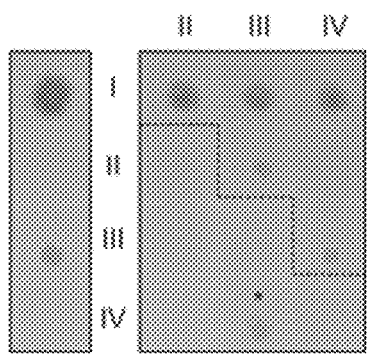
FIG. 1E
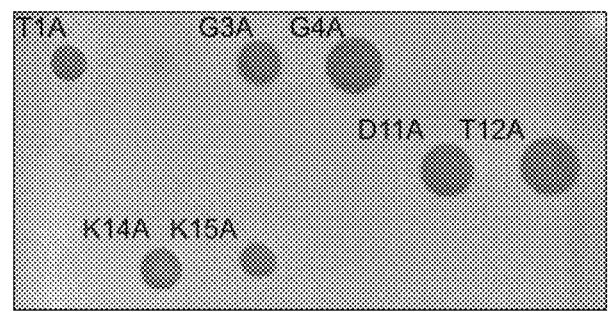
FIG. 1F

FIG. 6A  FIG. 6B

```
                       SEQUENCE LISTING

<160> NUMBER OF SEQ ID NOS: 89

<210> SEQ ID NO 1
<211> LENGTH: 17
<212> TYPE: PRT
<213> ORGANISM: S. auricularis

<400> SEQUENCE: 1

Thr Val Gly Gly Leu Val Lys Trp Ile Leu Asp Thr Val Lys Lys Phe
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Thr Val Gly Gly Leu Val Lys Trp Ile Leu Ala Thr Val Lys Lys Phe
1               5                   10                  15

Ala

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Thr Val Gly Gly Leu Val Lys Trp Ile Leu Lys Thr Val Lys Lys Phe
1               5                   10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: Synthetic construct
```

<400> SEQUENCE: 4

Thr Val Gly Gly Leu Val Lys Trp Ile Leu Asn Thr Val Lys Lys Phe
1               5                   10                  15

Ala

<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

Thr Val Gly Gly Leu Val Lys Trp Ile Leu Asp Thr Val Lys Lys Phe
1               5                   10                  15

Ile

<210> SEQ ID NO 6
<211> LENGTH: 17
<212> TYPE: PRT
<213> ORGANISM: Artificial Sequence
<220> FEATURE:
<223> OTHER INFORMATION: Synthetic construct

<400> SEQUENCE: 6

Thr Val Gly Gly Leu Val Lys Trp Ile Leu Asp Thr Val Lys Lys Phe
1               5                   10                  15

Trp

<210> SEQ ID NO 7
<211> LENGTH: 17
<212> TYPE: PRT
<213> ORGANISM: Artificial Sequence
<220> FEATURE:
<223> OTHER INFORMATION: Synthetic construct

<400> SEQUENCE: 7

Thr Val Gly Gly Leu Val Lys Trp Ile Leu Asp Thr Val Lys Lys Phe
1               5                   10                  15

Lys

<210> SEQ ID NO 8
<211> LENGTH: 17
<212> TYPE: PRT
<213> ORGANISM: Artificial Sequence
<220> FEATURE:
<223> OTHER INFORMATION: Synthetic construct

<400> SEQUENCE: 8

Thr Val Gly Val Leu Val Lys Trp Ile Leu Asp Thr Val Lys Lys Phe
1               5                   10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: Synthetic construct

<400> SEQUENCE: 9

Thr Val Gly Gly Leu Val Lys Trp Ile Leu Asp Val Val Lys Lys Phe

<210> SEQ ID NO 10
<211> LENGTH: 17
<212> TYPE: PRT
<213> ORGANISM: Artificial Sequence
<220> FEATURE:
<223> OTHER INFORMATION: Synthetic construct

<400> SEQUENCE: 10

Thr Val Gly Gly Leu Val Lys Trp Ile Leu Asp Trp Val Lys Lys Phe
1               5                   10                  15
Ala

<210> SEQ ID NO 11
<211> LENGTH: 17
<212> TYPE: PRT
<213> ORGANISM: Artificial Sequence
<220> FEATURE:
<223> OTHER INFORMATION: Synthetic construct

<400> SEQUENCE: 11

Thr Val Gly Gly Leu Val Lys Trp Ile Leu Asp Thr Phe Lys Lys Phe
1               5                   10                  15
Ala

<210> SEQ ID NO 12
<211> LENGTH: 17
<212> TYPE: PRT
<213> ORGANISM: Artificial Sequence
<220> FEATURE:
<223> OTHER INFORMATION: Synthetic construct

<400> SEQUENCE: 12

Thr Val Gly Gly Leu Val Lys Trp Ile Leu Ala Ala Val Lys Lys Phe
1               5                   10                  15
Ala

<210> SEQ ID NO 13
<211> LENGTH: 17
<212> TYPE: PRT
<213> ORGANISM: Artificial Sequence
<220> FEATURE:
<223> OTHER INFORMATION: Synthetic construct

<400> SEQUENCE: 13

Thr Val Gly Gly Leu Val Lys Trp Ile Leu Lys Ala Val Lys Lys Phe
1               5                   10                  15
Ala

<210> SEQ ID NO 14
<211> LENGTH: 17
<212> TYPE: PRT
<213> ORGANISM: Artificial Sequence
<220> FEATURE:
<223> OTHER INFORMATION: Synthetic construct

<400> SEQUENCE: 14

Thr Val Lys Gly Leu Val Lys Trp Ile Leu Asn Val Val Lys Lys Phe
1               5                   10                  15
Ala

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Thr Val Ala Gly Leu Val Lys Trp Ile Leu Ala Thr Val Lys Lys Phe
1               5                   10                  15

Ala

<210> SEQ ID NO 16
<211> LENGTH: 17
<212> TYPE: PRT
<213> ORGANISM: Artificial Sequence
<220> FEATURE:
<223> OTHER INFORMATION: Synthetic construct

<400> SEQUENCE: 16

Thr Val Lys Gly Leu Val Lys Trp Ile Leu Ala Thr Val Lys Lys Phe
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Synthetic construct

<400> SEQUENCE: 17

Thr Val Asp Gly Leu Val Lys Trp Ile Leu Ala Thr Val Lys Lys Phe
1               5                   10                  15

Ala

<210> SEQ ID NO 18
<211> LENGTH: 17
<212> TYPE: PRT
<213> ORGANISM: Artificial Sequence
<220> FEATURE:
<223> OTHER INFORMATION: Synthetic construct

<400> SEQUENCE: 18

Thr Val Lys Lys Leu Val Lys Trp Ile Leu Lys Thr Val Lys Lys Phe
1               5                   10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Synthetic construct

<400> SEQUENCE: 19

Thr Val Lys Ala Leu Val Lys Trp Ile Leu Lys Thr Val Ala Lys Phe
1               5                   10                  15

Ala

<210> SEQ ID NO 20
<211> LENGTH: 17
<212> TYPE: PRT

<213> ORGANISM: Artificial Sequence
<220> FEATURE:
<223> OTHER INFORMATION: Synthetic construct

<400> SEQUENCE: 20

Thr Val Arg Ala Leu Val Lys Trp Ile Leu Arg Thr Val Ala Lys Phe
1               5                   10                  15
Ala

<210> SEQ ID NO 21
<211> LENGTH: 17
<212> TYPE: PRT
<213> ORGANISM: Artificial Sequence
<220> FEATURE:
<223> OTHER INFORMATION: Synthetic construct

<400> SEQUENCE: 21

Thr Val Lys Ala Leu Val Lys Trp Ile Leu Lys Thr Val Ala Lys Phe
1               5                   10                  15
Trp

<210> SEQ ID NO 22
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is L-ornithine
<220> FEATURE:
<221> NAME/KEY: MISC_FEATURE
<222> LOCATION: (7)..(7)
<223> OTHER INFORMATION: Xaa is L-ornithine
<220> FEATURE:
<221> NAME/KEY: MISC_FEATURE
<222> LOCATION: (11)..(11)
<223> OTHER INFORMATION: Xaa is L-ornithine
<220> FEATURE:
<221> NAME/KEY: MISC_FEATURE
<222> LOCATION: (15)..(15)
<223> OTHER INFORMATION: Xaa is L-ornithine

<400> SEQUENCE: 22

Thr Val Xaa Ala Leu Val Xaa Trp Ile Leu Xaa Thr Val Ala Xaa Phe
1               5                   10                  15
Ala

<210> SEQ ID NO 23
<211> LENGTH: 17
<212> TYPE: PRT
<213> ORGANISM: Artificial Sequence
<220> FEATURE:
<223> OTHER INFORMATION: Synthetic construct

<400> SEQUENCE: 23

Thr Val Arg Ala Leu Val Arg Trp Ile Leu Arg Thr Val Ala Arg Phe
1               5                   10                  15
Ala

<210> SEQ ID NO 24
<211> LENGTH: 17
<212> TYPE: PRT
<213> ORGANISM: Artificial Sequence
<220> FEATURE:
<223> OTHER INFORMATION: Synthetic construct

<400> SEQUENCE: 24

Thr Val Gly Val Leu Val Lys Trp Ile Leu Asn Val Val Ala Lys Phe
1               5                   10                  15

Ala

<210> SEQ ID NO 25
<211> LENGTH: 17
<212> TYPE: PRT
<213> ORGANISM: Artificial Sequence
<220> FEATURE:
<223> OTHER INFORMATION: Synthetic construct

<400> SEQUENCE: 25

Thr Val Lys Phe Leu Val Lys Trp Ile Leu Lys Trp Val Ala Lys Phe
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: Synthetic construct

<400> SEQUENCE: 26

Thr Val Lys Val Leu Val Lys Trp Ile Leu Lys Val Val Ala Lys Phe
1               5                   10                  15

Ala

<210> SEQ ID NO 27
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (17)..(17)
<223> OTHER INFORMATION: AMIDATION

<400> SEQUENCE: 27

Thr Val Gly Gly Leu Val Lys Trp Ile Leu Asp Thr Val Lys Lys Phe
1               5                   10                  15

Ala

<210> SEQ ID NO 28
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (17)..(17)
<223> OTHER INFORMATION: AMIDATION

<400> SEQUENCE: 28

Thr Val Gly Gly Leu Val Lys Trp Ile Leu Ala Thr Val Lys Lys Phe
1               5                   10                  15

Ala

<210> SEQ ID NO 29
<211> LENGTH: 17

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (17)..(17)
<223> OTHER INFORMATION: AMIDATION

<400> SEQUENCE: 29

Thr Val Gly Gly Leu Val Lys Trp Ile Leu Lys Thr Val Lys Lys Phe
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (17)..(17)
<223> OTHER INFORMATION: AMIDATION

<400> SEQUENCE: 30

Thr Val Lys Gly Leu Val Lys Trp Ile Leu Asn Val Val Lys Lys Phe
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (17)..(17)
<223> OTHER INFORMATION: AMIDATION

<400> SEQUENCE: 31

Thr Val Lys Ala Leu Val Lys Trp Ile Leu Lys Thr Val Ala Lys Phe
1               5                   10                  15

Trp

<210> SEQ ID NO 32
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is either Gly, Lys, Ala, Arg or L-ornithine
<220> FEATURE:
<221> NAME/KEY: MISC_FEATURE
<222> LOCATION: (4)..(4)
<223> OTHER INFORMATION: Xaa is either Gly, Lys, Ala, Phe or Val
<220> FEATURE:
<221> NAME/KEY: MISC_FEATURE
<222> LOCATION: (7)..(7)
<223> OTHER INFORMATION: Xaa is either Lys, Arg or L-ornithine
<220> FEATURE:
<221> NAME/KEY: MISC_FEATURE
<222> LOCATION: (11)..(11)
<223> OTHER INFORMATION: Xaa is either Asp, Ala, Lys, Asn, Arg or
      L-ornithine
<220> FEATURE:
```

```
<221> NAME/KEY: MISC_FEATURE
<222> LOCATION: (12)..(12)
<223> OTHER INFORMATION: Xaa is either Thr, Val, Trp or Ala
<220> FEATURE:
<221> NAME/KEY: MISC_FEATURE
<222> LOCATION: (13)..(13)
<223> OTHER INFORMATION: Xaa is either Val or Phe
<220> FEATURE:
<221> NAME/KEY: MISC_FEATURE
<222> LOCATION: (14)..(14)
<223> OTHER INFORMATION: Xaa is either Lys or Ala
<220> FEATURE:
<221> NAME/KEY: MISC_FEATURE
<222> LOCATION: (15)..(15)
<223> OTHER INFORMATION: Xaa is either Lys, Arg or L-ornithine
<220> FEATURE:
<221> NAME/KEY: MISC_FEATURE
<222> LOCATION: (17)..(17)
<223> OTHER INFORMATION: Xaa is either Ala, Ile, Lys or Trp

<400> SEQUENCE: 32

Thr Val Xaa Xaa Leu Val Xaa Trp Ile Leu Xaa Xaa Xaa Xaa Xaa Phe
1               5                  10                  15

Xaa

<210> SEQ ID NO 33
<211> LENGTH: 21
<212> TYPE: PRT
<213> ORGANISM: S. aureus

<400> SEQUENCE: 33

Met Ser Ile Ile Ala Gly Ile Ile Lys Phe Ile Lys Gly Leu Ile Glu
1               5                  10                  15

Lys Phe Thr Gly Lys
            20

<210> SEQ ID NO 34
<211> LENGTH: 25
<212> TYPE: PRT
<213> ORGANISM: S. aureus

<400> SEQUENCE: 34

Met Ala Ala Asp Ile Ile Ser Thr Ile Ser Asp Leu Val Lys Trp Ile
1               5                  10                  15

Ile Asp Thr Val Asn Lys Phe Thr Lys
            20                  25

<210> SEQ ID NO 35
<211> LENGTH: 24
<212> TYPE: PRT
<213> ORGANISM: S. aureus

<400> SEQUENCE: 35

Ala Gln Asp Ile Ile Ser Thr Ile Gly Asp Leu Val Lys Trp Ile Ile
1               5                  10                  15

Asp Thr Val Asn Lys Phe Thr Lys
            20

<210> SEQ ID NO 36
<211> LENGTH: 24
<212> TYPE: PRT
<213> ORGANISM: S. auricularis

<400> SEQUENCE: 36

Met Thr Lys Asp Ile Val Glu Thr Val Gly Gly Leu Val Lys Trp Ile
1               5                  10                  15
```

Leu Asp Thr Val Lys Lys Phe Ala
            20

<210> SEQ ID NO 37
<211> LENGTH: 28
<212> TYPE: PRT
<213> ORGANISM: S. cornubiensis

<400> SEQUENCE: 37

Met Leu Thr Met Ala Ala Asp Ile Ile Ser Thr Ile Val Glu Phe Val
1               5                   10                  15

Lys Leu Ile Ala Glu Thr Ile Ala Lys Phe Met Lys
            20                  25

<210> SEQ ID NO 38
<211> LENGTH: 25
<212> TYPE: PRT
<213> ORGANISM: S. epidermidis

<400> SEQUENCE: 38

Met Ala Ala Asn Ile Ile Ser Thr Ile Gly Asp Leu Val Lys Trp Ile
1               5                   10                  15

Ile Asp Thr Val Asn Lys Phe Lys Lys
            20                  25

<210> SEQ ID NO 39
<211> LENGTH: 25
<212> TYPE: PRT
<213> ORGANISM: S. massiliensis

<400> SEQUENCE: 39

Met Ala Gly Asp Ile Ile Gly Thr Ile Asn Asp Leu Ile Lys Trp Ile
1               5                   10                  15

Ala Asp Thr Val Glu Lys Tyr Lys Lys
            20                  25

<210> SEQ ID NO 40
<211> LENGTH: 25
<212> TYPE: PRT
<213> ORGANISM: S. saccharolyticus

<400> SEQUENCE: 40

Met Ala Ala Asp Ile Ile Ser Thr Ile Gly Asp Leu Ile Lys Trp Ile
1               5                   10                  15

Ile Asp Thr Val Lys Lys Phe Lys Lys
            20                  25

<210> SEQ ID NO 41
<211> LENGTH: 21
<212> TYPE: PRT
<213> ORGANISM: S. aureus

<400> SEQUENCE: 41

Ile Ile Ser Thr Ile Ser Asp Leu Val Lys Trp Ile Ile Asp Thr Val
1               5                   10                  15

Asn Lys Phe Thr Lys
            20

<210> SEQ ID NO 42
<211> LENGTH: 7
<212> TYPE: PRT
<213> ORGANISM: S. aureus

```
<400> SEQUENCE: 42

Ile Ile Ser Thr Ile Ser Asp
1               5

<210> SEQ ID NO 43
<211> LENGTH: 14
<212> TYPE: PRT
<213> ORGANISM: S. aureus

<400> SEQUENCE: 43

Leu Val Lys Trp Ile Ile Asp Thr Val Asn Lys Phe Thr Lys
1               5                   10

<210> SEQ ID NO 44
<211> LENGTH: 7
<212> TYPE: PRT
<213> ORGANISM: S. aureus

<400> SEQUENCE: 44

Thr Val Asn Lys Phe Thr Lys
1               5

<210> SEQ ID NO 45
<211> LENGTH: 7
<212> TYPE: PRT
<213> ORGANISM: S. aureus S. epidermidis

<400> SEQUENCE: 45

Leu Val Lys Trp Ile Ile Asp
1               5

<210> SEQ ID NO 46
<211> LENGTH: 21
<212> TYPE: PRT
<213> ORGANISM: S. aureus

<400> SEQUENCE: 46

Ile Ile Ser Thr Ile Gly Asp Leu Val Lys Trp Ile Ile Asp Thr Val
1               5                   10                  15

Asn Lys Phe Thr Lys
            20

<210> SEQ ID NO 47
<211> LENGTH: 7
<212> TYPE: PRT
<213> ORGANISM: S. aureus S. epidermidis

<400> SEQUENCE: 47

Ile Ile Ser Thr Ile Gly Asp
1               5

<210> SEQ ID NO 48
<211> LENGTH: 20
<212> TYPE: PRT
<213> ORGANISM: S. auricularis

<400> SEQUENCE: 48

Ile Val Glu Thr Val Gly Gly Leu Val Lys Trp Ile Leu Asp Thr Val
1               5                   10                  15

Lys Lys Phe Ala
            20
```

```
<210> SEQ ID NO 49
<211> LENGTH: 3
<212> TYPE: PRT
<213> ORGANISM: S. auricularis

<400> SEQUENCE: 49

Ile Val Glu
1

<210> SEQ ID NO 50
<211> LENGTH: 6
<212> TYPE: PRT
<213> ORGANISM: S. auricularis

<400> SEQUENCE: 50

Thr Val Lys Lys Phe Ala
1               5

<210> SEQ ID NO 51
<211> LENGTH: 11
<212> TYPE: PRT
<213> ORGANISM: S. auricularis

<400> SEQUENCE: 51

Thr Val Gly Gly Leu Val Lys Trp Ile Leu Asp
1               5                   10

<210> SEQ ID NO 52
<211> LENGTH: 21
<212> TYPE: PRT
<213> ORGANISM: S. cornubiensis

<400> SEQUENCE: 52

Ile Ile Ser Thr Ile Val Glu Phe Val Lys Leu Ile Ala Glu Thr Ile
1               5                   10                  15

Ala Lys Phe Met Lys
            20

<210> SEQ ID NO 53
<211> LENGTH: 7
<212> TYPE: PRT
<213> ORGANISM: S. cornubiensis

<400> SEQUENCE: 53

Ile Ile Ser Thr Ile Val Glu
1               5

<210> SEQ ID NO 54
<211> LENGTH: 14
<212> TYPE: PRT
<213> ORGANISM: S. cornubiensis

<400> SEQUENCE: 54

Phe Val Lys Leu Ile Ala Glu Thr Ile Ala Lys Phe Met Lys
1               5                   10

<210> SEQ ID NO 55
<211> LENGTH: 7
<212> TYPE: PRT
<213> ORGANISM: S. cornubiensis

<400> SEQUENCE: 55

Thr Ile Ala Lys Phe Met Lys
1               5
```

<210> SEQ ID NO 56
<211> LENGTH: 21
<212> TYPE: PRT
<213> ORGANISM: S. epidermidis

<400> SEQUENCE: 56

Ile Ile Ser Thr Ile Gly Asp Leu Val Lys Trp Ile Ile Asp Thr Val
1               5                   10                  15

Asn Lys Phe Lys Lys
            20

<210> SEQ ID NO 57
<211> LENGTH: 7
<212> TYPE: PRT
<213> ORGANISM: S. epidermidis

<400> SEQUENCE: 57

Thr Val Asn Lys Phe Lys Lys
1               5

<210> SEQ ID NO 58
<211> LENGTH: 21
<212> TYPE: PRT
<213> ORGANISM: S. massiliensis

<400> SEQUENCE: 58

Ile Ile Gly Thr Ile Asn Asp Leu Ile Lys Trp Ile Ala Asp Thr Val
1               5                   10                  15

Glu Lys Tyr Lys Lys
            20

<210> SEQ ID NO 59
<211> LENGTH: 7
<212> TYPE: PRT
<213> ORGANISM: S. massiliensis

<400> SEQUENCE: 59

Ile Ile Gly Thr Ile Asn Asp
1               5

<210> SEQ ID NO 60
<211> LENGTH: 4
<212> TYPE: PRT
<213> ORGANISM: S. massiliensis

<400> SEQUENCE: 60

Lys Tyr Lys Lys
1

<210> SEQ ID NO 61
<211> LENGTH: 7
<212> TYPE: PRT
<213> ORGANISM: S. massiliensis

<400> SEQUENCE: 61

Leu Ile Lys Trp Ile Ala Asp
1               5

<210> SEQ ID NO 62
<211> LENGTH: 10
<212> TYPE: PRT
<213> ORGANISM: S. massiliensis

<400> SEQUENCE: 62

```
Leu Ile Lys Trp Ile Ala Asp Thr Val Glu
1               5                   10

<210> SEQ ID NO 63
<211> LENGTH: 21
<212> TYPE: PRT
<213> ORGANISM: S. saccharolyticus

<400> SEQUENCE: 63

Ile Ile Ser Thr Ile Gly Asp Leu Ile Lys Trp Ile Asp Thr Val
1               5                   10                  15

Lys Lys Phe Lys Lys
            20

<210> SEQ ID NO 64
<211> LENGTH: 14
<212> TYPE: PRT
<213> ORGANISM: S. saccharolyticus

<400> SEQUENCE: 64

Ile Ile Ser Thr Ile Gly Asp Leu Ile Lys Trp Ile Ile Asp
1               5                   10

<210> SEQ ID NO 65
<211> LENGTH: 7
<212> TYPE: PRT
<213> ORGANISM: S. saccharolyticus

<400> SEQUENCE: 65

Thr Val Lys Lys Phe Lys Lys
1               5

<210> SEQ ID NO 66
<211> LENGTH: 7
<212> TYPE: PRT
<213> ORGANISM: S. auricularis

<400> SEQUENCE: 66

Met Thr Lys Asp Ile Val Glu
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic construct

<400> SEQUENCE: 67

Ala Val Gly Gly Leu Val Lys Trp Ile Leu Asp Thr Val Lys Lys Phe
1               5                   10                  15

Ala

<210> SEQ ID NO 68
<211> LENGTH: 17
<212> TYPE: PRT
<213> ORGANISM: Artificial Sequence
<220> FEATURE:
<223> OTHER INFORMATION: Synthetic construct

<400> SEQUENCE: 68

Thr Ala Gly Gly Leu Val Lys Trp Ile Leu Asp Thr Val Lys Lys Phe
1               5                   10                  15
```

Ala

<210> SEQ ID NO 69
<211> LENGTH: 17
<212> TYPE: PRT
<213> ORGANISM: Artificial Sequence
<220> FEATURE:
<223> OTHER INFORMATION: Synthetic construct

<400> SEQUENCE: 69

Thr Val Ala Gly Leu Val Lys Trp Ile Leu Asp Thr Val Lys Lys Phe
1               5                   10                  15

Ala

<210> SEQ ID NO 70
<211> LENGTH: 17
<212> TYPE: PRT
<213> ORGANISM: Artificial Sequence
<220> FEATURE:
<223> OTHER INFORMATION: Synthetic construct

<400> SEQUENCE: 70

Thr Val Gly Ala Leu Val Lys Trp Ile Leu Asp Thr Val Lys Lys Phe
1               5                   10                  15

Ala

<210> SEQ ID NO 71
<211> LENGTH: 17
<212> TYPE: PRT
<213> ORGANISM: Artificial Sequence
<220> FEATURE:
<223> OTHER INFORMATION: Synthetic construct

<400> SEQUENCE: 71

Thr Val Gly Gly Ala Val Lys Trp Ile Leu Asp Thr Val Lys Lys Phe
1               5                   10                  15

Ala

<210> SEQ ID NO 72
<211> LENGTH: 17
<212> TYPE: PRT
<213> ORGANISM: Artificial Sequence
<220> FEATURE:
<223> OTHER INFORMATION: Synthetic construct

<400> SEQUENCE: 72

Thr Val Gly Gly Leu Ala Lys Trp Ile Leu Asp Thr Val Lys Lys Phe
1               5                   10                  15

Ala

<210> SEQ ID NO 73
<211> LENGTH: 17
<212> TYPE: PRT
<213> ORGANISM: Artificial Sequence
<220> FEATURE:
<223> OTHER INFORMATION: Synthetic construct

<400> SEQUENCE: 73

Thr Val Gly Gly Leu Val Ala Trp Ile Leu Asp Thr Val Lys Lys Phe
1               5                   10                  15

Ala

<210> SEQ ID NO 74

```
<211> LENGTH: 17
<212> TYPE: PRT
<213> ORGANISM: Artificial Sequence
<220> FEATURE:
<223> OTHER INFORMATION: Synthetic construct

<400> SEQUENCE: 74

Thr Val Gly Gly Leu Val Lys Ala Ile Leu Asp Thr Val Lys Lys Phe
1               5                   10                  15

Ala

<210> SEQ ID NO 75
<211> LENGTH: 17
<212> TYPE: PRT
<213> ORGANISM: Artificial Sequence
<220> FEATURE:
<223> OTHER INFORMATION: Synthetic construct

<400> SEQUENCE: 75

Thr Val Gly Gly Leu Val Lys Trp Ala Leu Asp Thr Val Lys Lys Phe
1               5                   10                  15

Ala

<210> SEQ ID NO 76
<211> LENGTH: 17
<212> TYPE: PRT
<213> ORGANISM: Artificial Sequence
<220> FEATURE:
<223> OTHER INFORMATION: Synthetic construct

<400> SEQUENCE: 76

Thr Val Gly Gly Leu Val Lys Trp Ile Ala Asp Thr Val Lys Lys Phe
1               5                   10                  15

Ala

<210> SEQ ID NO 77
<211> LENGTH: 17
<212> TYPE: PRT
<213> ORGANISM: Artificial Sequence
<220> FEATURE:
<223> OTHER INFORMATION: Synthetic construct

<400> SEQUENCE: 77

Thr Val Gly Gly Leu Val Lys Trp Ile Leu Asp Ala Val Lys Lys Phe
1               5                   10                  15

Ala

<210> SEQ ID NO 78
<211> LENGTH: 17
<212> TYPE: PRT
<213> ORGANISM: Artificial Sequence
<220> FEATURE:
<223> OTHER INFORMATION: Synthetic construct

<400> SEQUENCE: 78

Thr Val Gly Gly Leu Val Lys Trp Ile Leu Asp Thr Ala Lys Lys Phe
1               5                   10                  15

Ala

<210> SEQ ID NO 79
<211> LENGTH: 17
<212> TYPE: PRT
<213> ORGANISM: Artificial Sequence
<220> FEATURE:
```

<223> OTHER INFORMATION: Synthetic construct

<400> SEQUENCE: 79

Thr Val Gly Gly Leu Val Lys Trp Ile Leu Asp Thr Val Ala Lys Phe
1               5                   10                  15

Ala

<210> SEQ ID NO 80
<211> LENGTH: 17
<212> TYPE: PRT
<213> ORGANISM: Artificial Sequence
<220> FEATURE:
<223> OTHER INFORMATION: Synthetic construct

<400> SEQUENCE: 80

Thr Val Gly Gly Leu Val Lys Trp Ile Leu Asp Thr Val Lys Ala Phe
1               5                   10                  15

Ala

<210> SEQ ID NO 81
<211> LENGTH: 17
<212> TYPE: PRT
<213> ORGANISM: Artificial Sequence
<220> FEATURE:
<223> OTHER INFORMATION: Synthetic construct

<400> SEQUENCE: 81

Thr Val Gly Gly Leu Val Lys Trp Ile Leu Asp Thr Val Lys Lys Ala
1               5                   10                  15

Ala

<210> SEQ ID NO 82
<211> LENGTH: 7
<212> TYPE: PRT
<213> ORGANISM: S. aureus

<400> SEQUENCE: 82

Lys Leu Phe Lys Phe Phe Lys
1               5

<210> SEQ ID NO 83
<211> LENGTH: 6
<212> TYPE: PRT
<213> ORGANISM: S. aureus

<400> SEQUENCE: 83

Leu Phe Lys Phe Phe Lys
1               5

<210> SEQ ID NO 84
<211> LENGTH: 18
<212> TYPE: PRT
<213> ORGANISM: S. condimenti

<400> SEQUENCE: 84

Thr Val Lys Ser Phe Val Asn Leu Ile Leu Asp Thr Val Lys Lys Tyr
1               5                   10                  15

Ala Lys

<210> SEQ ID NO 85
<211> LENGTH: 18
<212> TYPE: PRT
<213> ORGANISM: Artificial Sequence

```
<220> FEATURE:
<223> OTHER INFORMATION: Synthetic construct

<400> SEQUENCE: 85

Thr Val Lys Ser Phe Val Asn Leu Ile Leu Lys Thr Val Lys Lys Tyr
1               5                   10                  15

Ala Lys

<210> SEQ ID NO 86
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (18)..(18)
<223> OTHER INFORMATION: AMIDATION

<400> SEQUENCE: 86

Thr Val Lys Ser Phe Val Asn Leu Ile Leu Lys Thr Val Lys Lys Tyr
1               5                   10                  15

Ala Lys

<210> SEQ ID NO 87
<211> LENGTH: 18
<212> TYPE: PRT
<213> ORGANISM: S. pettenkoferi

<400> SEQUENCE: 87

Thr Val Thr Lys Phe Val Lys Leu Ile Ala Glu Thr Val Lys Lys Phe
1               5                   10                  15

Thr Lys

<210> SEQ ID NO 88
<211> LENGTH: 18
<212> TYPE: PRT
<213> ORGANISM: Artificial Sequence
<220> FEATURE:
<223> OTHER INFORMATION: Synthetic construct

<400> SEQUENCE: 88

Thr Val Thr Lys Phe Val Lys Leu Ile Ala Lys Thr Val Lys Lys Phe
1               5                   10                  15

Thr Lys

<210> SEQ ID NO 89
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (18)..(18)
<223> OTHER INFORMATION: AMIDATION

<400> SEQUENCE: 89

Thr Val Thr Lys Phe Val Lys Leu Ile Ala Lys Thr Val Lys Lys Phe
1               5                   10                  15

Thr Lys
```

SYNTHETIC, NON-NATURAL ANTIMICROBIAL PEPTIDES INSPIRED BY *STAPHYLOCOCCUS AURICULARIS* DELTA TOXIN

CROSS-REFERENCE TO RELATED APPLICATIONS

This application claims the benefit of priority to U.S. Provisional Application No. 63/156,852, filed Mar. 4, 2021, the contents of which are incorporated herein by reference in their entirety.

INCORPORATION OF SEQUENCE LISTING

A computer readable form of the Sequence Listing "13764-P63519US01_SequenceListing" (22,945 bytes) created on Mar. 2, 2022, is herein incorporated by reference.

FIELD

The present disclosure relates to anti-microbial peptides. Also disclosed are pharmaceutical compositions and use of the peptides for treating microbial infections.

INTRODUCTION

Microbial infections, including bacterial and fungal infections are a major cause of mortality worldwide, and cause disease in a wide variety of animal species including humans, livestock, and companion animals. Among the long list of notorious bacterial species, *Staphylococcus aureus* is a prominent opportunistic pathogen that continues to challenge well-being and health care systems. *S. aureus* is a remarkably adaptable organism with antimicrobial resistance (AMR) genes widespread throughout the strains that commonly infect humans. In 2017, the World Health Organization (WHO) released a list of priority organisms for the research and development of antibiotics that included methicillin- and vancomycin-resistant *S. aureus* (MRSA and VRSA)[1]. Currently, drug resistant bacteria cause ~700,000 deaths/year and this number is predicted to dramatically increase to ~10 million deaths/year by 2050[2].

The severity of *S. aureus* infections can range from atopic dermatitis (eczema) to potentially fatal septicemia. A recent study in the United States estimated that ~60% of human *S. aureus* infections are β-lactam resistant MRSA[3], though specific rates of MRSA show significant geographical variation across the globe[4]. The prevalence of staphylococcal infections results from common carriage: about one half of the healthy population is at least occasionally colonized by *S. aureus*. Severe cases of *S. aureus* are associated with high costs of hospitalizations caused by both methicillin-sensitive (MSSA) and MRSA. Analysis of national costs of hospitalizations in the United States between 2010-2014 from *S. aureus*-associated pneumonia and other diseases, including sepsis, revealed a similar burden is caused by MSSA and MRSA[5]. For patients with pneumonia, hospital costs were $40,725 USD and $38,561 for infections caused by MSSA and MRSA, respectively. Likewise, other infections cost an average of $15,000 per hospitalization. The slightly lower costs of MRSA infections are likely related to disease outcomes as there were 16,485 MRSA versus 11,305 MSSA-related deaths in the United States in 2014. In China, the median cost of hospitalization caused by MSSA and MRSA in 2015 were estimated at $8,230 and $11,450, respectively[6]. These costs include antibiotic and other required medicines, which account for ~47% and ~60% of the overall costs of treating MSSA and MRSA infections. In Canada, there are ~3,000 MRSA-related hospitalizations annually[7], and the last national estimate of the economic impact of MRSA on the Canadian healthcare system, which was between $54 to $110 million/year, is over a decade old[8]. The landscape of *S. aureus* infections continues to evolve as new practices have helped to suppress healthcare-associated cases while community-associated cases continue to rise, and we are becoming more aware and tracking possible zoonotic, livestock-associated disease[4].

Mastitis is an inflammatory disease in cattle that puts animal health, milk production, and the economic potential of farmers at risk. In general, this multifactorial disease occurs when infective bacteria, typically belonging to a few representative groups, are able to colonize the animal's mammary gland. The most notorious among the causative agents of mastitis is *Staphylococcus aureus*, a species that is considered a top priority by Canadian farmers and veterinarians[9]; however, other organisms such as *Streptococcus* spp. are common causes of the disease.

The Canadian dairy industry contributes nearly $20 billion per year to the GDP, and based on farm cash receipts it ranks second in the agricultural sector[10]. A 2014 survey of Canadian Dairy industry stakeholders, including ~700 producers (68% of the respondents), agreed that among major animal health concerns, bacterial mastitis should be considered second only to lameness[9]. The survey reflects the economic and health burden caused by mastitis: nationwide dairy producers lose ~$300 million/year to this disease[12]. A recent study in the United States suggested that the average direct and indirect costs of mastitis amount to $444 USD ($575 CAD/case)[13].

Despite a recent push, including legislation, to minimize the use and misuse of antibiotics, the current rates of infection necessitate treatment to spare economic losses and potentially fatal consequences. There is a perpetual need for new and more effective drugs to combat bacterial infections. In Canada, expenditures on antimicrobials totaled $786 million in 2014[14]. Notably, antimicrobial use in animals was 1.7-fold higher than in humans, and an impressive 1.5 million kilograms of active antimicrobial ingredients were employed to prevent and treat disease.

*C. albicans* is a common resident of human mucosa that is responsible for millions of superficial infections every year[15]. Systemic fungal infections caused by *C. albicans* are estimated to cause >400,000 life-threatening infections/year worldwide[16]. In the United States, a 20-year old estimate for the cost of hospitalizations due to candidiasis was $1.7 billion/year with the annual total cost of fungal infections reaching $2.6 billion[17].

The prevalence of antimicrobial resistant pathogens combined with a decades-long lag in first-in-class antibiotic discoveries, has prompted a renaissance in the research and development of once disregarded drug candidates. This includes a renewed interest in antimicrobial peptides (AMPs), which are broadly defined by their amphipathic nature and ability to rapidly disrupt bacterial membranes. Indeed, naturally occurring AMPs evolved as broad-spectrum antibiotics that now participate in the innate immune system of animals. A more accurate categorization of these small molecules as host defense peptides (HDPs) underscores their multifaceted indirect mechanisms of protection against pathogens. Structure-activity relationship (SAR) studies on the human HDP cathelicidin LL-37 provide pre-eminent examples of translating an evolved antimicrobial capacity to drug discovery and development[18]. Structure-based design and screening efforts have resulted in a number of LL-37-based peptides with improved antimicrobial activity against drug resistant pathogens. A collection of synthetic antimicrobial and anti-biofilm peptides (SAAPs) were recently designed based on LL-37 and inhibit a number of ESKAPE pathogens. In particular, one named SAAP-148 is able to clear MRSA and *Acinetobacter baumannii* from in vivo murine and ex vivo human skin models of infection[19-22]. While formulations for specific indications remain a challenge for these peptides[23], continued identification, characterization, and optimization efforts via SAR studies will help to build a reservoir of potential AMPs that meet our urgent needs.

There are a number of bacterial small molecules that act in consort with the antibiotic and immunomodulatory activities of LL-37. These molecules may represent an understudied source of molecules to combat AMR pathogens. The phenol-soluble modulins (PSMs) are a family of staphylococcal peptides shown to synergize with LL-37 to kill bacteria[24], though they are best-known as *S. aureus* virulence factors[25]. Notably, the PSMs possess antimicrobial activity and activate the innate immune system[24,26,27]. Two *S. epidermidis* α-type PSMs, PSMγ (also known as the δ-toxin) and PSMδ, inhibit selected *S. aureus* and Group A *Streptococcus* (GAS)[24]. The potential protective role assigned to *S. epidermidis* PSMγ is supported by its detection on human skin, co-localization with HDPs in neutrophil extracellular traps in vitro, and the provision of protection against a murine GAS infection model[26]. Similar to LL-37, the PSMs are short amphipathic peptides that adopt α-helical structures[28,29]. While the PSMs are known for hemolytic[30], cytotoxic[31], and inflammatory activities[32], some members appear to possess modest antibacterial activities[27,30,33-40] and a capacity to reduce the population of persister cells in populations of bacteria treated with conventional antibiotics[41,42]. Recently, a library of synthetic PSMα-inspired peptides was constructed and one resultant molecule, named zp3, was active against *E. coli* and showed reduced cytotoxicity against eukaryotic cells[43]. Accordingly, the sequence diversity of PSMs, a family with hundreds of unique members, merit a systematic investigation as potential AMPs.

There is a clear need for new and alternative drugs to treat and prevent bacterial and fungal infections in animals.

SUMMARY

The staphylococcal δ-toxins possess relatively weak cyto- and hemolytic activity but share many characteristics with other PSM family members and the antimicrobial core of LL-37. A small but extensible staphylococcal δ-toxin inspired peptide library was screened, and resulted in the discovery of an antibacterial peptide capable of killing MRSA and related pathogens. The discovery, optimization, and characterization of a series of 17 amino acid peptides inspired by the δ-toxin of *S. auricularis* is described herein. The most potent of the AMPs, named STIP3-29, inhibits a number of pathogens at concentrations between 850 nM (1.56 µg/mL) to 3.3 µM (6.25 µg/mL), and is capable of controlling MRSA infections in a human three-dimensional skin model.

An aspect includes an antimicrobial peptide having an amino acid sequence: TVX$_1$X$_2$LVX$_3$WILX$_4$X$_5$X$_6$X$_7$X$_8$FX$_9$ (SEQ ID NO: 32), wherein X1 is selected from G, K, A, R, and Z; X2 is selected from G, K, A, F, and V; X3 is selected from K, R, and Z; X4 is selected from D, A, K, N, R, and Z; X5 is selected from T, V, W, and A; X6 is selected from V and F; X7 is selected from K and A; X8 is selected from K, R, and Z; and X9 is selected from A, I, K, and W; wherein Z=L-ornithine; wherein X2 and X5 are not both V; and wherein the C-terminal residue is unmodified or amidated; or conservatively substituted variants thereof having antimicrobial activity.

In an embodiment, the C-terminal residue is amidated.

In an embodiment, the carboxy terminus is unmodified.

In an embodiment, the peptide has antibacterial activity against one or more of *Staphylococcus* spp. *Streptococcus* spp., *Enterococcus* spp., *Micrococcus* spp., *Escherichia* spp., *Acinetobacter* spp., *Klebsiella* spp., *Mannheimia* spp., *Pseudomonas* spp., *Pasteurella* spp., and *Mycoplasma* spp.

In an embodiment, the peptide has antibacterial activity against one or more *Staphylococcus* spp. selected from the group consisting of *S. aureus, S. epidermidis, S. pseudintermedius, S. auricularis, S. equorum, S. scuri,* and *S. pseudintermedius*.

In an embodiment, the *Staphylococcus* spp. is a methicillin-resistant *S. aureus* (MRSA).

In an embodiment, X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W.

In an embodiment, the antimicrobial peptide has antifungal activity against one or more of *Candida* spp., *Saccharomyces* spp. and *Kodamae ohmeri*.

In an embodiment, the antimicrobial peptide has antifungal activity against one or more *Candida* spp. selected from the group consisting of *C. albicans, C. duobushaemulonii, C. haemulonii, C. krusei,* and *C. lusitaniae*.

In an embodiment, X1 is selected from G, K, and A; X2 is selected from G, K, F, and A; X3 is K; X4 is selected from D, A, K, and N; X5 is selected from T, V, and A; X6 is V; X7 is selected from K and A; X8 is K; X9 is A.

In an embodiment, the antimicrobial peptide has antibacterial activity against *Mannheimia* spp., optionally *M. haemolytica*.

In an embodiment, X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W.

In an embodiment, the peptide has an amino acid sequence selected from the group consisting of:

| | |
|---|---|
| TVGGLVKWILDTVKKFA; | (SEQ ID NO: 1) |
| TVGGLVKWILATVKKFA; | (SEQ ID NO: 2) |
| TVGGLVKWILKTVKKFA; | (SEQ ID NO: 3) |
| TVGGLVKWILNTVKKFA; | (SEQ ID NO: 4) |
| TVGGLVKWILDTVKKFI; | (SEQ ID NO: 5) |
| TVGGLVKWILDTVKKFW; | (SEQ ID NO: 6) |
| TVGGLVKWILDTVKKFK; | (SEQ ID NO: 7) |

TVGVLVKWILDTVKKFA; (SEQ ID NO: 8)

TVGGLVKWILDVVKKFA; (SEQ ID NO: 9)

TVGGLVKWILDVVVKKFA; (SEQ ID NO: 10)

TVGGLVKWILDTFKKFA; (SEQ ID NO: 11)

TVGGLVKWILAAVKKFA; (SEQ ID NO: 12)

TVGGLVKWILKAVKKFA; (SEQ ID NO: 13)

TVKGLVKWILNVVKKFA (SEQ ID NO: 14)

TVAGLVKWILATVKKFA; (SEQ ID NO: 15)

TVKGLVKWILATVKKFA; (SEQ ID NO: 16)

TVDGLVKWILATVKKFA; (SEQ ID NO: 17)

TVKKLVKWILKTVKKFA; (SEQ ID NO: 18)

TVKALVKWILKTVAKFA; (SEQ ID NO: 19)

TVRALVKWILRTVAKFA; (SEQ ID NO: 20)

TVKALVKWILKTVAKFW; (SEQ ID NO: 21)

TVXALVXWILXTVAXFA, where X is L-ornithine; (SEQ ID NO: 22)

TVRALVRWILRTVARFA; (SEQ ID NO: 23)

TVKFLVKWILKVVVAKFA; (SEQ ID NO: 25)

TVGGLVKWILDTVKKFA-NH₂; (SEQ ID NO: 27)

TVGGLVKWILATVKKFA-NH₂; (SEQ ID NO: 28)

TVGGLVKWILKTVKKFA-NH₂; (SEQ ID NO: 29)

TVKGLVKWILNVVKKFA-NH₂; and (SEQ ID NO: 30)

TVKALVKWILKTVAKFW-NH₂. (SEQ ID NO: 31)

In an embodiment, the peptide has an amino acid sequence selected from the group consisting of SEQ ID NO: 14, SEQ ID NO: 29, and SEQ ID NO: 30.

In an embodiment, the peptide comprises a D-amino acid, optionally X4 is a D-amino acid.

In an embodiment, the peptide consists of D-amino acids.

Also described herein are two additional STIPs, STIP8 and STIP9, identified in S. condimenti and S. pettenkoferi, respectively, and derivatives thereof with antimicrobial activity. Accordingly further aspects include antimicrobial peptides having an amino acid sequence selected from TVKSFVNLILDTVKKYAK (SEQ ID NO: 84); TVKSFVNLILKTVKKYAK (SEQ ID NO: 85); TVKSFVNLILKTVKKYAK-NH2 (SEQ ID NO: 86); TVTKFVKLIAETVKKFTK (SEQ ID NO: 87); TVTKFVKLIAKTVKKFTK (SEQ ID NO: 88); and TVTKFVKLIAKTVKKFTK-NH2 (SEQ ID NO: 89).

Another aspect includes a composition comprising an antimicrobial peptide described herein and a carrier.

In an embodiment, the carrier is a pharmaceutically acceptable carrier.

Another aspect includes a method of inhibiting or preventing the growth of a microorganism, the method comprising contacting the microorganism with an effective amount of a peptide described herein, or a composition described herein, thereby inhibiting or preventing the growth of the microorganism.

A further aspect includes a method for treating a microbial infection caused by a microorganism in a subject in need thereof, the method comprising administrating an effective amount of a peptide described herein or a composition described herein to a subject in need thereof, thereby treating the microbial infection.

In an embodiment, the microbial infection is a skin infection.

In an embodiment, the peptide is administered topically.

In an embodiment, the microorganism is S. aureus, optionally MRSA, and the peptide has an amino acid sequence of SEQ ID NO: 32 wherein X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W, optionally the peptide has an amino acid sequence selected from SEQ ID NOs: 3, 6, 9, 12, 13, 14, 15, 19, 20, 21, 23, 28, 29, 30, and 31.

In an embodiment, the microorganism is S. aureus, optionally MRSA, and the peptide has an amino acid sequence selected from SEQ ID NOs: 6, 13, 14, 15, 20, 21, 23, 28, 29, and 30.

In an embodiment, the microorganism is a yeast, optionally a Candida species, and peptide has a sequence of SEQ ID NO: 32, wherein X1 is selected from G, K, and A; X2 is selected from G, K, F and A; X3 is K; X4 is selected from D, A, K, and N; X5 is selected from T, V, and A; X6 is V; X7 is selected from K and A; X8 is K; X9 is A, optionally the peptide is selected from SEQ ID NOs: 3, 4, 13, 14, 15, 16, 17, 18, 19, 25, 27, 28, 29, and 30.

In an embodiment, the microorganism is C. albicans, and the peptide is selected from SEQ ID NOs: 3, 4, 14, 16, 17, 28, and 29.

In an embodiment, the microorganism is M. haemolytica, and the peptide has a sequence of SEQ ID NO: 32, wherein X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W, optionally the peptide is selected from SEQ ID NOs: 3, 13, 16, 18, 19, 21, 22, 23, 28, 30, and 31.

In an embodiment, the microorganism is a bacteria or yeast, optionally selected from the group consisting of S. aureus, S. pseudintermedius, M. luteus, S. agalactiae, S. canis, S. dysagalactiae, S. equi, S. zooepidermicus, M. haemolytica, C. albicans, C. duobushaemulonii, C. haemulonii, C. krusei, C. lusitaniae, K. ohmeri, and S. cerevisiae.

In an embodiment, the microorganism is a methicillin resistant S. aureus (MRSA).

In an embodiment, the C-terminal residue is amidated.

In an embodiment, the peptide has an amino acid sequence of SEQ ID NO: 29.

In an embodiment, the peptide comprises one or more D-amino acids, optionally the peptide consists of D-amino acids.

In an embodiment, the peptide is selected from SEQ ID NOs: 84-89.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Further objects, features and advantages of the disclosure will become apparent from the following detailed description taken in conjunction with the accompanying figures showing illustrative embodiments of the disclosure, in which:

FIG. 1A-1F show the results of preliminary testing of STIP peptides. Panel 1A is a schematic showing the primary sequences of seven peptides (STIP1: SEQ ID NO: 41; STIP2: SEQ ID NO: 46; STIP3: SEQ ID NO: 48; STIP4: SEQ ID NO: 52; STIP5: SEQ ID NO: 56; STIP6: SEQ ID NO: 58; STIP7: SEQ ID NO: 63) evaluated as antibiotics. Two arrows indicate SspA cleavage sites that are conserved in six of the seven peptides. Panel 1B shows the results of a spot-on-lawn assay showing the inhibition of M. luteus by 50 μg of each peptide alone or upon treatment with SspA. Labels on the left panel indicate the position that each peptide was spotted on adjacent M. luteus plates. The opacity in the ΔPSMa1 (labelled α; IIAGIIK-FIKGLIEKFTGK; residues 3-21 of SEQ ID NO: 33) peptide is the result of precipitation, which is less prominent after SspA treatment. Panel 1C shows the results of a spot-on-lawn assay showing inhibition of S. aureus by 50 μg of each peptide alone or upon treatment with SspA. The order of peptide spotting above and below the dashed line are constant. A single peptide mixture derived from STIP3 was capable of inhibiting the growth of S. aureus. Panel 1D is a schematic showing the sequences of four possible STIP3 products of complete and incomplete SspA cleavage. Panel 1E shows the results of spot-on-lawn assays showing inhibition of S. aureus by SspA:STIP3 reaction products and pairwise combinations thereof (above the dashed line). The asterisk shows weak activity of the four-peptide mixture. Panel 1F shows the results of a spot-on-lawn assay used to evaluate the antibiotic activity of single site alanine variants of STIP3-1. Sites that tolerated the substitution are labeled.

FIG. 6A-6C shows the results of experiments to evaluate the effects of selected peptides on eukaryotic cells. Panel 6A is a graph showing the results of a three-dimensional NHEK skin model of MRSA infection and AMP treatment. The skin model was infected at a density of $7 \times 10^3$ CFU/mL (measurement confirmed with n=4 tissues), the MRSA population on untreated tissues expanded by 4-log units to $9 \times 10^7$ CFU/mL (n=4) whereas tissues treated with 25 μg/mL (n=6) did not support the expansion of MRSA with an average bacterial density of $6 \times 10^3$ CFU/mL. Panel 6B is a graph showing the cytotoxicity of selected peptides measured against HeLa cells (n=3). Titrations of δ-toxin, STIP3-1, STIP3-29 and D-STIP3-29 were performed between 1.56 and 200 μg/mL. The datasets were fit to non-linear dose-response curves, which are drawn as solid lines. Panel 6C is a bar graph showing relative hemolytic activity of S. auricularis δ-toxins and STIPs measured using sheep's blood. Normalized values (%) are reported based on complete lysis achieved using Triton X-100 treatments.

DESCRIPTION OF VARIOUS EMBODIMENTS

Figure 2:
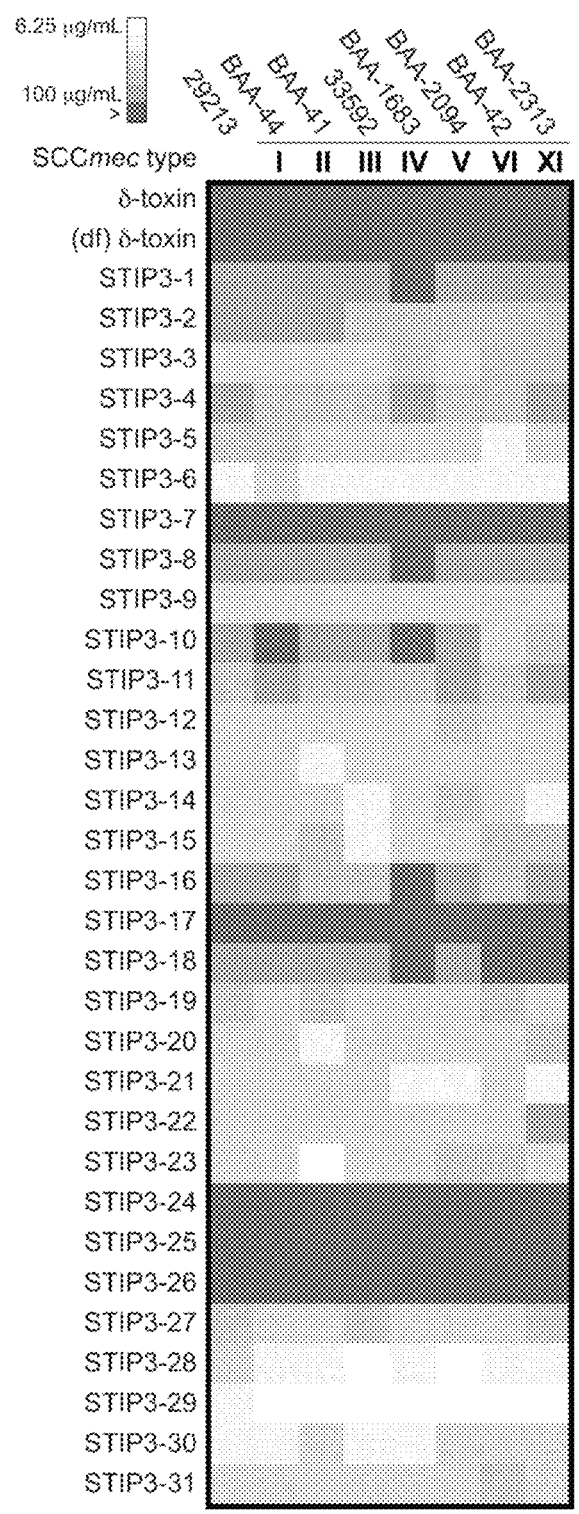
FIG. 2 is a heatmap illustrating the MICs of rationally designed AMPs. The S. auricularis δ-toxin and deformylated (df) form were compared the putative AMPs. MICs were measured between 6.25 μg/mL and 200 μg/mL. The > symbol indicates that no inhibition was observed at the highest concentration of peptide tested: 100 μg/mL for the STIP3 variants or 200 μg/mL for the full-length δ-toxins. The line indicates strains that comprise the ATCC MP-2 MRSA panel.

The following is a detailed description provided to aid those skilled in the art in practicing the present disclosure. Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

Further, the definitions and embodiments described in particular sections are intended to be applicable to other embodiments herein described for which they are suitable as would be understood by a person skilled in the art. For example, in the following passages, different aspects of the disclosure are defined in more detail. Each aspect so defined may be combined with any other aspect or aspects unless clearly indicated to the contrary. In particular, any feature described herein may be combined with any other feature or features described herein.

General Definitions

As used herein, the following terms may have meanings ascribed to them below, unless specified otherwise. However, it should be understood that other meanings that are known or understood by those having ordinary skill in the art are also possible, and within the scope of the present disclosure. In the case of conflict, the present specification, including definitions, will control. In addition, the materials, methods, and examples are illustrative only and not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated.

The term "about" as used herein may be used to take into account experimental error and variations that would be expected by a person having ordinary skill in the art. For example, "about" may mean plus or minus 10%, or plus or minus 5%, of the indicated value to which reference is being made.

As used herein the singular forms "a", "an", and "the" include plural references unless the context clearly dictates otherwise.

The phrase "and/or", as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, in certain methods described herein that include more than one step or act, the order of the steps or acts of the method is not necessarily limited to the order in which the steps or acts of the method are recited unless the context indicates otherwise.

II. Peptides

Delta toxins (also known as PSMdelta, delta hemolysin, or delta-lysin) are phenol soluble modulins (PSMs). PSMs are a family of short amphipathic staphylococcal peptides that adopt α-helical structures, PSMα and δ-toxin being two examples of PSMs.

The inventors herein show that staphylococcal toxins inspired peptides (STIPs) based on delta toxin from *S. auricularis* display antimicrobial activity against a range of microorganisms including, for example, pathogenic bacteria such as *S. aureus* and pathogenic yeast such as *C. albicans*. Also described herein are two additional STIPs, STIP8 and STIP9, identified in *S. condimenti* and *S. pettenkoferi*, respectively, and derivatives thereof with antimicrobial activity.

Accordingly, described herein are antimicrobial peptides having an amino acid sequence TVX$_1$X$_2$LVX$_3$WILX$_4$X$_5$X$_6$X$_7$X$_8$FX$_9$ (SEQ ID NO: 32), wherein X1 is selected from G, K, A, R, and Z; X2 is selected from G, K, A, F, and V; X3 is selected from K, R, and Z; X4 is selected from D, A, K, N, R, and Z; X5 is selected from T, V, W, and A; X6 is selected from V and F; X7 is selected from K and A; X8 is selected from K, R, and Z; X9 is selected from A, I, K, and W; wherein Z=L-ornithine; wherein X2 and X5 are not both V; and wherein the final (i.e. C-terminal) residue is unmodified or amidated; or variants thereof having antimicrobial activity.

Reference to a "peptide described herein", a "peptide of the disclosure", an "antimicrobial peptide described herein" is intended to refer to an antimicrobial peptide having an amino acid sequence of SEQ ID NO: 32, which was derived from residues 8-24 of delta toxin from *S. auricularis* (STIP3-1; SEQ ID NO: 1) and then further modified, including without limitation, peptides having amino acid sequences of SEQ ID NOs: 1-23, 25, and 27-31, and variants thereof having antimicrobial activity.

Variants contemplated herein include functional variants, and include, but are not limited to, amino acid substitutions e.g. conservative amino acid substitutions, incorporating D-amino acids, unnatural amino acids, modified amino acids and/or their derivatives, and modification of the N- or C-terminus of the peptide. It is possible to produce variants for various purposes such as for increasing solubility, enhancing therapeutic or preventative efficacy, enhancing stability or increasing resistance to proteolytic degradation. Such variants are expected to exhibit modified functional activity (for example, antimicrobial peptides having increased antimicrobial activity, decreased cytotoxic activity against mammalian cells and/or decreased hemolytic activity, antimicrobial peptides having increased stability, and/or antimicrobial peptides having an altered antimicrobial spectrum such as being specific for one or more pathogenic species). Variants do not include V2A, L5A, V6A, K7A, W8A, I9A, L10A, or F16A substitutions of SEQ ID NO: 1.

Variants may include conservative amino acid substitutions. A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue or non-natural amino acid in place of a non-derivatized residue provided that such polypeptide displays the requisite activity.

Examples of incorporating natural and unnatural amino acids and derivatives during peptide synthesis include, but are not limited to, use of ornithine, and/or D isomers of amino acids (D-amino acids). In an embodiment, the unnatural amino acid is ornithine, optionally ornithine may be substituted for lysine. In an embodiment, the peptide comprises one or more D-amino acids, optionally, the peptide consists of D-amino acids.

Examples of variants comprising modification to the N- or C-terminus include N-terminal acetylation and C-terminal amidation. As shown herein, C-terminal amidation generally results in a decrease in MIC (i.e. increases antimicrobial activity). Accordingly, in an embodiment, the C-terminal residue of the antimicrobial peptide is amidated. Also shown herein, C-terminal amidation may result in increased cytotoxicity of mammalian cells or hemolytic activity. Accordingly, in another embodiment, the C-terminal residue of the antimicrobial peptide is unmodified.

In an embodiment, the peptides described herein may be resistant to proteolysis, for example SspA proteolysis. Without wishing to be bound by theory, antimicrobial peptides of SEQ ID NO: 32 wherein X4 is not acidic (i.e. is not aspartic acid (D) or glutamic acid (E)), or wherein X4 is a D-amino acid, may be resistant to proteolysis for example SspA proteolysis and accordingly may exhibit increased stability. Specific incorporation of D-amino acids or inversion of the entire peptide's chirality can provide resistance to proteolysis for example SspA proteolysis. Accordingly, in an embodiment, the antimicrobial peptide has a sequence of SEQ ID NO: 32, wherein X4 is not D. In another embodiment, the antimicrobial peptide has a sequence of SEQ ID NO: 32, wherein X4 is a D-amino acid. In a further embodiment, the antimicrobial peptide of SEQ ID NO: 32 comprises or consists of D-amino acids.

As used herein, the term "antimicrobial" refers to the ability to kill or inhibit the growth of one or more microorganisms (e.g. bacteria, yeast or filamentous fungi) and in particular pathogens and opportunistic causative agents of disease in humans, companion animals, and livestock. The antimicrobial peptide can be, for example, an antibacterial or antifungal peptide. An antimicrobial can act to inhibit growth or reproduction of a microorganism (e.g. bacteriostatic) or can kill the microorganism (e.g. bacteriocidal). As used herein, peptides described as having "antimicrobial activity" have a minimum inhibitory concentration (MIC) of 100 μg/ml or less against a microorganism selected from a staphylococcal species (*S. aureus* (including MRSA), *S. pseudintermedius*, *S. auricularis*, *S. epidermidis*, *S. equorum*, and *S. scuri*), a streptococcal species (*S. agalactiae*, *S. canis*, *S. dysagalactiae*, *S. equi*, and *S. zooepidermicus*), *Micrococcus luteus*, *Enterococcus faecalis*, *Mannheimia haemolyticaa*, a *Candida* species (*C. albicans*, *C. duobushaemulonii*, *C. haemulonii*, *C. krusei*, and *C. lusitaniae*), *Kodamae ohmeri*, and *S. cerevisiae*. Optionally, an antimicrobial peptide may have a MIC of 50 μg/ml or less, 25 μg/ml or less, 12.5 μg/ml or less, 6.25 μg/ml or less, 3.13 μg/ml or less, or 1.56 μg/ml or less against a selected microorganism.

In an embodiment, the antimicrobial peptide is an antibacterial peptide. As used herein, the terms "bacteria" or "bacterial" relate to a large domain of prokaryotic microorganisms. Bacteria may include, without limitation, Gram positive bacteria such as *Staphylococcus* spp., *Streptococcus* spp., *Enterococcus* spp. and *Micrococcus* spp.; Gram negative bacteria such as *Escherichia* spp., *Acinetobacter* spp., *Klebsiella* spp., *Mannheimia* spp., *Pseudomonas* spp., *Pasteurella* spp.; and bacterial species lacking a cell wall, such as *Mycoplasma* spp.

In an embodiment, the antimicrobial peptide has antibacterial activity against *Staphylococcus* spp. including, without limitation *S. aureus*, *S. epidermidis*, *S. pseudintermedius*, *S. auricularis*, *S. equorum*, *S. scuri*, and *S. pseudintermedius* (including clinical human isolates SPC001, SPC002, SPC020$^{52}$, and clinical canine isolates MSSP42, MRSP16, MRSP24). In an embodiment, the peptide has antibacterial activity against *Streptococcus* spp., including *S. agalactiae*, *S. canis*, *S. dysagalactiae*, *S. equi*, and *S. zooepidermicus*.

In an embodiment, the antimicrobial peptide has antibacterial activity against bacteria selected from *S. aureus*, *S. epidermidis*, *S. pseudintermedius*, *S. auricularis*, *S. equorum*, *S. scuri*, and *S. pseudintermedius* (including human isolates SPC001, SPC002, SPC020, and canine isolates MSSP42, MRSP16, MRSP24), *Acinetobacter baumannii*, *E. coli*, *Streptococcus agalactiae*, *Streptococcus canis*, *Streptococcus dysagalactiae*, *Streptococcus equi*, *Streptococcus zooepidermicus*, *Micrococcus luteus* (e.g. strain ATCC 4698), *Enterococcus faecalis* (e.g. strain ATCC 2912), *Mannheimia haemolytica*.

In an embodiment, the antimicrobial peptide has antibacterial activity against strains of microorganisms exhibiting antimicrobial resistance. As used herein, the term "antimicrobial resistance" ("AMR") refers generally to microbial strains that have developed or acquired resistance (non-susceptibility) to at least one antimicrobial agent such an antibiotic or antifungal. Examples of bacterial strains exhibiting AMR include methicillin-resistant *S. aureus* (MRSA) and vancomycin-resistant *S. aureus* (VRSA).

The term "MRSA" refers to *S. aureus* strains that are resistant to methicillin and other beta-lactam antibiotics, historically named due to observed resistance to methicillin. Resistance is mediated by the expression of the resistance gene mecA. MRSA strains may include SCCmec types I-XII, for example type I strains such as BAA-44, type II strains such as BAA-41, type III strains such as 33592, type IV strains such as BAA-1683, type V strains such as BAA-2094, type VI strains such as BAA-42, and type XI strains such as BAA-2313. Methods of identifying MRSA are known in the art, for example broth microdilution testing, cefoxitin disk diffusion test, or a plate containing 6 μg/ml of oxacillin in Mueller-Hinton agar supplemented with 4% NaCl, or molecular detection of the mecA gene. Other detection methods may also be used.

The term "methicillin-sensitive *S. aureus*" ("MSSA") refers to *S. aureus* strains that are sensitive to beta-lactam antibiotics. These include *S. aureus* strain ATCC 29213.

As used herein, the term "antifungal" means killing or inhibiting the growth of fungi, particularly yeast. Yeast include *Candida* spp. such as *C. albicans* (e.g. strains MYA-2876 and Y537), *C. duobushaemulonii* (e.g. strains AR 391, AR 392, and AR 394), *C. haemulonii* (e.g. strains AR 393 and AR 395), *C. krusei* (e.g. strain AR 397), and *C. lusitaniae* (e.g. strain AR 398); *Kodamae ohmeri* (e.g. strain AR 396); and *Saccharomyces* spp. such as *S. cerevisiae* (e.g. strains AR 399 and AR 400).

As used herein, minimum inhibitory concentration (MIC) refers to the lowest peptide concentration that results in no observed microbial growth after an overnight treatment. In an embodiment, the peptide has a MIC of about 100 μg/mL or less, about 50 μg/mL or less, about 25 μg/mL or less, about 12.5 μg/mL or less, about 6.25 μg/mL or less, about 3.13 μg/mL or less, or about 1.56 μg/mL or less. It will be understood that the MIC of a particular peptide varies depending on the microbial species or strain.

Peptides described herein having an amino acid sequence of SEQ ID NO: 32 wherein X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W, may be particularly useful for inhibiting the growth of *S. aureus* strains including MRSA. Accordingly, in an embodiment, the peptide has an amino acid sequence of SEQ ID NO: 32 wherein X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W, optionally the peptide is selected from SEQ ID NOs: 3, 6, 9, 12, 13, 14, 15, 19, 20, 21, 23, 28, 29, 30, and 31, and variants thereof having antibacterial activity against *S. aureus*. In an embodiment, the peptide is C-terminally amidated. In an embodiment, the peptide has an amino acid sequence of SEQ ID NO: 29.

Also shown herein, peptides of SEQ ID NOs: 1, 2, 3, 4, 5, 6, 8, 9, 10, 11, 12, 13, 14, 15, 16, 18, 19, 20, 21, 22, 23, 25, 27, 28, 29, 30, and 31 may be useful for inhibiting the growth of *S. aureus* strains including MRSA. Also shown in the examples, peptides of SEQ ID NOs: 6, 13, 14, 15, 20, 21, 23, 28, 29, and 30 may be particularly useful for inhibiting the growth of *S. aureus* strains including MRSA. Accordingly, in an embodiment the peptide has an amino acid sequence of SEQ ID NOs: 1, 2, 3, 4, 5, 6, 8, 9, 10, 11, 12, 13, 14, 15, 16, 18, 19, 20, 21, 22, 23, 25, 27, 28, 29, 30, and 31, and variants thereof having antibacterial activity against *S. aureus*. In an embodiment, the peptide has an amino acid sequence selected from SEQ ID NOs: 6, 13, 14, 15, 20, 21, 23, 28, 29, and 30 and variants thereof having antibacterial activity against *S. aureus*. In an embodiment, the peptide is C-terminally amidated. In an embodiment, the peptide has an amino acid sequence of SEQ ID NO: 29. In an embodiment, the peptide consists of L-amino acids. In another embodiment, the peptide comprises one or more D-amino acids. In further embodiment, the peptide consists of D-amino acids.

Antimicrobial peptides having an amino acid sequence of SEQ ID NO: 32, wherein X1 is selected from G, K, and A; X2 is selected from G, K, F and A; X3 is K; X4 is selected from D, A, K, and N; X5 is selected from T, V, and A; X6 is V; X7 is selected from K and A; X8 is K; X9 is A, may be particularly useful as antifungal peptides. Accordingly, in an embodiment, the peptide has a sequence of SEQ ID NO: 32, wherein X1 is selected from G, K, and A; X2 is selected from G, K, F and A; X3 is K; X4 is selected from D, A, K, and N; X5 is selected from T, V, and A; X6 is V; X7 is selected from K and A; X8 is K; X9 is A, optionally the peptide is selected from SEQ ID NOs: 3, 4, 13, 14, 15, 16, 17, 18, 19, 25, 27, 28, 29, and 30, and variants thereof having antifungal activities. In an embodiment, the peptide is C-terminally amidated. In an embodiment, the peptide has an amino acid sequence selected from SEQ ID NOs: 14, 29, and 30.

Also shown herein, peptides of SEQ ID NOs: 14 and 29 may be particularly useful for inhibiting the growth of yeast. Accordingly, in an embodiment the peptide has an amino acid sequence of SEQ ID NOs: 14 or 29, and variants thereof having antifungal activity. In an embodiment, the peptide is C-terminally amidated. In an embodiment, the peptide comprises a D-amino acid at position 11 (X4 of SEQ ID NO: 32).

Peptides described herein having an amino acid sequence of SEQ ID NO: 32 wherein X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W, may be particularly useful for inhibiting the growth of *M. haemolytica*. Accordingly, in an embodiment, the peptide has an amino acid sequence of SEQ ID NO: 32 wherein X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W. In an embodiment, the peptide is selected from SEQ ID NOs: 3, 13, 16, 18, 19, 21, 22, 23, 28, 30, and 31, and variants thereof having antibacterial activity against *M. haemolytica*. In an embodiment, the peptide is selected from SEQ ID NOs: 16, 18, 22, and 31.

Further aspects include antimicrobial peptides having an amino acid sequence of TVKSFVNLILDTVKKYAK (SEQ ID NO: 84); TVKSFVNLILKTVKKYAK (SEQ ID NO: 85); TVKSFVNLILKTVKKYAK-NH2 (SEQ ID NO: 86) TVTKFVKLIAETVKKFTK (SEQ ID NO: 87); TVTKFVKLIAKTVKKFTK (SEQ ID NO: 88); and TVTKFVKLIAKTVKKFTK-NH2 (SEQ ID NO: 89).

As shown herein, the peptides described herein have alpha-helical character in 50% (v/v) trifluoroethanol (TFE) and are unstructured in water, and the peptides with the greatest and least alpha-helical content in TFE had a MIC above the highest tested threshold. Accordingly, in an embodiment, the peptide is at least 45% alpha-helical in 50% TFE and unstructured in water, optionally the peptide is between about 45% and 75% alpha-helical in 50% TFE.

The peptides described herein are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). Alternatively, the peptides may be prepared using recombinant protein expression systems or other methods known in the art.

III. Compositions

A further aspect is a composition comprising a peptide described herein and optionally a diluent or carrier. In an embodiment, the composition is for use in inhibiting or preventing the growth of a microorganism.

Suitable diluents or carriers for polypeptides include but are not limited to saline solutions, pH buffered solutions and glycerol solutions or other solutions suitable for stabilizing and/or freezing polypeptides.

In an embodiment, the composition is a pharmaceutical composition comprising any of the peptides disclosed herein, and optionally comprising a pharmaceutically acceptable carrier. The composition may be formulated for use or prepared for administration to a subject using pharmaceutically acceptable formulations known in the art. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. As used herein, the term "pharmaceutically acceptable" means that the carrier, diluent, or excipient is compatible with the other components of the formulation and not substantially deleterious to the recipient thereof. The term "pharmaceutically acceptable" means compatible with the treatment of animals, in particular, humans, livestock, and companion animals.

The compositions described herein can be prepared by per se known methods for the preparation of pharmaceutically acceptable compositions that can be administered to subjects such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

In an embodiment, the pharmaceutical composition is for use in the treatment or prevention of a microbial infection in a subject in need thereof. In an embodiment, the pharmaceutical composition is formulated for topical use.

IV. Methods and Uses

The peptides described herein are found to have antimicrobial activity against a variety of microorganisms including pathogenic bacteria and fungi. Accordingly, an aspect includes a peptide described herein for use in inhibiting or preventing the growth of a microorganism. Another aspect includes a peptide described herein for use in the manufacture of a medicament for inhibiting or preventing the growth of a microorganism. Also provided is use of a peptide described herein for inhibiting or preventing the growth of a microorganism. Also provided herein is a method of inhibiting or preventing the growth of a microorganism, the method comprising contacting the microorganism with an effective amount of a peptide described herein, or composition comprising a peptide described herein, thereby inhibiting or preventing the growth of the microorganism. In an embodiment, the microorganism is a bacterial species. In an embodiment, the microorganism is a fungal species, optionally a yeast species. In an embodiment, the microorganism is a pathogenic microorganism Also shown in the examples, the peptides described herein have antimicrobial activity in a three-dimensional skin model of MRSA infection. Accordingly, an aspect includes a peptide described herein for use in the treatment or prevention of a microbial infection in a subject in need thereof. Another aspect includes a peptide described herein for use in the manufacture of a medicament for the treatment or prevention of a microbial infection in a subject in need thereof. Also provided is use of a peptide described herein for treating or preventing a microbial infection in a subject in need thereof. Also provided herein is a method of treating or preventing a microbial infection in a subject in need thereof, the method comprising administering an effective amount of a peptide described herein to a subject in need thereof, thereby treating the microbial infection.

In an embodiment, the microbial infection is a bacterial infection. In an embodiment the microbial infection is a fungal infection, optionally a yeast infection. In an embodiment, the microbial infection is a skin infection. In an embodiment, the infection is caused by a microorganism selected from the group consisting of *S. aureus, S. pseudintermedius, M. luteus, S. agalactiae, S. canis, S. dysagalactiae, S. equi, S. zooepidermicus, M. haemolytica, C. albicans, C. duobushaemulonii, C. haemulonii, C. krusei, C. lusitaniae, K. ohmeri*, and *S. cerevisiae*. In an embodiment, the infection is a MRSA infection, optionally a skin infection.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. controlled microbial growth), preventing spread of disease, delay or slowing of disease progression, amelioration or palliation of the disease state, and diminishment of the reoccurrence of disease, whether detectable or undetectable. "Treating" and "treatment" can also mean prolonging survival as compared to expected survival if not receiving treatment. In one embodiment, treatment methods comprise administering to a subject a therapeutically effective amount of a peptide described herein, and optionally consists of a single administration, or alternatively comprises a series of administrations.

The term "preventing" or "prevention" as used herein and as understood in the art, means an approach for blocking or halting the development of a condition or disease state such as a microbial infection. "Preventing" and "prevention" as used herein also include prophylactic use or administration.

The term "administered" as used herein means administration of a therapeutically effective dose of a peptide of the disclosure to a cell or subject. The peptides described herein can be administered for example, by topical, parenteral, intravenous, subcutaneous, intramuscular, intracranial, intraventricular, intrathecal, intraorbital, ophthalmic, intraspinal, intracisternal, intraperitoneal, intranasal, aerosol or oral administration. In certain embodiments, the pharmaceutical composition is administered topically.

As used herein, the phrase "effective amount" or "therapeutically effective amount" means an amount effective, at dosages and for periods of time necessary to achieve the desired result. For example, in the context of treating a microbial infection, an effective amount is an amount that achieves a treatment response, for example reduces disease burden, and/or reduces or prevents growth of one or more microbial species, as compared to the response obtained without administration of the compound. The amount of a given compound that will correspond to such an amount will vary depending upon various factors, such as the given peptide, the pharmaceutical formulation, the route of administration, the type of disease or disorder (for example the species or strain of microorganism(s) causing the microbial infection), the identity of the subject or host being treated, and the like, but can nevertheless be routinely determined by one skilled in the art. Effective amounts may vary for example according to the type, location, or extent of the microbial infection, or factors such as the age, sex and weight of the subject.

The term "subject" as used herein includes all members of the animal kingdom including mammals, and suitably refers to humans and bovines. Optionally, the term "subject" includes mammals that have been diagnosed with a microbial infection. In one embodiment, the term "subject" refers to a human having, or suspected of having, a microbial infection. In another embodiment, the term "subject" refers to a bovine having, or suspected of having, a microbial infection, for example a bovine having mastitis.

As shown in the Examples, the antimicrobial peptides described herein may have different properties, for example, a different spectrum of antimicrobial activity (e.g. increased activity against one or more specific microorganism(s)) or decreased cytotoxicity towards mammalian cells.

For example, antimicrobial peptides having an amino acid sequence of SEQ ID NO: 32 wherein X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W, may be particularly useful for inhibiting the growth of S. aureus strains including MRSA. Accordingly, in an embodiment, the microorganism is S. aureus, optionally MRSA, and the peptide has an amino acid sequence of SEQ ID NO: 32 wherein X1 is selected from G, K, A, and R; X2 is selected from G and A; X3 is selected from K and R; X4 is selected from D, N, A, K, and R; X5 is selected from T, V, and A; X6 is V; X7 is selected from K and A; X8 is selected from K and R; and X9 is selected from A and W, or variants thereof having antibacterial activity against S. aureus. In an embodiment, the peptide has an amino acid sequence selected from SEQ ID NOs: 3, 6, 9, 12, 13, 14, 15, 19, 20, 21, 23, 28, 29, 30, and 31, and variants thereof having antibacterial activity against S. aureus. In an embodiment, the peptide is C-terminally amidated. In an embodiment, the peptide as an amino acid sequence of SEQ ID NO: 29.

In another embodiment, the microorganism is S. aureus, optionally MRSA, and the peptide has an amino acid sequence selected from SEQ ID NOs: 1, 2, 3, 4, 5, 6, 8, 9, 10, 11, 12, 13, 14, 15, 16, 18, 19, 20, 21, 22, 23, 25, 27, 28, 29, 30, and 31 and variants thereof having antibacterial activity against S. aureus. Optionally, the peptide has an amino acid sequence selected from SEQ ID NOs: 6, 13, 14, 15, 20, 21, 23, 28, 29, and 30 and variants thereof having antibacterial activity against S. aureus. In an embodiment, the peptide is C-terminally amidated. In an embodiment, the peptide has an amino acid sequence of SEQ ID NO: 29. In an embodiment, the peptide consists of L-amino acids. In another embodiment, the peptide comprises one or more D-amino acids. In further embodiment, the peptide consists of D-amino acids.

Antimicrobial peptides having an amino acid sequence of SEQ ID NO: 32 wherein X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W, may be particularly useful for inhibiting the growth of M. haemolytica. Accordingly, in an embodiment, the microorganism is M. haemolytica, and the peptide has an amino acid sequence of SEQ ID NO: 32 wherein X1 is selected from G, K, R, and Z; X2 is selected from G, K, and A; X3 is selected from K, R, and Z; X4 is selected from A, K, N, R, and Z; X5 is selected from T, V, and A; X6 is V; X7 is selected from K and A; X8 is selected from K, R, and Z; and X9 is selected from A, and W, or variants thereof having antibacterial activity against M. haemolytica. In an embodiment, the peptide has an amino acid sequence selected from SEQ ID NOs: 3, 13, 16, 18, 19, 21, 22, 23, 28, 30, and 31, and variants thereof having antibacterial activity against M. haemolytica. In an embodiment, the peptide has an amino acid sequence selected from SEQ ID NOs: 16, 18, 22, and 31. In an embodiment, the peptide is C-terminally amidated. In an embodiment, the peptide consists of L-amino acids. In another embodiment, the peptide comprises one or more D-amino acids. In further embodiment, the peptide consists of D-amino acids.

Antimicrobial peptides having an amino acid sequence of SEQ ID NO: 32, wherein X1 is selected from G, K, and A; X2 is selected from G, K, F and A; X3 is K; X4 is selected from D, A, K, and N; X5 is selected from T, V, and A; X6 is V; X7 is selected from K and A; X8 is K; X9 is A, may be particularly useful as antifungal peptides. Accordingly, in an embodiment, the microorganism is a yeast, optionally a Candida species, and the peptide has an amino acid sequence of SEQ ID NO: 32, wherein X1 is selected from G, K, and A; X2 is selected from G, K, F, and A; X3 is K; X4 is selected from D, A, K, and N; X5 is selected from T, V, and A; X6 is V; X7 is selected from K and A; X8 is K; X9 is A, and variants thereof having antifungal activity. In an embodiment, the peptide is selected from SEQ ID NOs: 3, 4, 13, 14, 15, 16, 17, 18, 19, 25, 27, 28, 29, and 30. In an embodiment, the peptide has an amino acid sequence selected from SEQ ID NOs: 14, 29, and 30. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In another embodiment, the microorganism is C. albicans, and the peptide is selected from SEQ ID NOs: 1, 3, 4, 6, 7, 9, 10, 11, 13, 14, 15, 16, 17, 18, 25, 27, 28, 29, and 30, and variants thereof having antifungal activity against C. albicans. Optionally, the peptide has an amino acid sequence selected from SEQ ID NOs: 3, 4, 14, 16, 17, 28, and 29, and variants thereof having antifungal activity against C. albicans. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is C. duobushaemulonii, and the peptide is selected from SEQ ID NOs: 13, 14, 18, 19, 29, and 30, and variants thereof having antifungal activity against *C. duobushaemulonii*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is *C. haemulonii*, and the peptide is selected from SEQ ID NOs: 28 and 30, and variants thereof having antifungal activity against *C. haemulonii*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is *C. krusei*, and the peptide is selected from SEQ ID NOs: 1, 2, 3, 4, 5, 6, 7, 8, 9, 11, 12, 13, 14, 15, 16, 17, 18, 19, 21, 22, 27, 28, 29, and 30, and variants thereof having antifungal activity against *C. krusei*. Optionally the peptide is selected from SEQ ID NOs: 1, 2, 14, 29, 30 and variants thereof having antifungal activity against *C. krusei*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is *C. lusitaniae*, and the peptide is selected from SEQ ID NOs: 1, 3, 4, 5, 6, 7, 8, 9, 11, 12, 13, 14, 15, 16, 17, 18, 19, 21, 22, 23, 24, 25, 26, 27, 28, 29, and 30, and variants thereof having antifungal activity against *C. lusitaniae*. Optionally, the peptide is selected from SEQ ID NOs: 14, 19, 21, 29, and 30, and variants thereof having antifungal activity against *C. lusitaniae*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is *Kodamae ohmeri*, and the peptide is selected from SEQ ID NOs: 2, 14, 15, 16, 27, 28, 29, and 30 and variants thereof having antifungal activity against *Kodamae ohmeri*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

In an embodiment, the microorganism is *S. cerevisiae*, and the peptide is selected from SEQ ID NOs: 1, 2, 3, 4, 5, 6, 7, 8, 9, 11, 12, 13, 14, 15, 16, 17, 18, 19, 22, 23, 24, 25, 26, 27, 28, 29, and 30, and variants thereof having antifungal activity against *S. cerevisiae*. Optionally, the peptide is selected from SEQ ID NOs: 1, 14 and 30, and variants thereof having antifungal activity against *S. cerevisiae*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

Also shown herein, antimicrobial peptides having an amino acid sequence of SEQ ID NO: 29 are particularly useful for inhibiting the growth of various species of bacteria and yeast and for controlling MRSA infection in a skin model. Accordingly, in an embodiment, the peptide has an amino acid sequence of SEQ ID NO: 29 and the microbial species is a bacterial species including staphylococcal species such as *S. aureus* (including MRSA), *S. pseudintermedius*, *S. auricularis*, *S. epidermidis*, *S. equorum*, and *S. scuri*, a streptococcal species such as *S. agalactiae*, *S. canis*, *S. dysagalactiae*, *S. equi*, and *S. zooepidermicus*, other bacterial species such as *Micrococcus luteus*, *Enterococcus faecalis*, and *Mannheimia haemolyticaa*, or a yeast species including *Candida* species such as *C. albicans*, *C. duobushaemulonii*, *C. krusei*, and *C. lusitaniae*, and other yeast species such as *Kodamae ohmeri*, and *S. cerevisiae*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

As shown in the Examples, C-terminal amidation of the peptide may result in decreased MIC, increased cytotoxicity of mammalian cells, and/or increased hemolytic activity. Accordingly, in an embodiment, the C-terminus of the peptide is unmodified. In another embodiment, the C-terminal residue of the peptide is amidated.

As shown in the Examples, the inclusion of D-amino acids may reduce hemolytic activity. Accordingly, in an embodiment, the peptide comprises one or more D-amino acids. In another embodiment, the peptide consists of D-amino acids.

Antimicrobial peptides having an amino acid sequence selected from TVKSFVNLILDTVKKYAK (SEQ ID NO: 84); TVKSFVNLILKTVKKYAK (SEQ ID NO: 85); TVKSFVNLILKTVKKYAK-NH2 (SEQ ID NO: 86); TVTKFVKLIAETVKKFTK (SEQ ID NO: 87); TVTKFVKLIAKTVKKFTK (SEQ ID NO: 88); and TVTKFVKLIAKTVKKFTK-NH2 (SEQ ID NO: 89) may be useful for inhibiting the growth of microorganisms such as, for example, *C. albicans*, *M. luteus*, and/or *M. haemolytica*. Accordingly, in an embodiment, the microorganism is *C. albicans*, *M. luteus*, and/or *M. haemolytica*, and the peptide has an amino acid sequence selected from SEQ ID NOs: 84, 85, 86, 87, 88, and 89, and variants thereof having antibacterial activity against *C. albicans*, *M. luteus*, and/or *M. haemolytica*. In an embodiment, the peptide is C-terminally amidated. In an embodiment, the peptide consists of L-amino acids. In another embodiment, the peptide comprises one or more D-amino acids. In further embodiment, the peptide consists of D-amino acids.

The following non-limiting examples are illustrative of the present disclosure:

EXAMPLES

Example 1

δ-Toxin-Inspired AMP Design and Screen for Antimicrobial Activity

Seven unique δ-toxin peptides from 6 staphylococcal members of the human microbiome were investigated. The primary sequences of the δ-toxins possess regularly spaced acidic amino acids, and SspA, a secreted staphylococcal protease, could be used to cleave the peptides after the acidic residues to afford extensibility to the peptide library while counter screening for this enzyme's ability to cleave and deactivate potential AMPs. Since modest antibiotic activity has been reported from naturally-occurring N-terminally processed forms of PSMα1 and PSMα2[34] and SspA treatments were to be used, the 7 peptides were N-terminally truncated. With the exception of STIP5, the collection of staphylococcal toxins inspired peptides (STIPs) were designed to begin after the first acidic residue in the native sequence (Table 1). Overall, the peptides share between 38 to 95% sequence identity, have predicted isoelectric points between 8.4 and 10.0, possess at least two acidic amino acids, and begin with a pair of hydrophobic residues (FIG. 1A).

To begin to evaluate the antibiotic activity, crude preparations (≥70% purity; Table 1) were deposited on agar surfaces inoculated with bacterial lawns of *M. luteus* ATCC 4698 and *S. aureus* ATCC 29213 (hereafter *S. aureus*). Five of the 7 peptides were capable of inhibiting *M. luteus* when 50 μg was used (FIG. 1B); however, none inhibited the growth of *S. aureus* (FIG. 1C).

A truncated form of PSMα2 from *S. aureus* known to inhibit *M. luteus* was used as a control. The ability of SspA to increase the number of potentially bioactive peptides from the collection was explored. Each peptide was treated with 2 mg/mL of SspA for 5 h at 37° C. before repeating the spot-on-lawn assay. In contrast to the intact peptide, the products from the reaction of SspA and STIP3, a peptide based on the *S. auricularis* δ-toxin, demonstrated antibiotic activity against *S. aureus* (FIG. 1C). The zone of *M. luteus* inhibition observed for the SspA-treated STIP mixture was also ~1.4-fold larger in diameter than the intact peptide. In a separate experiment, LC/MS analysis of SspA-treated samples was performed to confirm that peptide cleavage was occurring at the predicted sites (Table 2). Notably, STIP3 differs from the other peptides in the collection in that it lacks an otherwise conserved SspA-cleavage site at position 7. It was initially rationalized that redundancy in heptapeptide products of SspA-mediated hydrolysis (e.g. the C-terminal fragments of SEQ ID NOs: 44, 55, 57, and 65) would help to identify bioactive fragments, however, the divergent STIP3 sequence yielded the only active mixture against *S. aureus*. Four of the five possible SspA-generated STIP3 products were therefore tested, accounting for a possible missed cleavage (FIG. 1D). It is noteworthy that small cationic fragments of PSMα3, KLFKFFK (SEQ ID NO: 82) and LFKFFK (SEQ ID NO: 83), were previously reported to inhibit *M. luteus* and *Staphylococcus hominis* when 250 to 750 μg were loaded onto paper discs placed on bacteria inoculated on agar surfaces[38]. Here, peptides were plated directly on the agar surface and antimicrobial activity was observed with a 50 μg sample. By testing the four possible products of SspA-mediated STIP3 proteolysis, it was established that the 17-amino acid peptide TVG-GLVKWILDTVKKFA (SEQ ID NO: 1), named STIP3-1, was responsible for the inhibition of *S. aureus* (FIG. 1E). Pairs of SspA cleavage products were not as active as STIP3-1 alone. STIP3-1 is characterized by a missed cleavage site after Asp11 of SEQ ID NO: 1; subsequent SspA digestion experiments confirmed that the protease is able to cleave the bioactive peptide into an inactive mixture (Table 3). Thus, SspA proved to be a useful tool to examine the antimicrobial potential of STIPs and acted (in a time-dependent manner) to counterscreen for AMPs that can be inactivated by this secreted enzyme.

There is no information available for SspA proteolysis of *S. auricularis* δ-toxins in nature. The ability of SspA to cleave both the formyl- and deformylated *S. auricularis* δ-toxin in vitro was examined. Although it has not been explicitly studied in *S. auricularis*, the *S. aureus* δ-toxin occurs in both forms during the exponential and early-stationary phases of growth whereas the formylated peptide is the dominant form in the late stationary phase[44, 45]. Moreover, deformylated peptides were reported as the major constituents of mixed PSM amyloid fibers present in *S. aureus* biofilms[46]. It was observed that the deformylated peptide was susceptible to SspA cleavage in vitro but that formylation protected against proteolysis (Table 3).

Example 2

Improving the Antimicrobial Activity of STIP3-1 Through Rational Design

In order to begin to characterize STIP3-1 and potential sites amenable to modification, an alanine scanning experiment was performed. A total of 16 peptides with single alanine substitutions were assessed to inform on the importance of individual residues to antimicrobial activity. All of the peptides retained some ability to inhibit *M. luteus* whereas only the STIP3-1 variants T1A, G3A, G4A, D11A, T12A, K14A, and K15A of SEQ ID NO: 1 were observed to inhibit *S. aureus* in the spot-on-lawn assay (FIG. 1F); however only the activities of T1A, D11A, T12A and V13A were recapitulated in nutrient broth at concentration as high as 200 μg/mL (~100 μM; Table 4). Next a series of thirty STIP3-1 variants were designed, guided by the aforementioned alanine scan and a previous report that the central α-helical core of the *S. aureus* δ-toxin could be converted into AMP through the inclusion of additional lysine residues[39]. The collection included ten members with single substitutions relative to STIP3-1 and others that incorporated a number of changes that were designed to increase overall and local cationic charge as well as hydrophobic character (Table 5). Each of the STIPs was screened, including STIP3-1 to STIP-31, for antibiotic activity against a methicillin-sensitive *S. aureus* test organism and a panel of 7 MRSA strains defined by distinct SCCmec genotypes (FIG. 2; ATCC MP-2). The incorporation of regularly spaced basic residues to the design, including lysine, arginine, and ornithine, in many cases resulted in 4 to 8-fold improvements to the activity of STIP3-1 variants. Amidation of the peptide's C-terminus also generally resulted in a decrease to the observed MIC with some exceptions (Table 5). Not all substitutions increased antimicrobial activity: the incorporation of more hydrophobic residues in STIP3-24, -25, and -26, for example, resulted in peptides incapable of inhibiting *S. aureus*. The most potent peptide in the collection, STIP3-29, differed from STIP3-1 in that Asp11 was replaced by Lys and the C-terminus was amidated. STIP3-29 inhibited MRSA at 6.25 μg/mL (3.3 μM) and *M. luteus* at 1.56 μg/ml (850 nM), corresponding to 16- and 8-fold improvements, respectively.

Example 3

STIP3-29 is a Bactericidal Peptide

Figure 3:
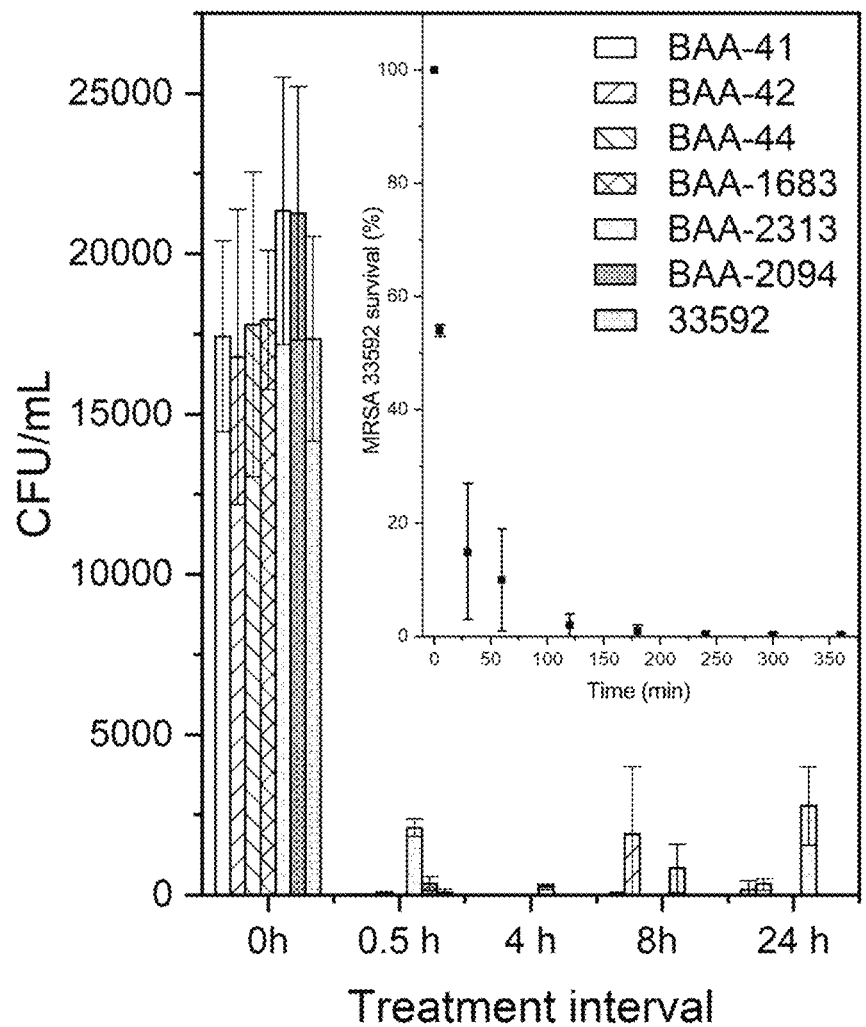
FIG. 3 is a bar graph representing the bactericidal activity of STIP3-29 using a panel of 7 MRSA strains. The rapid time-dependent bactericidal activity of STIP3-29 acting on MRSA ATCC 33592 is inset.

The antibiotic effect of STIP3-29 was bactericidal (FIG. 3). The panel of 7 MRSA strains was treated with 12.5 μg/mL STIP3-29 (2-fold MIC), which showed the ability to kill ~99% of the treated bacteria within the first 4 hours. After a 24 h treatment period, some of the MRSA strains, in particular, BAA-42 and BAA-2313 demonstrated a capacity to survive the treatments; however, the cell counts, which were between 20 to 270 CFU/mL for these strains, were $10^4$ to $10^5$ fold lower than untreated controls. Taken together, the data suggest a rapid mode of action. Some proportion of bacterial cells escaped treatment, remaining dormant. Indeed, strain-dependent persister cells, capable of escaping a variety of therapeutic agents, have been described for *S. aureus*[47].

Example 4

Figure 4:
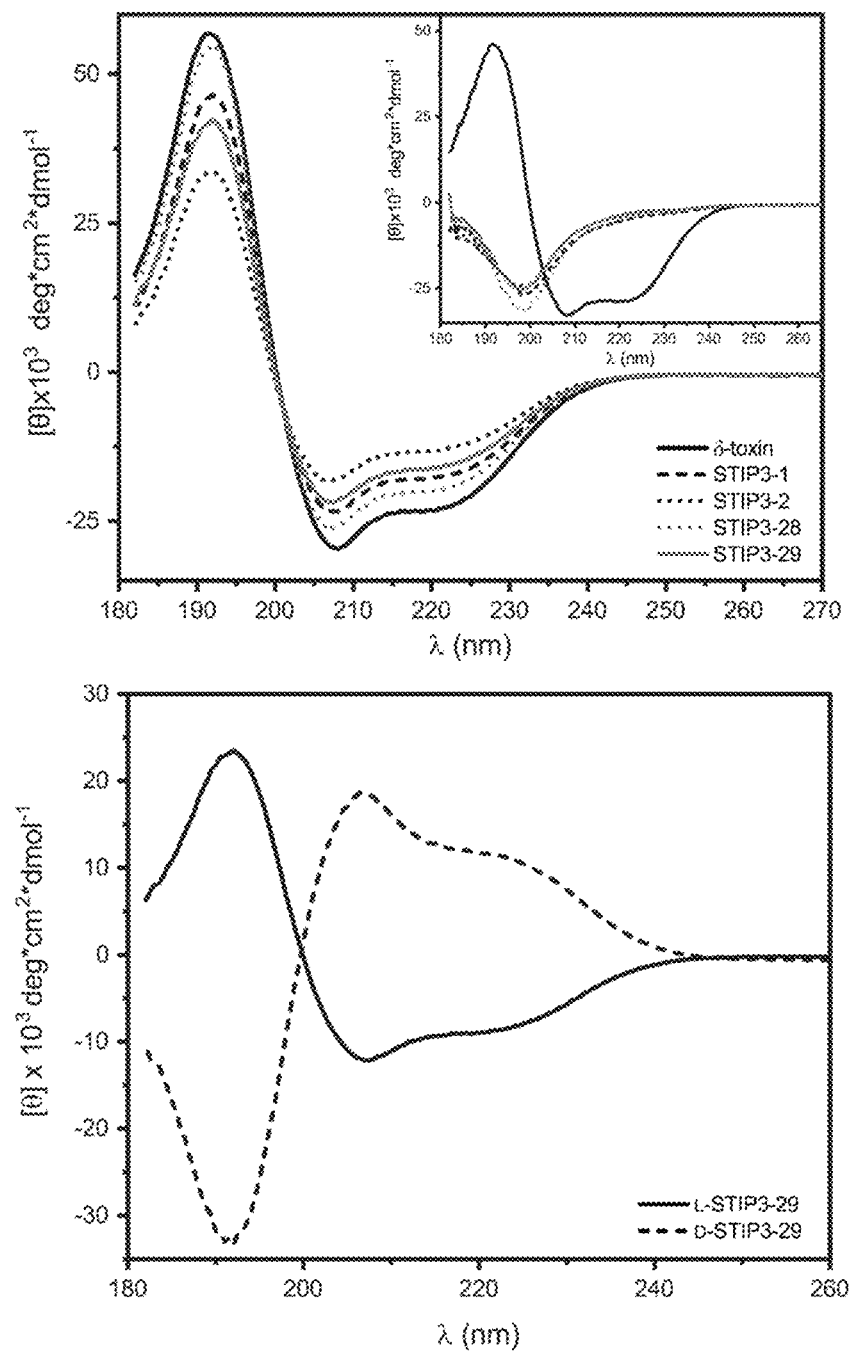
FIG. 4 shows the CD spectra of a subset of STIP3 peptide variants. The top panel shows representative CD spectra of STIP3 peptide variants and the S. auricularis δ-toxin. Spectra of the peptides dissolved in 50% (v/v) TFE show the characteristic absorbance bands of α-helices. Inset shows the spectra show that the same STIP3 peptides are unstructured in water whereas the formylated δ-toxin is not. The bottom panel shows a comparison of the CD spectra collected for L (solid line) and D-enantiomer (dashed line) of STIP3-29.

Preliminary Biophysical Characterization of STIPs and Structure-Activity Relationships The δ-toxins and the PSMs are characterized as α-helical peptides that form amyloid fibers[48]. Although the propensity of individual peptides to form amyloids is correlated to their cytotoxicity[49], the amyloid form is not directly implicated in cell membrane disruption[50]. For the δ-toxins, SAR studies have demonstrated that helicity is a major determinant of binding to phospholipid bilayers[51]. CD spectroscopy was used to investigate the secondary structure of a subset of peptides within the collection (FIG. 4A, Table 5). The STIP variants adopted α-helical forms in 50% (v/v) trifluoroethanol (TFE), though unlike the full-length *S. auricularis* δ-toxin, they were unstructured in water. A cursory inspection of peptide α-helicity in TFE versus the MIC values suggested a non-linear correlation. Specifically, peptides characterized by the greatest and least α-helical content in TFE had MICs above the highest tested threshold.

In order to further test the relationship between peptide structure and activity, three additional STIP3-29 variants were studied: (i) an all D-enantiomer (D-STIP3-29), and peptides that included either (ii) a single D-Lys residue (STIP3-29-D1) at position 11 of SEQ ID NO: 29, or (iii) three D-Lys residues (STIP3-29-D3) at positions 7, 11, and 15 of SEQ ID NO: 29 (FIG. 4B). The introduction of one or three D-Lys residues to disrupt peptide helicity, increased the MIC by 4- and greater than 16-fold relative to STIP3-29, respectively. The D-enantiomer, which maintained similar helical character, was just as active as the L-enantiomer (FIG. 4B). Overall, the results suggest, without wishing to be bound by theory, that structural plasticity is an important determinant of AMP activity but that the targeted interaction is not stereospecific.

Example 5

Phenotypic Evaluation of STIP3-29 Interaction with Live Bacterial Cells

Figure 5A:
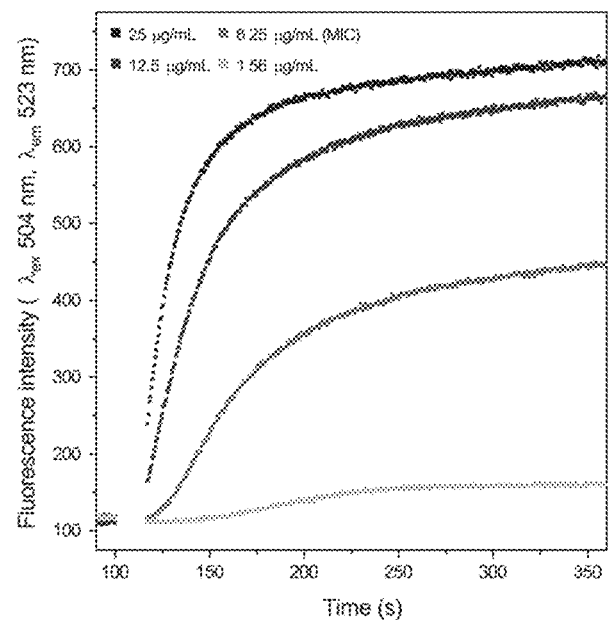
FIG. 5A-5F show the results of a phenotypic evaluation of STIP3-29 activity using spectrofluorometric assays of membrane integrity and polarization. Representative time-dependent changes to SYTOX Green fluorescence mixed with MRSA ATCC 33952 treated with STIP3-29 (shown in panel 5A) and D-STIP3-29 (shown in panel 5B). Representative time-dependent changes to DiSC3(5) fluorescence mixed with MRSA ATCC 33952 treated with STIP3-29 (shown in panel 5C) and D-STIP3-29 (shown in panel 5D). The MRSA was treated with four distinct peptide concentrations: 1.56, 6.25, 12.5 and 25 μg/mL, as indicated. Representative time-dependent changes to SYTOX Green (shown in panel 5E) and DiSC3(5) fluorescence (shown in panel 5F) mixed with MRSA ATCC BAA-1683, S. pseudintermedius, M. luteus, and K. pneumoniae treated with 25 μg/mL STIP3-29.
Figure 5B:
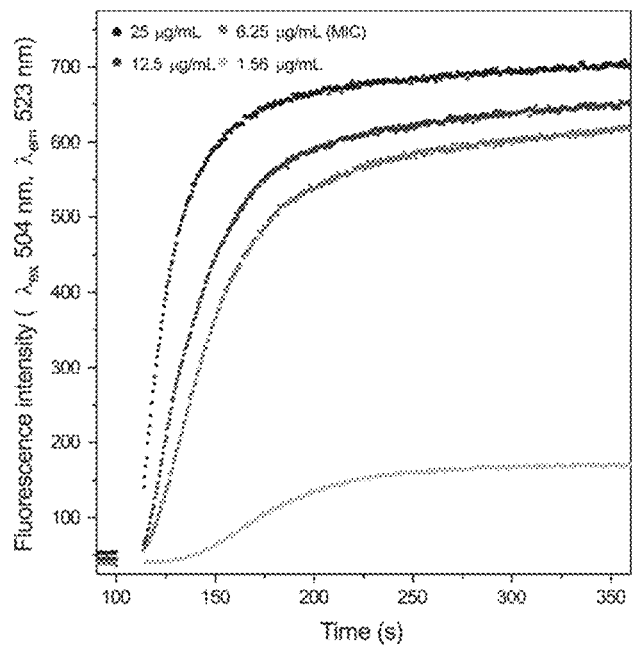
Figure 5C:
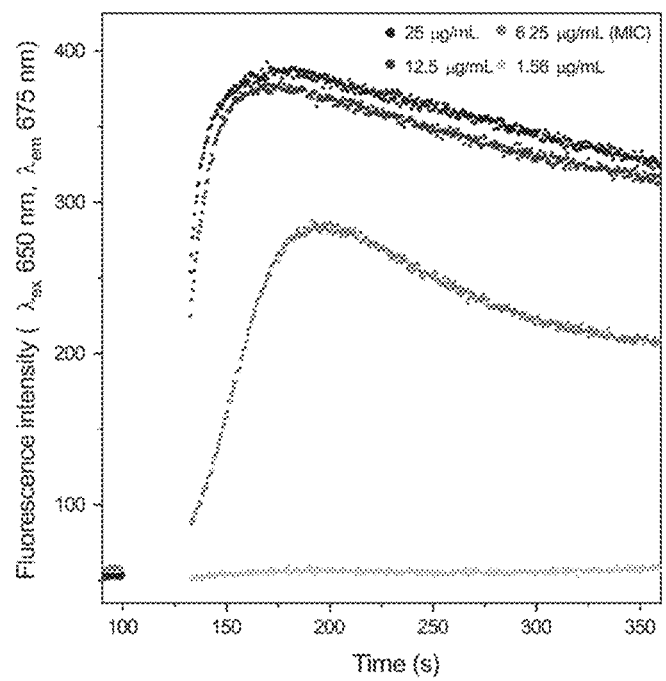
Figure 5D:
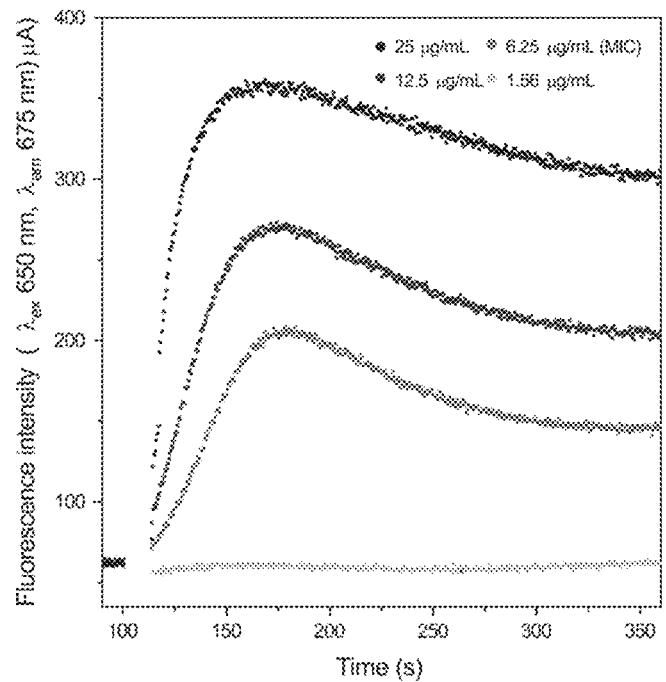
Figure 5E:
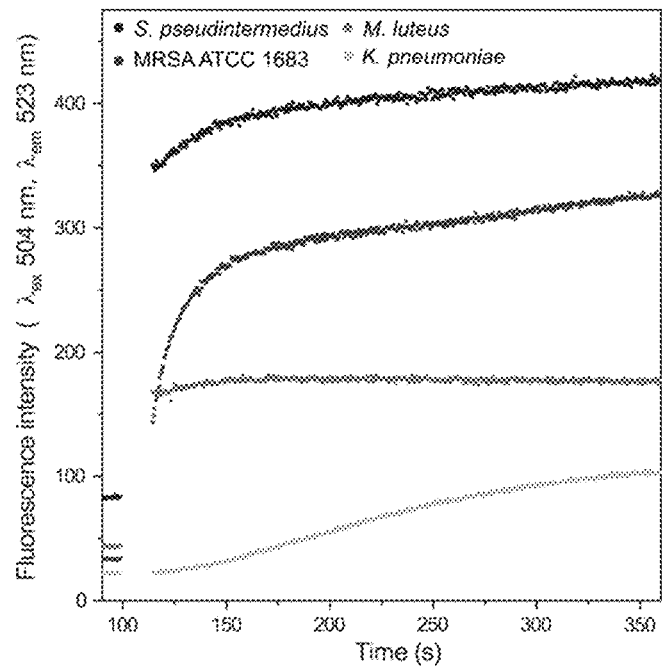
Figure 5F:
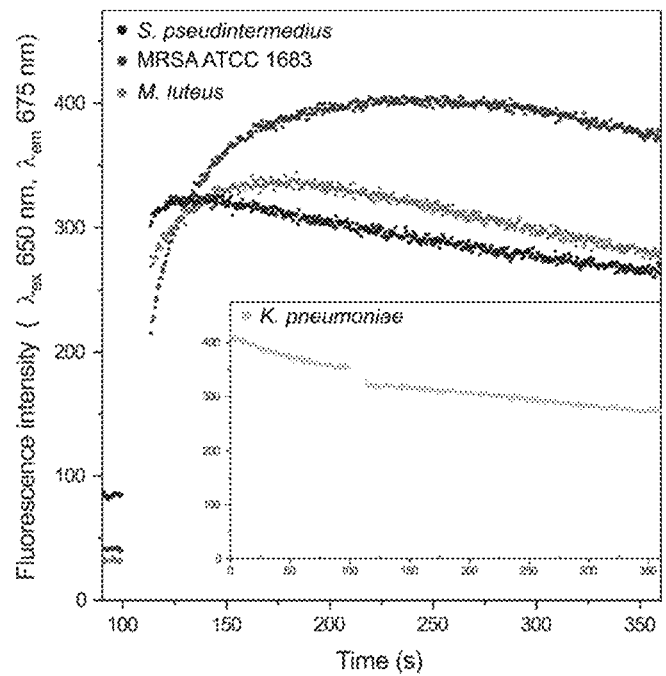

Membrane disruption and depolarization are commonly reported mechanisms of AMP action. Two indirect assays that rely on fluorescent dyes were employed to assess the interaction of STIP3-29 and D-STIP3-29 with bacterial membranes. First, changes to SYTOX fluorescence was measured when MRSA ATCC 33592 was treated with increasing peptide concentrations ranging from one fourth to four-fold the MIC. A rapid and concentration dependent increase in SYTOX fluorescence upon treatment with both L- and D-STIP3-29 was observed (FIG. 5A, B), consistent with translocation of the dye from the exterior to the interior of DNA-rich bacterial cells. Next, DiSC3(5), a cationic dye that binds to polarized membranes was used to report on possible depolarization related to AMP treatment. Again, a dose-dependent increase in fluorescence was observed (FIG. 5C, D), corresponding to the release of self-quenching DiSC3(5) molecules from the membrane. In contrast to the SYTOX green assay, no change in DiSC3(5) fluorescence was observed at the lowest concentration of STIP3-29 tested and a slow time-dependent decrease to DiSC3(5) fluorescence was observed after the rapid increase. This change in amplitude suggests re-association of the dye to membranes in the presence of the AMPs. Similar results were observed for three additional sensitive strains, MRSA ATCC 1683, *Staphylococcus pseudintermedius*, and *M. luteus* whereas SYTOX was slow to enter a resistant strain of *Klebsiella pneumoniae* (FIG. 5E). The changes to DiSC3(5) fluorescence of the three sensitive strains also mirrored the observations using MRSA ATCC 33952, and a slow linear decrease was observed for *K. pneumoniae* (FIG. 5F). Taken together, the data suggest that STIP3-29 treatment compromises membrane integrity and polarity; however, the observed process is unlikely to correspond to complete cell lysis as the changes to the signals from a fluorogenic probe of membrane potential were not sustained. Thus, without wishing to be bound by theory, a more conservative explanation of the results is that the cationic peptides increase membrane permeability to SYTOX and that the like-charge of the AMPs to the reporter of polarization may confound the interpretation of the indirect assay. For example, the AMPs may simply displace the self-quenching DiSC3(5) molecules from the membrane surface without causing depolarization.

Example 6

STIP3-29 Controls MRSA Colonization of 3D Epithelial Tissues

Figure 6C:
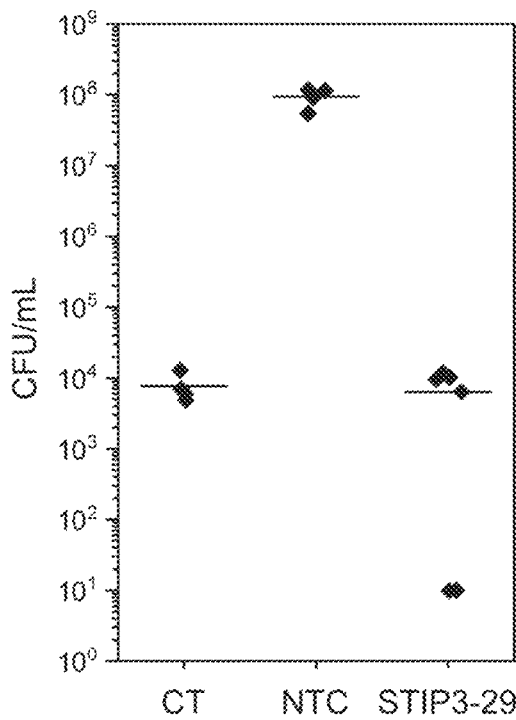
Figure 6C:
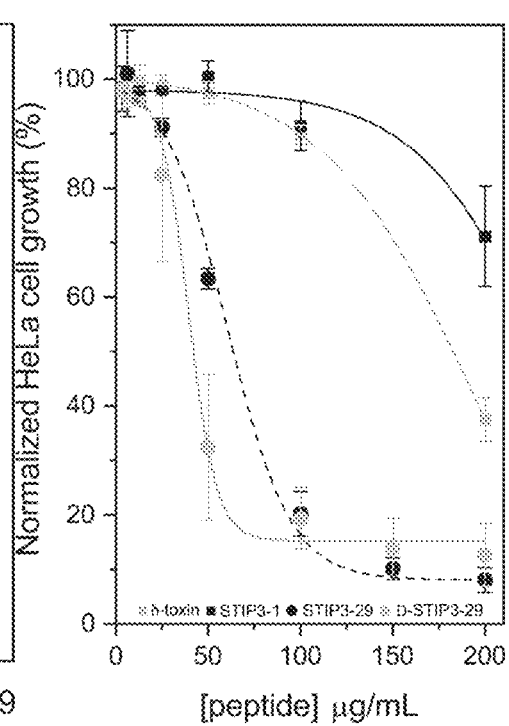
Figure 6C:
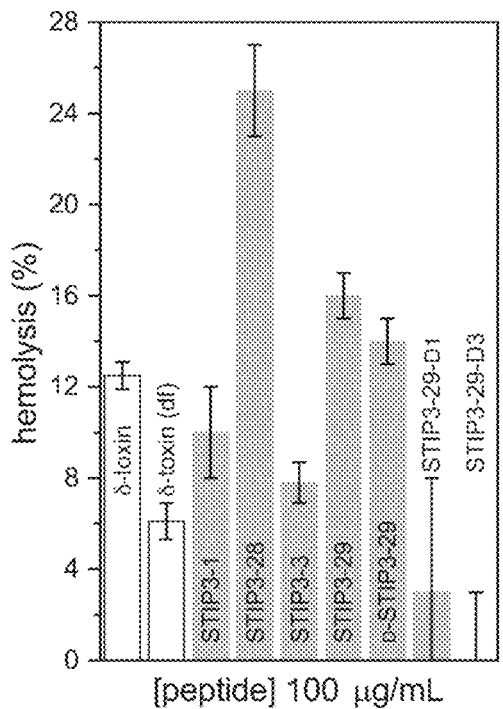

To begin to assess the potential utility of STIP3-29 as a topical antimicrobial agent, the ability of the peptide to control MRSA infections of three-dimensional epidermal skin model prepared from normal, human-derived epidermal keratinocytes (NHEK) in vitro was evaluated. The multilayered and highly differentiated tissue was colonized with MRSA 33952 through a 4 h exposure to $5 \times 10^5$ CFU before removing non-adherent cells. It was observed that $\sim 7 \times 10^3$ CFU (~1%) of the MRSA cells colonized the tissues, and that the population expanded by 4-log units in a 16 h period (FIG. 6A). The addition of 25 µg/ml STIP3-29 after colonization prevented the expansion of the MRSA population. The treatment was performed on 6 distinct tissue samples: in two cases the infection was reduced to below the detection limit of the assay whereas the cell density of MRSA in the other 4 samples did not differ significantly from the pre-treatment. Finally, an indirect measure of tissue health appeared to be unaffected by STIP3-29 treatment, however, the highly stratified epithelial surface should be examined at the apical surface to verify a lack of significant toxicity. In contrast to the NHEK tissues, STIP3-29 and the D-enantiomer displayed some cytotoxicity in vitro using a monolayer of HeLa cells. A dose-dependent decrease in HeLa cell survival was observed with IC50 values estimated at 230±30, 200±30, 56±1, and 39±3 µg/mL for the *S. auricularis* δ-toxin, STIP3-1, STIP3-29, and D-STIP3-29, respectively (FIG. 6B). In contrast to increase in cytotoxicity observed for STIP3-29 against HeLa cells, the hemolytic activity of the AMP was similar to that of the parent peptides when tested at 100 µg/mL (FIG. 6C). Amidation of the C-terminus is correlated with an increase in red blood cell lysis, observed by comparing of STIP3-1 to STIP3-28 and STIP3-3 to STIP3-29 whereas the inclusion of D-amino acids reduced the hemolytic activity.

Example 7

Summary of Additional Antibacterial and Antifungal Activity Measured for STIPs

To evaluate the antibiotic spectrum of δ-toxin inspired AMPs, the minimum inhibitory concentration (MIC) was determined for a number of bacteria (Table 7) and fungi (Table 7-9) that are pathogens and opportunistic causative agents of disease in humans, companion, and livestock animals. Although the peptide collection was tested against the emerging fungal pathogen *Candida auris* (strains AR 381, 382, 385, 386, 387 and 388), none were active.

Bacterial type strains were obtained from the American Type Culture Collection (ATCC) and clinical isolates were collected from cases in Canada. The fungal strains were provided by the National Microbiology Lab (Winnipeg, MB) and are part of the CDC and FDA Antibiotic Resistance Isolate Bank.

MIC determination. MICs were measured using peptides with 95% purity. For bacterial studies, cation-adjusted Mueller Hinton (MH) broth was used as the growth medium whereas Yeast Peptone Dextrose (YPD; 10 g/L yeast extract, 20 g/L peptone, 20 g/L dextrose) was used for *Candida* spp. and other yeast. Microorganisms were diluted to an optical density of $6 \times 10^4$ in MH or YPD broth and a 180 µl volume was mixed with 20 µl of peptide arrayed as a 2-fold dilution series in a flat-bottom 96-well microtitre plate. A control was performed using 20 µl of sterile water. Plates were incubated as standing cultures overnight at 37° C. The lowest peptide concentration that resulted in no observed microbial growth after an overnight treatment was defined as the MIC.

Figure 7:
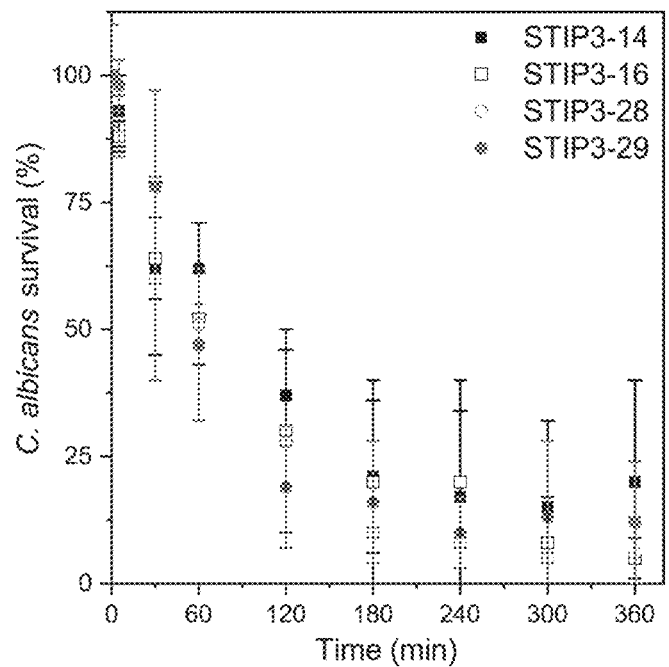
FIG. 7 is a bar graph showing time-dependent fungicidal activity of four STIP3 variants. C. albicans MYA-2876 were treated with STIPs at 25 μg/mL, a concentration twice the measured MIC.

*C. albicans* survival assay. The ability of STIP3-29 to kill *C. albicans* was evaluated by treating ~$1.5 \times 10^4$ cells at a concentration of 25 µg/mL. At regular time intervals, 100 mL of treated samples were plated on YPD agar plates and colonies were enumerated after 24 hours. Over the incubation period of 6 h, untreated cell populations expanded by 2-log units (FIG. 7).

Example 8

Materials and Methods

Reagents and peptides. All reagents used are of commercial origin. Synthetic peptides were purchased from GenScript (Piscataway, NJ); peptide purity of each ranged from 71 to 99% and the value for each preparation has been provided in Supporting Information.

Bacterial strains. *M. luteus* ATCC 4698, *S. aureus* ATCC 29213, a panel of 7 MRSA (ATCC MP-2), and a series of additional staphylococcal clinical isolates from human and veterinary cases were used. Bacterial strains were routinely grown in lysogeny broth (LB: 10 g/L tryptone, 5 g/L yeast extract, 10 g/L NaCl) at 37° C. prior to use in specific experiments described below.

Spot-on-lawn assay. For the initial screen, peptides of ≥70% purity were used. Each peptide was resuspended in sterile water to a concentration of 10 mg/ml. To determine antimicrobial activities a spot-on-lawn assay was performed. *M. luteus* and *S. aureus* were used as indicator strains. To prepare test organisms, the optical density (OD) of overnight cultures were measured and the organisms were diluted to an initial OD of 0.05 in soft nutrient agar (0.4% w/v) at 50° C. Next, 3 mL of soft agar containing a test organism was overlaid on a solid 1.5% w/v nutrient agar plate (LB). A total of 50 µg of each peptide was spotted on the inoculated surface and plates were incubated for 16 to 48 h before being examined for zones of inhibition.

SspA protease treatment. SspA protease was resuspended at 2 mg/mL in 100 mM HEPES, pH 7.8. Proteolysis was achieved by incubation of 50 µg PSMs at 37° C. for ~5 hours with 0.2 mg/mL SspA. The antimicrobial activity of the proteolytic products were assayed by spotting a 5 µL (~45 µg) from each treated peptide on each test microorganism as described above. The addition of SspA alone to the agar surface did not result in any microbial inhibition.

HPLC/MS analysis. High performance liquid chromatography coupled to mass spectrometry (HPLC-MS) was conducted to assess the proteolytic cleavage of synthetic PSMs by the SspA protease, as described above. Both treated samples and untreated controls were incubated at 37° C. for 5 hours, and then frozen until HPLC/MS analysis. An Agilent Infinity II 1260 HPLC outfitted with a Phenomenex Lune C5 column (4.6×150 mm, 5 µm) was used to separate the peptide fragments using a binary solvent system consisting of solvent A (water, 0.05% formic acid) and solvent B (acetonitrile, 0.05% formic acid) operating at 0.7 mL/min. A 5 µl volume (~4.5 µg) of each sample was injected at 10% solvent B, followed by a two-step gradient elution from 10 to 50% solvent B in 30 minutes, then 50 to 100% B in 10 minutes. The HPLC was coupled to an Advion CMS(L) single quadrupole mass detector through an electrospray ionization source. A line splitter from the HPLC to ESI source was used to deliver sample to the mass detector at 0.3 mL/min. An Advion expression-L CMS detector was used at low temperature and fragmentation settings: capillary temperature: 135° C., capillary voltage 120 V, source voltage offset 20 V, source gas temperature 135° C. and ESI voltage 3500 V. The range of ions detected was between 100 and 2,000 m/z.

Determination of minimum inhibitory concentrations. The MICs were measured for bioactive peptides identified from the initial screen. Peptide purity, sequences and MICs are listed in Tables 1, 4, and 5. For bacterial studies, cation-adjusted Mueller Hinton (MH) broth was used as the growth medium whereas YPD was used for *C. albicans*. Bacterial cultures were diluted to a OD value of $6 \times 10^{-4}$ in MH broth and a 180 µl volume was mixed with 20 µl of peptide arrayed as 2-fold dilution series in a 96-well plate. For the positive control, 20 µl of sterile water was used. Plates were incubated as standing cultures overnight at 37° C. The lowest peptide concentration that resulted no observed microbial growth after an overnight treatment was defined as the MIC.

Measurement of bactericidal activity. The time-dependent inhibition of pathogens was measured using standing cultures treated with 2×MIC (12.5 mg/mL STIP3-29). For *S. aureus*, an overnight culture was diluted to an OD of $5 \times 10^{-7}$ in 2 ml of MH broth supplemented with the appropriate concentration of peptide. Sterile water was added to control cultures. Standing cultures were incubated at 37° C. and 100 µl volume aliquots were removed at 60 min time intervals for 8 h. These aliquots were plated on agar plates to measure the colony forming units (CFUs) that remained viable upon treatment. Control aliquots from the same time intervals were diluted before plating to accurately enumerate increasing CFU counts. Counts were performed from plates that were incubated at 37° C. overnight. A plot of CFU/ml against time was used to illustrate and evaluate the time dependent killing. The same procedure was followed for *C. albicans* except that YPD broth and a cultivation temperature of 30° C. was employed.

Circular dichroism spectroscopy. Peptides were dissolved in water at concentrations between 0.3 and 0.5 mg/mL. CD spectra were recorded on an Applied Photophysics Chirascan Plus CD spectrophotometer at room temperature in a 0.1 cm path-length quartz cuvette. Spectra were recorded from 180 to 260 nm.

Three-dimensional tissue infection and treatment. 3D EpiDerm skin tissues (MatTek EPI-200-AFAB; antifungal & antibiotic-free; 9 mm) contained within a plastic insert lined with a permeable 0.4 µm membrane were transferred to a 12 well plate containing dye- and antibiotic assay medium (600 µl per well). A fresh MRSA ATCC 33592 culture in the log-phase of growth was centrifuged at 10,000 rpm for 5 min to harvest bacterial cells before resuspension in sterile PBS to an OD of $5 \times 10^{-6}$. Tissues were incubated with 100 µL of the bacterial cell suspension for 4 hours at 37° C. and 5%

CO2 in a humidified incubator. After 4 h incubation, the bacterial cell suspension was removed and the apical surface of each tissue was were washed 3 times with PBS to remove non-adherent bacterial cells. Next, the colonized skin tissues were treated with a 100 µL volume of STIP3-29 at 25 µg/mL. An equal volume of sterile PBS was used for untreated control experiments. Tissues were then incubated at 37° C. and 5% CO2 in a humidified incubator for 16 hours. To measure the MRSA colonization, inserts were washed three times with PBS, the NHEK tissues were then peeled from the plastic insert and transferred to a microcentrifuge tube with 400 µL volume of sterile PBS. Tissues in PBS were disrupted by vortexing for 1-2 min to detach the bacterial cells from the tissue, and bacterial cells were then concentrated by centrifugation to a final of volume of 100 µL, before serial dilutions were plated on LB agar and incubated overnight at 37° C. The number of colonies on each plated were counted and an average CFU/mL was determined for treated and untreated samples. This process was also performed prior to treatment to confirm that a population of adherent cells has been established in the skin model.

Peptide cytotoxicity. In vitro cytotoxicity was measured using the 3D EpiDerm skin tissues and HeLa Cells using a fluorescent reporter of cell viability, alamarBlue (ThermoFisher Scientific). 3D EpiDerm skin tissues (MatTek EPI-200-AFAB) were transferred to a 12 well plate containing 600 µL of AFAB-assay medium supplemented with 10% v/v alamarBlue. STIP3-29 (250 µg/mL; 40-fold MIC) or PBS was added on top of the tissues, and incubated at 37° C. and 5% CO2 in a humidified incubator for 24 h. HeLa cells were seeded in a 96-well plate ($2 \times 10^4$ cells/per well) and incubated overnight at 37° C. and 5% CO2 in a humidified incubator to prepare wells at ~50% confluency of adherent cells. After the incubation, spent DMEM was removed and cells were washed with PBS. alamarBlue-containing medium was prepared by mixing Phenol Red-free DMEM with alamarBlue solution at a 9:1 ratio and a 180 µl volume was added to each well. Cells were treated with peptides varying from 3.25 to 200 µg/mL and then incubated for 24 h. The fluorescence intensities of treated cultures were normalized to values measured for an untreated control group. After the 24 h incubation period, alamarBlue fluorescence was measured at 590 nm upon excitation at 560 nm using Varioskan Lux plate reader (Thermo Scientific) plate reader.

Hemolytic activity assay. Defibrinated sheep's blood (Hemostat Laboratories) at 35% concentration was centrifuged for 5 min at 4,000 rpm to harvest red blood cells. The cell pellet was washed three times with phosphate-buffered saline (PBS) at pH 7.4 and harvested again by centrifugation. The red blood cells were then diluted to 15% (v/v) in PBS prior to hemolysis. The assay was performed in 96 well plates in a final volume of 200 µl. The red blood cells were treated with peptides at 100 µg/mL; sterile water was used as a negative control and Triton X-100 (0.1% v/v) was used as a positive control for complete lysis. After 1 hour of incubation plates were centrifuged at 4,500 rpm for 10 min, and a 150 µl aliquot of the supernatant from each sample was carefully transferred to another 96-well plate. The absorbance of the supernatant was measured at 540 nm using a Varioskan Lux plate reader (Thermo Scientific). The hemolytic activity is reported as a percentage relative to complete lysis obtained using Triton X-100. Experiments were performed in triplicate.

Example 9

Evaluation of STIPs Against *M. haemolytica*

Figure 8:
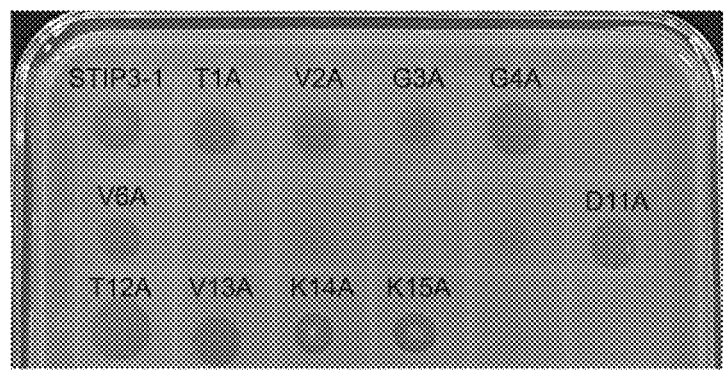
FIG. 8 shows the results of a spot-on-lawn assay of an alanine scanning experiment using Mannheimia haemolytica ATCC 33393 as an indicator strain.

The ability of STIP3 variants to inhibit the growth of *Mannheimia haemolytica* ATCC 33393 was evaluated. This included an alanine scan of STIP3-1 (FIG. 8 & Table 10) as well as 30 rationally-designed STIPs that were evaluated in the preceding Examples against other pathogens (Table 11). Substitutions at a greater number of sites were tolerated in the context of antimicrobial activity. Moreover, the inclusion of basic natural and unnatural amino acids (e.g. lysine, ornithine, and arginine) at positions 3, 4 and 11 (i.e. $X_1$, $X_2$, and $X_4$ of SEQ ID NO: 32) to afford a more uniformly cationic peptide increased activity against *M. haemolytica*.

Figure 9:
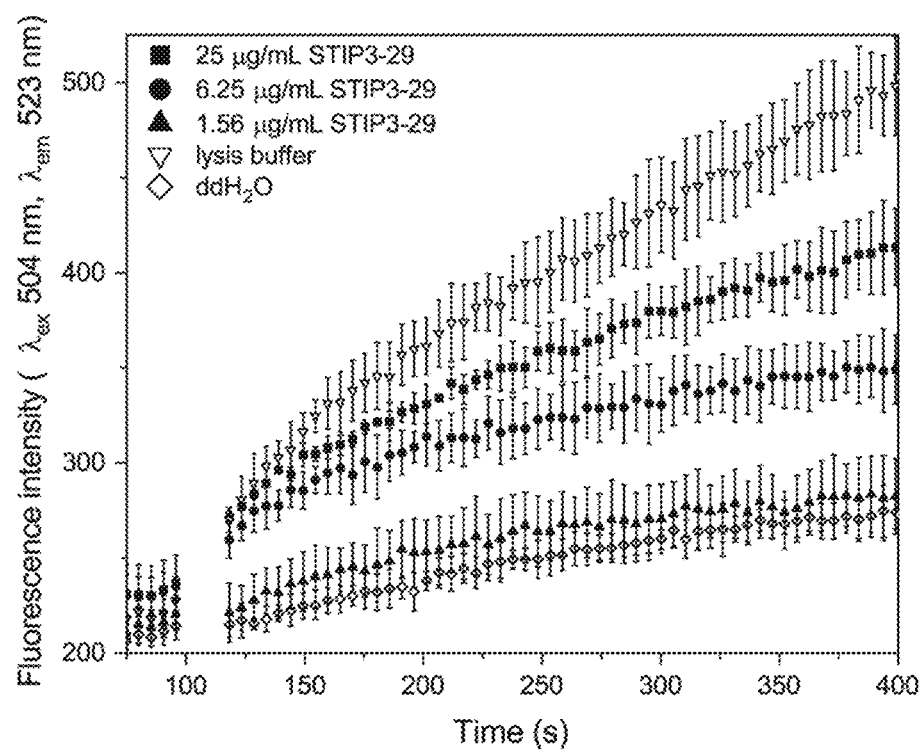
FIG. 9 shows M. haemolytica membrane permeabilization caused by STIP3-29 measured by SYTOX Green fluorescence. STIP3-29 was used at 4×, MIC and ¼ MIC and compared to a lysis buffer (1.2% Tritonx-100, 20 μg/ml Lysozyme, 2 mM EDTA, 20 mM TRIS, pH 8).

In addition to determining the MICs, as shown in FIG. 9, STIP3-29, was able to cause some membrane permeabilization (FIG. 9). The rate is slower for *M. haemolytica*, a double-membranes Gram-negative bacterium, compared to *S. aureus*; however, the results suggest that the peptide facilitates entry of the DNA-binding dye SYTOX Green into both Gram-negative and Gram-positive bacterial cells.

Example 10

Identification of an Additional Antifungal STIPs

The fact that the bioactive peptides are derived from the atypical δ-toxin of *S. auricularis* prompted a bioinformatic search for similar sequences. Based on an unusual distribution of acid amino acid residues, the δ-toxins of *S. condimenti* and *S. pettenkoferi* were identified as potential AMPs, and the ability of STIP versions of both to inhibit *Candida albicans* MYA-2876, *S. aureus* ATCC 29213, *M. luteus* ATCC 4698, and *M. haemolytica* ATCC 33393 were evaluated (Table 12). The results provide additional evidence that the C-terminal amidation may be less important for the antimicrobial activity against *Candida albicans* and that removal of an acidic residue at position 11 may improve activity of the AMPs.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

TABLE 1

Sequences, purity and characteristics of peptides screened for antimicrobial activity.

| Name | Peptide Sequence[a] | SEQ ID NO:[b] | Purity | MW (Da) | pI | Source Organism |
|---|---|---|---|---|---|---|
| PSMα1/ α1-2PSMα1 | (MS)IIAGIIKFIKGLIEKFTGK | 33 | 72.1% | 2089.6 | 10.00 | S. aureus |
| δ-toxin 1/ STIP1 | (MAAD)IISTISDLVKWIIDTVNKFTK | 34 | 85.1% | 2434.9 | 8.50 | S. aureus |
| δ-toxin 2/ STIP2 | (AQD)IISTIGDLVKWIIDTVNKFTK | 35 | 89.5% | 2404.9 | 8.50 | S. aureus |
| δ-toxin 3/ STIP3 | (MTKD)IVETVGGLVKWILDTVKKFA | 36 | 86.7% | 2216.7 | 8.50 | S. auricularis |
| δ-toxin 4/ STIP4 | (MLTMAAD)IISTIVEFVKLIAETIAKFMK | 37 | 94.4% | 2395.0 | 8.50 | S. cornubiensis |
| δ-toxin 5/ STIP5 | (MAAN)IISTIGDLVKWIIDTVNKFKK | 38 | 91.2% | 2431.9 | 8.53 | S. epidermidis |
| δ-toxin 6/ STIP6 | (MAGD)IIGTINDLIKWIADTVEKYKK | 39 | 82.8% | 2461.9 | 8.38 | S. massiliensis |
| δ-toxin 7/ STIP7 | (MAAD)IISTIGDLIKWIIDTVKKFKK | 40 | 70.8% | 2460.0 | 9.83 | S. saccharolyticus |

[a] amino acids in parentheses were omitted from the peptides in the screen; SspA cleavage sites are shown in bold + underline.
[b] SEQ ID NOs correspond to native δ-toxin sequence including the N-terminal residues indicated in (a);

TABLE 2

Summary of STIP fragments resulting from SspA protease treatment observed by LC/MS.

| Name | Peptides & detected fragments | SEQ ID NO: | Molecular ions (m/z) & identity observed | theoretical |
|---|---|---|---|---|
| STIP1 | IISTISDLVKWIIDTVNKFTK | 41 | 1218.9 | 1218.4 [M + 2H]$^{2+}$ |
|  |  |  | 813.1 | 812.6 [M + 3H]$^{3+}$ |
|  | IISTISD | 42 | 748.8 | 748.8 [M + H]$^{+}$ |
|  | LVKWIIDTVNKFTK | 43 | 570.1 | 569.3 [M + 3H]$^{3+}$ |
|  | TVNKFTK | 44 | 419.4 | 419.5 [M + 2H]$^{2+}$ |
|  | LVKWIID | 45 | 444.0 | 444.0 [M + 2H]$^{2+}$ |
| STIP2 | IISTIGDLVKWIIDTVNKFTK | 46 | 1204.1 | 1203.4 [M + 2H]$^{2+}$ |
|  |  |  | 802.9 | 802.6 [M + 3H]$^{3+}$ |
|  |  |  | 602.3 | 602.2 [M + 4H]$^{4+}$ |
|  | IISTIGD | 47 | 718.7 | 718.8 [M + H]$^{+}$ |
|  | TVNKFTK | 44 | 419.4 | 419.5 [M + 2H]$^{2+}$ |
|  | LVKWIID | 45 | 444.0 | 444.0 [M + 2H]$^{2+}$ |
| STIP3 | IVETVGGLVKWILDTVKKFA | 48 | 1110.0 | 1109.3 [M + 2H]$^{2+}$ |
|  |  |  | 740.3 | 739.9 [M + 3H]$^{3+}$ |
|  | IVE | 49 | 360.3 | 360.4 [M + H]$^{+}$ |
|  | TVGGLVKWILDTVKKFA | 1 | 626.3 | 626.1 [M + 3H]$^{3+}$ |
|  | TVKKFA | 50 | 693.9 | 693.8 [M + H]$^{+}$ |
|  |  |  | 347.3 | 347.4 [M + 2H]$^{2+}$ |
|  | TVGGLVKWILD | 51 | 601.3 | 601.2 [M + 2H]$^{2+}$ |
| STIP4 | IISTIVEFVKLIAETIAKFMK | 52 | 799.6 | 799.3 [M + 3H]$^{3+}$ |
|  |  |  | 599.8 | 599.7 [M + 4H]$^{4+}$ |
|  | IISTIVE | 53 | 774.7 | 774.9 [M + H]$^{+}$ |
|  | FVKLIAETIAKFMK | 54 | 820.9 | 820.5 [M + 2H]$^{2+}$ |
|  |  |  | 410.4 | 410.8 [M + 4H]$^{4+}$ |
|  | TIAKFMK | 55 | 419.9 | 420.0 [M + 2H]$^{2+}$ |

TABLE 2-continued

Summary of STIP fragments resulting from SspA protease treatment observed by LC/MS.

| Name | Peptides & detected fragments | SEQ ID NO: | Molecular ions (m/z) & identity | |
|---|---|---|---|---|
| | | | observed | theoretical |
| STIP5 | IISTIGDLVKWIIDTVNKFKK | 56 | 811.9 | 811.6 [M + 3H]$^{3+}$ |
| | | | 609.1 | 609.0 [M + 4H]$^{4+}$ |
| | IISTIGD | 47 | 718.7 | 718.8 [M + H]$^+$ |
| | TVNKFKK | 57 | 432.9 | 433.0 [M + 2H]$^{2+}$ |
| | LVKWIID | 45 | 887.3 | 887.1 [M + H]$^+$ |
| | | | 444.0 | 444.0 [M + 2H]$^{2+}$ |
| STIP6 | IIGTINDLIKWIADTVEKYKK | 58 | 822.1 | 821.6 [M + 3H]$^{3+}$ |
| | | | 616.7 | 616.5 [M + 4H]$^{4+}$ |
| | IIGTIND | 59 | 745.8 | 745.8 [M + H]$^+$ |
| | KYKK | 60 | 566.3 | 566.7 [M + H]$^+$ |
| | | | 283.8 | 283.8 [M + 2H]$^{2+}$ |
| | LIKWIAD | 61 | 430.0 | 430.0 [M + 2H]$^{2+}$ |
| | LIKWIADTVE | 62 | 594.6 | 594.7 [M + 2H]$^{2+}$ |
| STIP7 | IISTIGDLIKWIIDTVKKFKK | 63 | 821.5 | 821.0 [M + 3H]$^{3+}$ |
| | | | 616.3 | 616.0 [M + 4H]$^{4+}$ |
| | IISTIGDLIKWIID | 64 | 801.0 | 801.0 [M + 2H]$^{2+}$ |
| | TVKKFKK | 65 | 440.0 | 440.1 [M + 2H]$^{2+}$ |

SspA cleavage sites are shown in bold + underline.

TABLE 3

Summary of STIP3-1 and d-toxin fragments resulting from SspA protease treatment observed by LC/MS.

| Name | Peptides & detected fragments | SEQ ID NO: | Molecular ions (m/z) & identity | |
|---|---|---|---|---|
| | | | observed | theoretical |
| STIP3-1 | TVGGLVKWIIDTVKKFA | 1 | 469.8 | 469.8160 [M + 4H]$^{4+}$ |
| | TVGGLVKWIID | 51 | 601.2 | 601.2125 [M + 2H]$^{2+}$ |
| | TVKKFA | 50 | 347.4 | 347.4195 [M + 2H]$^{2+}$ |
| δ-toxin[a] | f-MTRDIVETVGGLVKWIIDTVKKFA | 36 | 1361.8 | 1361.1 [M + 2]$^{2+}$ |
| δ-toxin (deformyl) | MTRDIVETVGGLVKWIIDTVKKFA | 36 | 674.2 | 674.0625 [M + 4H]$^{4+}$ |
| | TVGGLVKWIIDTVKKFA | 1 | 626.1 | 626.09 [M + 3H]$^{3+}$ |
| | TVGGLVKWIID | 51 | 1201.9 | 1201.43 [M + H]$^+$ |
| | | | 601.2 | 601.215 [M + 2H]$^{2+}$ |
| | TVKKFA | 50 | 347.3 | 347.425 [M + 2H]$^{2+}$ |
| | MTRDIVE | 66 | 835.7 | 835.97 [M + H]$^+$ |
| | | | 418.3 | 418.485 [M + 2H]$^{2+}$ |

SspA cleavage sites are shown in bold + underline.
[a] no SspA cleavage was observed

TABLE 4

Summary of MICs observed for STIP3-1 alanine variants in liquid broth.

| ID | Peptide Sequence[c] | SEQ ID NO: | Purity | MIC (μg/mL)[a] | |
|---|---|---|---|---|---|
| | | | | M. luteus | S. aureus |
| WT | TVGGLVKWILDTVKKFA | 1 | | 12.5 | 100 |
| T1A | AVGGLVKWILDTVKKFA | 67 | 97.1% | 12.5 | 200 |
| V2A | TAGGLVKWILDTVKKFA | 68 | 97.8% | 50 | > |
| G3A | TVAGLVKWILDTVKKFA | 69 | 83.1% | 50 | >[b] |
| G4A | TVGALVKWILDTVKKFA | 70 | 98.4% | 12.5 | >[b] |
| L5A | TVGGAVKWILDTVKKFA | 71 | 83.6% | 100 | > |
| V6A | TVGGLAKWILDTVKKFA | 72 | 92.3% | 50 | > |
| K7A | TVGGLVAWILDTVKKFA | 73 | 97.7% | 200 | > |
| W8A | TVGGLVKAILDTVKKFA | 74 | 98.3% | 100 | > |
| I9A | TVGGLVKWALDTVKKFA | 75 | 90.3% | 200 | > |
| L10A | TVGGLVKWIADTVKKFA | 76 | 95.1% | 200 | > |

TABLE 4-continued

Summary of MICs observed for STIP3-1 alanine variants in liquid broth.

| ID | Peptide Sequence[c] | SEQ ID NO: | Purity | MIC (µg/mL)[a] M. luteus | S. aureus |
|---|---|---|---|---|---|
| D11A | TVGGLVKWILA<u>T</u>VKKFA | 2 | 87.5% | 3.13 | 100 |
| T12A | TVGGLVKWILDA<u>V</u>KKFA | 77 | 98.5% | 12.5 | 100 |
| V13A | TVGGLVKWILDT<u>A</u>KKFA | 78 | 90.4% | 50 | 200 |
| K14A | TVGGLVKWILDTV<u>A</u>KFA | 79 | 93.4% | 12.5 | >[b] |
| K15A | TVGGLVKWILDTVK<u>A</u>FA | 80 | 96.5% | 25 | >[b] |
| F16A | TVGGLVKWILDTVKK<u>A</u>A | 81 | 95.1% | 200 | > |

[a] > = >200 µg/mL (maximum concentration tested);
[b] inhibition observed on an agar surface;
[c] alanine substitutions are indicated by underlining

TABLE 5

Sequences, purity, and MICs of rationally-designed STIP3 variants tested against a panel of S. aureus.

| ID | Sequence[b] | SEQ ID NO: | Purity (%) | α helicity (%) | 29213 | BAA 44 (I) | BAA 41 (II) | BAA 33592 (III) | BAA 1683 (IV) | BAA 2094 (V) | BAA 42 (VI) | BAA 2313 (XI) |
|---|---|---|---|---|---|---|---|---|---|---|---|---|
| δ-toxin | f-MTKDIVETVGGLVKWILDTVKKFA | 36 | 97.5 | 88 | > | > | > | > | > | > | > | > |
| δ-toxin (df) | MTKDIVETVGGLVKWILDTVKKFA | 36 | 95.1 | 87 | > | > | > | > | > | > | > | > |
| STIP3-1 | TVGGLVKWILDTVKKFA | 1 | 98.3 | 67 | 100 | 100 | 100 | 100 | > | 100 | 100 | 100 |
| STIP3-2 | TVGGLVXWILATVKKFA | 2 | 95.3 | 50 | 100 | 100 | 100 | 50 | 50 | 50 | 50 | 50 |
| STIP3-3 | TVGGLVKWIL<u>K</u>TVKKFA | 3 | 91.2 |  | 25 | 25 | 25 | 25 | 50 | 25 | 50 | 50 |
| STIP3-4 | TVGGLVKWIL<u>N</u>TVKKFA | 4 | 99.9 |  | 100 | 50 | 50 | 50 | 100 | 50 | 50 | 100 |
| STIP3-5 | TVGGLVKWILDTVKKF<u>I</u> | 5 | 83.4 |  | 50 | 50 | 25 | 25 | 25 | 25 | 12.5 | 25 |
| STIP3-6 | TVGGLVKWILDTVKKF<u>W</u> | 6 | 95.5 |  | 12.5 | 25 | 12.5 | 12.5 | 12.5 | 12.5 | 12.5 | 12.5 |
| STIP3-7 | TVGGLVKWILDTVKKF<u>K</u> | 7 | 84.4 |  | > | > | > | > | > | > | > | > |
| STIP3-8 | TVG<u>V</u>LVKWILDTVKKFA | 3 | 83.7 |  | 100 | 100 | 100 | 100 | > | 100 | 100 | 100 |
| STIP3-9 | TVGGLVKWILD<u>V</u>VKKFA | 9 | 88.1 |  | 25 | 25 | 35 | 25 | 25 | 25 | 25 | 25 |
| STIP3-10 | TVGGLVKWILD<u>W</u>VKKFA | 10 | 93.2 |  | 100 | 200 | 100 | 100 | > | 100 | 25 | 50 |
| STIP3-11 | TVGGLVKWILDT<u>F</u>KKFA | 11 | 88.9 |  | 50 | 100 | 50 | 50 | 50 | 100 | 50 | 100 |
| STIP3-12 | TVGGLVKWIL<u>AA</u>VKKFA | 12 | 95.3 |  | 25 | 25 | 25 | 25 | 25 | 50 | 25 | 25 |
| STIP3-13 | TVGGLVKWIL<u>KA</u>VKKFA | 13 | 88.0 |  | 25 | 25 | 12.5 | 25 | 25 | 25 | 25 | 25 |
| STIP3-14 | TV<u>K</u>GLVKWIL<u>NV</u>VKKFA | 14 | 96.0 | 64 | 25 | 25 | 25 | 12.5 | 25 | 50 | 25 | 12.5 |
| STIP3-15 | TV<u>A</u>GLVKWILA<u>T</u>VKKFA | 15 | 94.2 |  | 25 | 25 | 50 | 12.5 | 25 | 25 | 50 | 50 |
| STIP3-16 | TV<u>K</u>GLVKWILA<u>T</u>VKKFA | 16 | 93.7 | 45 | 100 | 100 | 50 | 50 | > | 100 | 50 | 100 |
| STIP3-17 | TV<u>D</u>GLVKWILA<u>T</u>VKKFA | 17 | 96.1 |  | > | > | > | > | > | > | > | > |
| STIP3-18 | TV<u>KK</u>LVKWIL<u>K</u>TVKKFA | 18 | 92.3 |  | 100 | 100 | 100 | 100 | > | 100 | > | > |
| STIP3-19 | TV<u>KA</u>LVKWIL<u>K</u>TV<u>A</u>KFA | 19 | 95.2 |  | 50 | 25 | 50 | 25 | 25 | 25 | 50 | 25 |
| STIP3-20 | TV<u>RA</u>LVKWIL<u>R</u>TV<u>A</u>KFA | 20 | 97.3 |  | 25 | 25 | 12.5 | 25 | 25 | 25 | 25 | 50 |
| STIP3-21 | TV<u>KA</u>LVKWIL<u>K</u>TV<u>A</u>KF<u>W</u> | 21 | 96.3 |  | 25 | 25 | 25 | 25 | 12.5 | 12.5 | 25 | 12.5 |
| STIP3-22 | TV<u>X</u>ALV<u>X</u>WIL<u>X</u>TVA<u>X</u>FA | 22 | 84.6 |  | 25 | 25 | 25 | 25 | 25 | 25 | 25 | 100 |

TABLE 5-continued

Sequences, purity, and MICs of rationally-designed STIP3 variants tested against a panet of S. aureus.

| ID | Sequence[b] | SEQ ID NO: | Purity (%) | α helicity (%) | 29213 | BAA 44 (I) | BAA 41 (II) | 33592 (III) | BAA 1683 (IV) | BAA 2094 (V) | BAA 42 (VI) | BAA 2313 (XI) |
|---|---|---|---|---|---|---|---|---|---|---|---|---|
| STIP3-23 | TVRALVRWILRTVARFA | 23 | 88.8 | | 25 | 25 | 6.25 | 25 | 25 | 50 | 50 | 25 |
| STIP3-24 | TVGVLVKWILNVVAKFA | 24 | 82.5 | | > | > | > | > | > | > | > | > |
| STIP3-25 | TVKFLVKWILKWVAKFA | 25 | 96.4 | | > | > | > | > | > | > | > | > |
| STIP3-26 | TVKVLVKWILKVVAKFA | 26 | 84.5 | | > | > | > | > | > | > | > | > |
| STIP3-27 | TVGGLVKWILDTVKKFA-NH₂ | 27 | 96.3 | | 50 | 25 | 25 | 50 | 25 | 25 | 25 | 50 |
| STIP3-28 | TVGGLVKWILATVKKFA-NH₂ | 28 | 97.4 | 75 | 25 | 12.5 | 12.5 | 6.25 | 12.5 | 6.25 | 12.5 | 12.5 |
| STIP3-30 | TVKGLYKWILNVVKKFA-NH₂ | 30 | 95.9 | | 12.5 | 12.5 | 25 | 12.5 | 12.5 | 25 | 25 | 25 |
| STIP3-31 | TVXALVKWILKIVAKFW-NH₂ | 31 | 97.4 | | 25 | 25 | 25 | 25 | 25 | 25 | 50 | 25 |
| STIP3-29 | TVGGLVLWILKTVKKFA-NH₂ | 29 | 95.1 | 61 | 12.5 | 6.25 | 6.25 | 6.25 | 6.25 | 6.25 | 6.25 | 6.25 |
| D-STIP3-29 | TVGGLVKWIIXTVKKFA-NH₂ | 29 | 98.6 | 47 | 6.25 | 12.5 | 6.25 | 6.25 | 6.25 | 6.25 | 6.25 | 6.25 |
| STIP3-29-D1 | TVGGLVKWIIXTVKKFA-NH₂ | 29 | 96.3 | 51 | 12.5 | | | 25 | | | | |
| STIP3-29-D3 | TVGGLVKWIIXTVKKFA-NH₂ | 29 | 97.0 | 32 | > | | | > | | | | |

[a] > symbol indicates that no inhibition was observed at the highest concentration of peptide tested: 100 μg/mL for the STIP3 variants, 200 μg/mL for the δ-toxins
[b] amino acid substitutions and modifications (C-temninal amidation) are indicated by underlining: X indicates l-ornithine, D-amino acids are indicated in bold.

TABLE 6

MICs of STIP3-29 for other staphylococcal species

| Bacterium | MIC (μg/ml) |
|---|---|
| *S. aureus* | |
| bovid isolate (RDM-1)[a] | 6.25 |
| *S. pseudintermedius*[a] human isolates | |
| SPC001 (MSSP) | 3.13 |
| SPC002 (MSSP) | 3.13 |
| SPC020 (MSSR) | 3.13 |
| canine isolates[a] | |
| MSSP42 | 3.13 |
| MRSP16 | 3.13 |
| MRSP24 | 3.13 |
| *S. auricularis*[b] | 1.56 |
| *S. epidermidis*[b] | 3.13 |
| *S. equorum*[b] | 3.13 |
| *S. scuri*[b] | 3.13 |

[a] clinical, disease-causing isolate
[b] isolate from a healthy dairy cow

TABLE 7

Summary of antibacterial activity of STIP3-29

| Bacterium | MIC (μg/ml) |
|---|---|
| *Streptococcus agalactiae*[a] | 3.13 |
| *Streptococcus canis*[a] | 6.25 |
| *Streptococcus dysagalactiae*[a] | 3.13 |
| *Streptococcus equi*[a] | 3.13 |
| *Streptococcus zooepidermicus*[a] | 3.13 |
| *Microccus luteus* ATCC 4698 | 1.56 |
| *Enterococcus faecalis* ATCC 2912 | 12.5 |
| *Mannheimia haemolytica*[a] | 6.25 |
| *Klebsiella pneumoniae*[a] | > |
| *Pseudomonas aeruginosa* ATCC 27853 | > |
| *Pasteurella multocida* | > |
| *Mycoplasma bovis* | > |

[a] clinical, disease-causing isolate
[b] isolate from a healthy dairy cow
> indicates no inhibition up to 50 μg/ml

TABLE 8

Summary of MICs[a] of δ-toxins and STIPs for two *C. albicans* strains.

| ID | Sequence[b] | SEQ ID NO: | MYA-2876 | Y537 |
|---|---|---|---|---|
| δ-toxin | f-MTKDIVETVGGLVKWILDTVKKFA | 36 | > | |
| δ-toxin (df) | MTKDIVETVGGLVKWILDTVKKFA | 36 | 100 | |
| STIP3-1 | TVGGLVKWILDTVKKFA | 1 | 25 | |
| STIP3-2 | TVGGLVKWIL A TVKKFA | 2 | 100 | |
| STIP3-4 | TVGGLVKWIL N TVKKFA | 4 | 12.5 | |
| STIP3-5 | TVGGLVKWILDTVKKF I | 5 | 100 | |
| STIP3-6 | TVGGLVKWILDTVKKF W | 6 | 50 | |
| STIP3-7 | TVGGLVKWILDTVKKF K | 7 | 50 | |
| STIP3-8 | TVG V LVKWILDTVKKFA | 8 | > | |
| STIP3-9 | TVGGLVKWILD V VKKFA | 9 | 50 | |
| STIP3-10 | TVGGLVKWILD W VKKFA | 10 | 50 | |
| STIP3-11 | TVGGLVKWILDT F KKFA | 11 | 25 | |
| STIP3-12 | TVGGLVKWIL A AVKKFA | 12 | 100 | |
| STIP3-13 | TVGGLVKWIL K AVKKFA | 13 | 50 | |
| STIP3-15 | TV A GLVKWIL A TVKKFA | 15 | 25 | |
| STIP3-16 | TV K GLVKWIL A TVKKFA | 16 | 12.5 | |
| STIP3-17 | TV D GLVKWIL A TVKKFA | 17 | 12.5 | |
| STIP3-18 | TV KK LVKWIL K TVKKFA | 18 | 50 | > |
| STIP3-19 | TV K ALVKWIL K TV A KFA | 19 | > | > |
| STIP3-20 | TV R ALVKWIL R TV A KFA | 20 | > | > |
| STIP3-21 | TV K ALVKWIL K TV A KF W | 21 | > | > |
| STIP3-22 | TV X ALV X WIL X TV A X FA | 22 | > | |
| STIP3-23 | TV R ALV R WIL R TV A R FA | 23 | > | |
| STIP3-24 | TVG V LVKWIL N V VAKFA | 24 | > | |
| STIP3-25 | TV K F LVKWIL K W VAKFA | 25 | 25 | 25 |
| STIP3-26 | TV K V LVKWIL K V VAKFA | 26 | > | > |
| STIP3-27 | TVGGLVKWILDTVKKFA-NH₂ | 27 | 25 | 50 |
| STIP3-28 | TVGGLVKWIL A TVKKFA-NH₂ | 28 | 12.5 | 25 |
| STIP3-30 | TV K GLVKWIL N VVKKFA-NH₂ | 30 | 25 | 50 |
| STIP3-31 | TV KA LVKWIL K TV A KF W -NH₂ | 31 | > | > |
| STIP3-29 | TVGGLVKWIL K TVKKFA-NH₂ | 29 | 12.5 | 25 |
| D-STIP3-29 | TVGGLVKWIL K TVKKFA-NH₂ | 29 | 50 | 50 |
| STIP3-29-D1 | TVGGLVKWIL K TVKKFA-NH₂ | 29 | 12.5 | 25 |
| STIP3-3 | TVGGLVKWIL K TVKKFA | 3 | 25 | 50 |
| D-STIP3-3 | TVGGLVKWIL K TVKKFA | 3 | 12.5 | 25 |

TABLE 8-continued

Summary of MICs[a] of δ-toxins and STIPs for two *C. albicans* strains.

| ID | Sequence[b] | SEQ ID NO: | MYA-2876 | Y537 |
|---|---|---|---|---|
| STIP3-3 | TVGGLVKWILKTVKKFA | 3 | 25 | 50 |
| STIP3-14 | TVKGLVKWILNVVKKFA | 14 | 12.5 | 50 |
| D-STIP3-14 | TVKGLVKWILNVVKKFA | 14 | 50 | 50 |
| STIP3-14-D1 | TVKGLVKWILNVVKKFA | 14 | 12.5 | 25 |

[a] > symbol indicates that no inhibition was observed at the highest concentration of peptide tested: 100 µg/mL
[b] amino acid substitutions and modifications (C-terminal amidation) are indicated by underlining; X indicates L-ornithine; D-amino acids are indicated in bold

TABLE 9

MICs (µg/mL) of STIPs measured using the CDC and FDA AR Candida isolate panel[a].

| Peptide ID | *Candida duobushaemutonii* AR 391 | AR 392 | AR 394 | *Candida haomulonii* AR 393 | AR 395 | *Kodamae ohmeri* AR 396 | *Candida krusei* AR 397 | *Candida lusitaniae* AR 398 | *Saccharomyces cerevisiae* AR 399 | AR 400 |
|---|---|---|---|---|---|---|---|---|---|---|
| δ-toxin | > | > | > | > | > | > | > | > | > | > |
| δ-toxin (df) | > | > | > | > | > | > | > | > | > | > |
| STIP3-1 | > | > | > | > | > | > | 25 | 100 | 50 | 12.5 |
| STIP3-2 | > | > | > | > | > | 100 | 50 | > | 50 | 100 |
| STIP3-14 | 50 | 50 | 100 | > | > | 25 | 12.5 | 6.25 | 25 | 6.25 |
| STIP3-19 | 50 | 100 | 100 | > | > | > | 100 | 50 | 100 | 50 |
| STIP3-21 | > | > | > | > | NT | > | 100 | 50 | > | 200 |
| STIP3-29 | 25 | 50 | 100 | 200 | NT | 50 | 50 | 25 | 50 | 25 |
| STIP3-30 | 12.5 | 25 | 25 | 100 | NT | 25 | 12.5 | 6.25 | 25 | 12.5 |
| STIP3-3 | 100 | > | > | > | > | 100 | 100 | 100 | 100 | 100 |
| STIP3-4 | > | > | > | > | > | > | 100 | 100 | 100 | 100 |
| STIP3-5 | > | > | > | > | > | > | 100 | 100 | 100 | 100 |
| STIP3-6 | > | > | > | > | > | > | 100 | 100 | 100 | 100 |
| STIP3-7 | > | > | > | > | > | > | 100 | 100 | 100 | 100 |
| STIP3-8 | > | > | > | > | > | > | 100 | 180 | 100 | 100 |
| STIP3-9 | > | > | > | > | > | > | 100 | 100 | 100 | 100 |
| STIP3-10 | > | > | > | > | > | > | > | > | > | 100 |
| STIP3-11 | > | > | > | > | > | > | 100 | 100 | 100 | 100 |
| STIP3-12 | > | > | > | > | > | > | 100 | 100 | 100 | 100 |
| STIP3-13 | 100 | 100 | 100 | > | > | > | 100 | 100 | 100 | 100 |
| STIP3-15 | > | > | > | > | > | 100 | 100 | 100 | 100 | 100 |
| STIP3-16 | > | > | > | > | > | 100 | 100 | 100 | 100 | 100 |
| STIP3-17 | > | > | > | > | > | > | 100 | 100 | 100 | 100 |
| STIP3-18 | 100 | 100 | 100 | > | > | > | 100 | 100 | 100 | 100 |
| STIP3-20 | > | > | > | > | > | > | > | > | > | 200 |
| STIP3-22 | > | > | > | > | > | > | 100 | 100 | 100 | 100 |
| STIF3-23 | > | > | > | > | > | > | > | 100 | 100 | 100 |
| STIP3-24 | > | > | > | > | > | > | > | 100 | 100 | 100 |
| STIP3-25 | > | > | > | > | > | > | > | 100 | 100 | 100 |
| STIP3-26 | > | > | > | > | > | > | > | 100 | 100 | 100 |
| STIP3-27 | > | > | > | > | > | 100 | 100 | 100 | 100 | 100 |
| STIP3-28 | > | > | > | > | 100 | 100 | 100 | 100 | 100 | 100 |
| STIP3-31 | > | > | > | > | NT | > | > | > | > | > |

[a] MIC values reported at the top of the table (above the double line) are based on titrations from 1.56 to 100 µg/mL;
values below the line were determined using two concentrations of peptide 200 or 100 µg/mL, therefore the values reported as 100 µg/mL are ≤100 µg/mL but unlikely lower than 6.25 µg

TABLE 10

Summary of MICs observed for alanine substituted STIP3-1 experiment in liquid broth.

| | MIC (µg/mL)[a] | | |
|---|---|---|---|
| | *M. luteus* | *S. aureus* | *M. haemolytica* |
| STIP3-1 | 12.5 | 100 | 6.25 |
| T1A | 12.5 | 200 | 50 |
| V2A | 50 | > | 100 |
| G3A | 50 | >[b] | 100 |
| G4A | 12.5 | >[b] | 50 |
| L5A | 100 | > | > |

TABLE 10-continued

Summary of MICs observed for alanine substituted STIP3-1 experiment in liquid broth.

| | MIC (μg/mL)[a] | | |
|---|---|---|---|
| | *M. luteus* | *S. aureus* | *M. haemolytica* |
| V6A | 50 | > | 100 |
| K7A | 200 | > | > |
| W8A | 100 | > | 200 |
| I9A | 200 | > | > |
| L10A | 200 | > | 200 |
| D11A | 3.13 | 100 | 50 |
| T12A | 12.5 | 100 | 50 |
| V13A | 50 | 200 | 200 |
| K14A | 12.5 | >[b] | 100 |
| K15A | 25 | >[b] | 50 |
| F16A | 200 | > | > |

[a] the use of > indicates an MIC > 200 μg/mL; the maximum concentration tested
[b] inhibition observed on an agar surface

TABLE 11

Summary of MICs observed for STIPs against *M. haemolytica*.

| ID | Sequence[b] | SEQ ID NO: | MIC (μg/mL) |
|---|---|---|---|
| δ-toxin | f-MTKDIVETVGGLVKWILDTVKKFA | 36 | > |
| δ-toxin (df) | MTKDIVETVGGLVKWILDTVKKFA | 36 | > |
| STIP3-1 | TVGGLVKWILDTVKKFA | 1 | 25 |
| STIP3-2 | TVGGLVKWILATVKKFA | 2 | 25 |
| STIP3-3 | TVGGLVKWILKTVKKFA | 3 | 12.5 |
| STIP3-4 | TVGGLVKWILNTVKKFA | 4 | 25 |
| STIP3-5 | TVGGLVKWILDTVKKFI | 5 | 25 |
| STIP3-6 | TVGGLVKWILDTVKKFW | 6 | 25 |
| STIP3-7 | TVGGLVKWILDTVKKFK | 7 | 25 |
| STIP3-8 | TVGVLVKWILDTVKKFA | 8 | > |
| STIP3-9 | TVGGLVKWILDVVKKFA | 9 | 25 |
| STIP3-10 | TVGGLVKWILDWVKKFA | 10 | > |
| STIP3-11 | TVGGLVKWILDTFKKFA | 11 | > |
| STIP3-12 | TVGGLVKWILAVVKKFA | 12 | 25 |
| STIP3-13 | TVGGLVKWILKAVKKFA | 13 | 12.5 |
| STIP3-15 | TVAGLVKWILATVKKFA | 15 | 25 |
| STIP3-16 | TVKGLVKWILATVKKFA | 16 | 6.25 |
| STIP3-17 | TVDGLVKWILATVKKFA | 17 | > |
| STIP3-18 | TVKKLVKWILKTVKKFA | 18 | 6.25 |
| STIP3-19 | TVKALVKWILKTVAKFA | 19 | 12.5 |
| STIP3-20 | TVRALVKWILRTVAKFA | 20 | 25 |
| STIP3-21 | TVKALVKWILKTVAKFW | 21 | 12.5 |
| STIP3-22 | TVXALVXWILXTVAXFA | 22 | 6.25 |
| STIP3-23 | TVRALVRWILRTVARFA | 23 | 12.5 |
| STIP3-24 | TVGVLVKWILNVVAKFA | 24 | > |
| STIP3-25 | TVKFLVKWILKWVAKFA | 25 | > |
| STIP3-26 | TVKVLVKWILKVVAKFA | 26 | > |
| STIP3-27 | TVGGLVKWILDTVKKFA-NH2 | 27 | 25 |
| STIP3-28 | TVGGLVKWILATVKKFA-NH2 | 28 | 12.5 |

TABLE 11-continued

Summary of MICs observed for STIPs against *M. haemolytica*.

| ID | Sequence[b] | SEQ ID NO: | MIC (μg/mL) |
|---|---|---|---|
| STIP3-29 | TVGGLVKWIL<u>K</u>TVKKFA-<u>NH₂</u> | 29 | 25 |
| STIP3-30 | TV<u>K</u>GLVKWIL<u>N</u>VVKKFA-<u>NH₂</u> | 30 | 12.5 |
| STIP3-31 | TV<u>KA</u>LVKWIL<u>K</u>TVAK<u>W</u>-<u>NH₂</u> | 31 | 6.25 |

[a] > symbol indicates that no inhibition was observed at the highest concentration of peptide tested: 25 μg/mL
[b] amino acid substitutions and modifications are indicated by underlining; X indicates L-ornithine

TABLE 12

Summary of MICs observed for additional STIPs against 4 microorganisms.

| | | | MIC (μg/mL)[a] | | | |
|---|---|---|---|---|---|---|
| ID | Sequence | SEQ ID NO: | C. albicans | S. aureus | M. luteus | M. haemolytica |
| STIP8-1 | TVKSFVNLILDTVKKYAK | 84 | 100 | > | 100 | > |
| STIP8-2 | TVKSFVNLILKTVKKYAK | 85 | 100 | > | 6.25 | 100 |
| STIP8-3 | TVKSFVNLIL<u>K</u>TVKKYAK-<u>NH₂</u> | 86 | > | > | 3.13 | 50 |
| STIP9-1 | TVTKFVKLIAETVKKFTK | 87 | 100 | > | 50 | 200 |
| STIP9-2 | TVTKFVKLIA<u>K</u>TVKKFTK | 88 | 25 | > | 6.25 | 100 |
| STIP9-3 | TVTKFVKLIA<u>K</u>TVKKFTK-<u>NH₂</u> | 89 | 100 | > | 3.13 | 100 |

[a] the use of > indicates an MIC >200 μg/mL; the maximum concentration tested

REFERENCES

1. Tacconelli, E.; Carrara, E.; Savoldi, A.; Harbarth, S.; Mendelson, M.; Monnet, D. L.; Pulcini, C.; Kahlmeter, G.; Kluytmans, J.; Carmeli, Y.; Ouellette, M.; Outterson, K.; Patel, J.; Cavaleri, M.; Cox, E. M.; Houchens, C. R.; Grayson, M. L.; Hansen, P.; Singh, N.; Theuretzbacher, U.; Magrini, N.; Group, W.H.O.P.P.L.W., Discovery, research, and development of new antibiotics: the WHO priority list of antibiotic-resistant bacteria and tuberculosis. *Lancet Infect Dis* 2018, 18 (3), 318-327.
2. UK Government and Wellcome Trust, O. N.J., Tackling drug-resistant infections globally: final report and recommendations. 2016.
3. Klein, E. Y.; Sun, L.; Smith, D. L.; Laxminarayan, R., The changing epidemiology of methicillin-resistant *Staphylococcus aureus* in the United States: a national observational study. *Am J Epidemiol* 2013, 177 (7), 666-74.
4. Lee, A. S.; de Lencastre, H.; Garau, J.; Kluytmans, J.; Malhotra-Kumar, S.; Peschel, A.; Harbarth, S., Methicillin-resistant *Staphylococcus aureus*. *Nat Rev Dis Primers* 2018, 4, 18033.
5. Klein, E. Y.; Jiang, W.; Mojica, N.; Tseng, K. K.; McNeill, R.; Cosgrove, S. E.; Perl, T. M., National Costs Associated With Methicillin-Susceptible and Methicillin-Resistant *Staphylococcus aureus* Hospitalizations in the United States, 2010-2014. *Clin Infect Dis* 2019, 68 (1), 22-28.
6. Zhen, X.; Lundborg, C. S.; Sun, X.; Hu, X.; Dong, H., The Clinical and Economic Impact of Antibiotic Resistance in China: A Systematic Review and Meta-Analysis. *Antibiotics (Basel)* 2019, 8 (3).
7. Canadian Antimicrobial Resistance Surveillance System. Public Health Agency of Canada: 2016.
8. Goetghebeur, M.; Landry, P. A.; Han, D.; Vicente, C., Methicillin-resistant *Staphylococcus aureus*: A public health issue with economic consequences. *Can J Infect Dis Med Microbiol* 2007, 18 (1), 27-34.
9. Bauman, C. A.; Barkema, H. W.; Dubuc, J.; Keefe, G. P.; Kelton, D. F., Identifying management and disease priorities of Canadian dairy industry stakeholders. *J Dairy Sci* 2016, 99 (12), 10194-10203.
10. Canada's Dairy Industry at a Glance. Government of Canada: 2017.
11. Canada's Dairy Industry at a Glance. Government of Canada: 2016.
12. M., J. *Dairy Research Cluster Sustainable Development—Summary* 2014; The Canadian Bovine Mastitis and Milk Quality Research Network: 2014.
13. Rollin, E.; Dhuyvetter, K. C.; Overton, M. W., The cost of clinical mastitis in the first 30 days of lactation: An economic modeling tool. *Prev Vet Med* 2015, 122 (3), 257-64.
14. *Canadian Antimicrobial Resistance Surveillance System—Report* 2016; 2016.
15. Robbins, N.; Wright, G. D.; Cowen, L. E., Antifungal Drugs: The Current Armamentarium and Development of New Agents. *Microbiol Spectr* 2016, 4 (5).
16. Brown, G. D.; Denning, D. W.; Gow, N. A.; Levitz, S. M.; Netea, M. G.; White, T. C., Hidden killers: human fungal infections. *Sci Transl Med* 2012, 4 (165), 165rv13.
17. Wilson, L. S.; Reyes, C. M.; Stolpman, M.; Speckman, J.; Allen, K.; Beney, J., The direct cost and incidence of systemic fungal infections. *Value Health* 2002, 5 (1), 26-34.

18. Wang, G.; Narayana, J. L.; Mishra, B.; Zhang, Y.; Wang, F.; Wang, C.; Zarena, D.; Lushnikova, T.; Wang, X., Design of Antimicrobial Peptides: Progress Made with Human Cathelicidin LL-37. *Adv Exp Med Biol* 2019, 1117, 215-240.
19. de Breij, A.; Riool, M.; Cordfunke, R. A.; Malanovic, N.; de Boer, L.; Koning, R. I.; Ravensbergen, E.; Franken, M.; van der Heijde, T.; Boekema, B. K.; Kwakman, P. H. S.; Kamp, N.; El Ghalbzouri, A.; Lohner, K.; Zaat, S. A. J.; Drijfhout, J. W.; Nibbering, P. H., The antimicrobial peptide SAAP-148 combats drug-resistant bacteria and biofilms. *Sci Transl Med* 2018, 10 (423).
20. Haisma, E. M.; Goblyos, A.; Ravensbergen, B.; Adriaans, A. E.; Cordfunke, R. A.; Schrumpf, J.; Limpens, R. W.; Schimmel, K. J.; den Hartigh, J.; Hiemstra, P. S.; Drijfhout, J. W.; El Ghalbzouri, A.; Nibbering, P. H., Antimicrobial Peptide P60.4Ac-Containing Creams and Gel for Eradication of Methicillin-Resistant *Staphylococcus aureus* from Cultured Skin and Airway Epithelial Surfaces. *Antimicrob Agents Chemother* 2016, 60 (7), 4063-72.
21. Nibbering, P. H.; Goblyos, A.; Adriaans, A. E.; Cordfunke, R. A.; Ravensbergen, B.; Rietveld, M. H.; Zwart, S.; Commandeur, S.; van Leeuwen, R.; Haisma, E. M.; Schimmel, K. J. M.; den Hartigh, J.; Drijfhout, J. W.; Ghalbzouri, A. E., Eradication of meticillin-resistant *Staphylococcus aureus* from human skin by the novel LL-37-derived peptide P10 in four pharmaceutical ointments. *Int J Antimicrob Agents* 2019, 54 (5), 610-618.
22. Haisma, E. M.; de Breij, A.; Chan, H.; van Dissel, J. T.; Drijfhout, J. W.; Hiemstra, P. S.; El Ghalbzouri, A.; Nibbering, P. H., LL-37-derived peptides eradicate multidrug-resistant *Staphylococcus aureus* from thermally wounded human skin equivalents. *Antimicrob Agents Chemother* 2014, 58 (8), 4411-9.
23. Dijksteel, G. S.; Ulrich, M. M. W.; Vlig, M.; Nibbering, P. H.; Cordfunke, R. A.; Drijfhout, J. W.; Middelkoop, E.; Boekema, B., Potential factors contributing to the poor antimicrobial efficacy of SAAP-148 in a rat wound infection model. *Ann Clin Microbiol Antimicrob* 2019, 18 (1), 38.
24. Cogen, A. L.; Yamasaki, K.; Sanchez, K. M.; Dorschner, R. A.; Lai, Y.; MacLeod, D. T.; Torpey, J. W.; Otto, M.; Nizet, V.; Kim, J. E.; Gallo, R. L., Selective antimicrobial action is provided by phenol-soluble modulins derived from *Staphylococcus epidermidis*, a normal resident of the skin. *J Invest Dermatol* 2010, 130 (1), 192-200.
25. Peschel, A.; Otto, M., Phenol-soluble modulins and staphylococcal infection. *Nat Rev Microbiol* 2013, 11 (10), 667-73.
26. Cogen, A. L.; Yamasaki, K.; Muto, J.; Sanchez, K. M.; Crotty Alexander, L.; Tanios, J.; Lai, Y.; Kim, J. E.; Nizet, V.; Gallo, R. L., *Staphylococcus epidermidis* antimicrobial delta-toxin (phenol-soluble modulin-gamma) cooperates with host antimicrobial peptides to kill group A *Streptococcus*. *PLoS One* 2010, 5 (1), e8557.
27. Al-Mahrous, M.; Sandiford, S. K.; Tagg, J. R.; Upton, M., Purification and characterization of a novel delta-lysin variant that inhibits *Staphylococcus aureus* and has limited hemolytic activity. *Peptides* 2010, 31 (9), 1661-8.
28. Tappin, M. J.; Pastore, A.; Norton, R. S.; Freer, J. H.; Campbell, I. D., High-resolution 1H NMR study of the solution structure of delta-hemolysin. *Biochemistry* 1988, 27 (5), 1643-7.
29. Towle, K. M.; Lohans, C. T.; Miskolzie, M.; Acedo, J. Z.; van Belkum, M. J.; Vederas, J. C., Solution Structures of Phenol-Soluble Modulins alpha1, alpha3, and beta2, Virulence Factors from *Staphylococcus aureus*. *Biochemistry* 2016, 55 (34), 4798-806.
30. Kreger, A. S.; Kim, K. S.; Zaboretzky, F.; Bernheimer, A. W., Purification and properties of staphylococcal delta hemolysin. *Infect Immun* 1971, 3 (3), 449-65.
31. Wang, R.; Braughton, K. R.; Kretschmer, D.; Bach, T. H.; Queck, S. Y.; Li, M.; Kennedy, A. D.; Dorward, D. W.; Klebanoff, S. J.; Peschel, A.; DeLeo, F. R.; Otto, M., Identification of novel cytolytic peptides as key virulence determinants for community-associated MRSA. *Nat Med* 2007, 13 (12), 1510-4.
32. Mehlin, C.; Headley, C. M.; Klebanoff, S. J., An inflammatory polypeptide complex from *Staphylococcus epidermidis*: isolation and characterization. *J Exp Med* 1999, 189 (6), 907-18.
33. Hoffmann, E. M.; Streitfeld, M. M., The Antibiotic Activity Associated with Preparations of Delta Hemolysin of *Staphylococcus aureus*. *Can J Microbiol* 1965, 11, 203-11.
34. Joo, H. S.; Cheung, G. Y.; Otto, M., Antimicrobial activity of community-associated methicillin-resistant *Staphylococcus aureus* is caused by phenol-soluble modulin derivatives. *J Biol Chem* 2011, 286 (11), 8933-40.
35. Verdon, J.; Berjeaud, J. M.; Lacombe, C.; Hechard, Y., Characterization of anti-Legionella activity of warnericin RK and delta-lysin I from *Staphylococcus warneri*. *Peptides* 2008, 29 (6), 978-84.
36. Marchand, A.; Verdon, J.; Lacombe, C.; Crapart, S.; Hechard, Y.; Berjeaud, J. M., Anti-Legionella activity of staphylococcal hemolytic peptides. *Peptides* 2011, 32 (5), 845-51.
37. Gonzalez, D. J.; Okumura, C. Y.; Hollands, A.; Kersten, R.; Akong-Moore, K.; Pence, M. A.; Malone, C. L.; Derieux, J.; Moore, B. S.; Horswill, A. R.; Dixon, J. E.; Dorrestein, P. C.; Nizet, V., Novel phenol-soluble modulin derivatives in community-associated methicillin-resistant *Staphylococcus aureus* identified through imaging mass spectrometry. *J Biol Chem* 2012, 287 (17), 13889-98.
38. Salinas, N.; Colletier, J. P.; Moshe, A.; Landau, M., Extreme amyloid polymorphism in *Staphylococcus aureus* virulent PSMalpha peptides. *Nat Commun* 2018, 9 (1), 3512.
39. Dhople, V. M.; Nagaraj, R., Generation of analogs having potent antimicrobial and hemolytic activities with minimal changes from an inactive 16-residue peptide corresponding to the helical region of *Staphylococcus aureus* delta-toxin. *Protein Eng* 1995, 8 (3), 315-8.
40. Dhople, V. M.; Nagaraj, R., Conformation and activity of delta-lysin and its analogs. *Peptides* 2005, 26 (2), 217-25.
41. Bojer, M. S.; Lindemose, S.; Vestergaard, M.; Ingmer, H., Quorum Sensing-Regulated Phenol-Soluble Modulins Limit Persister Cell Populations in *Staphylococcus aureus*. *Front Microbiol* 2018, 9, 255.
42. Baldry, M.; Bojer, M. S.; Najarzadeh, Z.; Vestergaard, M.; Meyer, R. L.; Otzen, D. E.; Ingmer, H., Phenol-Soluble Modulins Modulate Persister Cell Formation in *Staphylococcus aureus*. *Front Microbiol* 2020, 11, 573253.
43. Zeng, P.; Xu, C.; Cheng, Q.; Liu, J.; Gao, W.; Yang, X.; Wong, K. Y.; Chen, S.; Chan, K. F., Phenol-Soluble-Modulin-Inspired Amphipathic Peptides Have Bactericidal Activity against Multidrug-Resistant Bacteria. *Chem Med Chem* 2019, 14 (16), 1547-1559.
44. Somerville, G. A.; Cockayne, A.; Durr, M.; Peschel, A.; Otto, M.; Musser, J. M., Synthesis and deformylation of Staphylococcus aureus delta-toxin are linked to tricarboxylic acid cycle activity. *J Bacteriol* 2003, 185 (22), 6686-94.
45. Jones, R. C.; Deck, J.; Edmondson, R. D.; Hart, M. E., Relative quantitative comparisons of the extracellular protein profiles of *Staphylococcus aureus* UAMS-1 and its sarA, agr, and sarA agr regulatory mutants using one-dimensional polyacrylamide gel electrophoresis and nanocapillary liquid chromatography coupled with tandem mass spectrometry. *J Bacteriol* 2008, 190 (15), 5265-78.
46. Schwartz, K.; Syed, A. K.; Stephenson, R. E.; Rickard, A. H.; Boles, B. R., Functional amyloids composed of phenol soluble modulins stabilize *Staphylococcus aureus* biofilms. *PLoS Pathog* 2012, 8 (6), e1002744.
47. Lechner, S.; Lewis, K.; Bertram, R., *Staphylococcus aureus* Persisters Tolerant to Bactericidal Antibiotics. *Microbial Physiology* 2012, 22 (4), 235-244.
48. Tayeb-Fligelman, E.; Tabachnikov, O.; Moshe, A.; Goldshmidt-Tran, O.; Sawaya, M. R.; Coquelle, N.; Colletier, J. P.; Landau, M., The cytotoxic *Staphylococcus aureus* PSMalpha3 reveals a cross-alpha amyloid-like fibril. *Science* 2017, 355 (6327), 831-833.
49. Tayeb-Fligelman, E.; Salinas, N.; Tabachnikov, O.; Landau, M., *Staphylococcus aureus* PSMalpha3 Cross-alpha Fibril Polymorphism and Determinants of Cytotoxicity. *Structure* 2020, 28 (3), 301-313 e6.
50. Yao, Z.; Cary, B. P.; Bingman, C. A.; Wang, C.; Kreitler, D. F.; Satyshur, K. A.; Forest, K. T.; Gellman, S. H., Use of a Stereochemical Strategy To Probe the Mechanism of Phenol-Soluble Modulin alpha3 Toxicity. *J Am Chem Soc* 2019, 141 (19), 7660-7664.
51. Cherry, M. A.; Higgins, S. K.; Melroy, H.; Lee, H. S.; Pokorny, A., Peptides with the same composition, hydrophobicity, and hydrophobic moment bind to phospholipid bilayers with different affinities. *J Phys Chem B* 2014, 118 (43), 12462-70.
52. R. Somayaji, M. A. R. Priyantha, J. E. Rubin, D. Church, Human infections due to *Staphylococcus pseudintermedius*, an emerging zoonosis of canine origin: report of 24 cases. *Diagnostic Microbiology and Infectious Disease*, 2016, 85(4), 471-476.

The invention claimed is:

1. An antimicrobial peptide having an amino acid sequence:

TVX$_1$X$_2$LVX$_3$WILX$_4$X$_5$X$_6$X$_7$X$_8$FX$_9$,  (SEQ ID NO: 32)

wherein X1 is selected from G, K, A, R, and Z;
X2 is selected from G, K, A, F, and V, or a conservatively substituted variant thereof;
X3 is selected from K, R, and Z;
X4 is selected from D, A, K, N, R, and Z;
X5 is selected from T, V, W, and A;
X6 is selected from V and F;
X7 is selected from K and A;
X8 is selected from K, R, and Z; and
X9 is selected from A, I, K, and W;
wherein Z=L-ornithine; wherein X2 and X5 are not both V; and wherein the C-terminal residue is unmodified or amidated; and
wherein the antimicrobial peptide has antimicrobial activity.

2. The peptide of claim 1, wherein the C-terminal residue is amidated.

3. The peptide of claim 1, wherein the carboxy terminus is unmodified.

4. The peptide claim 1, wherein the peptide has antibacterial activity against one or more of *Staphylococcus* spp. *Streptococcus* spp., *Enterococcus* spp., *Micrococcus* spp., *Escherichia* spp., *Acinetobacter* spp., *Klebsiella* spp., *Mannheimia* spp., *Pseudomonas* spp., *Pasteurella* spp., and *Mycoplasma* spp., optionally the *Staphylococcus* spp. is selected from the group consisting of *S. aureus*, optionally methicillin-resistant *S. aureus* (MRSA), *S. epidermidis*, *S. pseudintermedius*, *S. auricularis*, *S. equorum*, *S. scuri*, and *S. pseudintermedius*, and wherein
X1 is selected from G, K, A, and R;
X2 is selected from G and A;
X3 is selected from K and R;
X4 is selected from D, N, A, K, and R;
X5 is selected from T, V, and A;
X6 is V;
X7 is selected from K and A;
X8 is selected from K and R; and
X9 is selected from A and W.

5. The peptide of claim 1, wherein the antimicrobial peptide has antifungal activity against one or more of *Candida* spp., *Saccharomyces* spp. and *Kodamae ohmeri*, optionally the *Candida* spp. is selected from the group consisting of *C. albicans, C. duobushaemulonii, C. haemulonii, C. krusei*, and *C. lusitaniae*, and wherein
X1 is selected from G, K, and A;
X2 is selected from G, K, F, and A;
X3 is K;
X4 is selected from D, A, K, and N;
X5 is selected from T, V, and A;
X6 is V;
X7 is selected from K and A;
X8 is K;
X9 is A.

6. The peptide of claim 1, wherein the antimicrobial peptide has antibacterial activity against *Mannheimia* spp., optionally *M. haemolytica*, and wherein
X1 is selected from G, K, R, and Z;
X2 is selected from G, K, and A;
X3 is selected from K, R, and Z;
X4 is selected from A, K, N, R, and Z;
X5 is selected from T, V, and A;
X6 is V;
X7 is selected from K and A;
X8 is selected from K, R, and Z; and
X9 is selected from A, and W.

7. The peptide of claim 1, wherein the peptide has an amino acid sequence selected from the group consisting of:

TVGGLVKWILDTVKKFA;  (SEQ ID NO: 1)

TVGGLVKWILATVKKFA;  (SEQ ID NO: 2)

TVGGLVKWILKTVKKFA;  (SEQ ID NO: 3)

TVGGLVKWILNTVKKFA;  (SEQ ID NO: 4)

TVGGLVKWILDTVKKFI;  (SEQ ID NO: 5)

TVGGLVKWILDTVKKFW;  (SEQ ID NO: 6)

TVGGLVKWILDTVKKFK;  (SEQ ID NO: 7)

TVGVLVKWILDTVKKFA;  (SEQ ID NO: 8)

TVGGLVKWILDVVKKFA;  (SEQ ID NO: 9)

TVGGLVKWILDVVVKKFA;  (SEQ ID NO: 10)

TVGGLVKWILDTFKKFA;  (SEQ ID NO: 11)

TVGGLVKWILAAVKKFA;  (SEQ ID NO: 12)

TVGGLVKWILKAVKKFA;  (SEQ ID NO: 13)

TVKGLVKWILNVVKKFA  (SEQ ID NO: 14)

TVAGLVKWILATVKKFA;  (SEQ ID NO: 15)

TVKGLVKWILATVKKFA;  (SEQ ID NO: 16)

TVDGLVKWILATVKKFA;  (SEQ ID NO: 17)

TVKKLVKWILKTVKKFA;  (SEQ ID NO: 18)

TVKALVKWILKTVAKFA;  (SEQ ID NO: 19)

TVRALVKWILRTVAKFA;  (SEQ ID NO: 20)

TVKALVKWILKTVAKFW;  (SEQ ID NO: 21)

-continued

```
                          (SEQ ID NO: 22)
TVXALVXWILXTVAXFA, where X is L-ornithine;

(SEQ ID NO: 23)
TVRALVRWILRTVARFA;

(SEQ ID NO: 25)
TVKFLVKWILKVVVAKFA;

(SEQ ID NO: 27)
TVGGLVKWILDTVKKFA-NH₂;

(SEQ ID NO: 28)
TVGGLVKWILATVKKFA-NH₂;

(SEQ ID NO: 29)
TVGGLVKWILKTVKKFA-NH₂;

(SEQ ID NO: 30)
TVKGLVKWILNVVKKFA-NH₂;
and (SEQ ID NO: 31)
TVKALVKWILKTVAKFW-NH₂.
```

8. The peptide of claim 1, wherein X4 is a D-amino acid or the peptide consists of D-amino acids.

* * * * *

UNITED STATES PATENT AND TRADEMARK OFFICE
CERTIFICATE OF CORRECTION

PATENT NO. : 12,370,235 B2
APPLICATION NO. : 17/685943
DATED : July 29, 2025
INVENTOR(S) : Deeyagahage Hiruni Kathyana and Antonio Ruzzini Page 1 of 1

It is certified that error appears in the above-identified patent and that said Letters Patent is hereby corrected as shown below:

In the Claims

Claim 1, Column 81, Line 9-10:
"X2 is selected from G, K, A, F, and V, or a conservatively substituted variant thereof;"
Should read:
-- X2 is selected from G, K, A, F, and V; --

Claim 7, Column 82, Line 36-37:
"TVGGLVKWILDVVVKKFA (SEQ ID NO: 10);"
Should read:
-- TVGGLVKWILDWVKKFA (SEQ ID NO: 10); --

Claim 7, Column 83, Line 6-7:
"TVKFLVKWILKVVVAKFA (SEQ ID NO: 25);"
Should read:
-- TVKFLVKWILKWVAKFA (SEQ ID NO: 25); --

Signed and Sealed this
Fourteenth Day of October, 2025

John A. Squires
*Director of the United States Patent and Trademark Office*